United States Patent
Nitz et al.

(10) Patent No.: US 10,816,552 B2
(45) Date of Patent: *Oct. 27, 2020

(54) ORGANOTELLURIUM COMPOUNDS, COMPOSITIONS AND METHODS OF USE THEREOF

(71) Applicants: The Governing Council of the University of Toronto, Toronto (CA); University Health Network, Toronto (CA)

(72) Inventors: Mark Nitz, Toronto (CA); Landon J. Edgar, Midhurst (CA); Bradly G. Wouters, Toronto (CA); David Hedley, Toronto (CA); Lisa M. Willis, Toronto (CA); Matthew A. Lumba, Toronto (CA); Hanuel Park, London (CA); Ravi N. Vellanki, Toronto (CA)

(73) Assignees: The Governing Council of the University of Toronto, Toronto (CA); University Health Network, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/245,328

(22) Filed: Jan. 11, 2019

(65) Prior Publication Data

US 2019/0250165 A1 Aug. 15, 2019

Related U.S. Application Data

(63) Continuation of application No. 15/505,197, filed as application No. PCT/CA2015/050793 on Aug. 20, 2015, now Pat. No. 10,222,380.

(60) Provisional application No. 62/165,002, filed on May 21, 2015, provisional application No. 62/039,762, filed on Aug. 20, 2014.

(51) Int. Cl.
    *G01N 33/58* (2006.01)
    *C07D 421/06* (2006.01)
    *C07D 345/00* (2006.01)
    *C07H 15/04* (2006.01)
    *G01N 33/569* (2006.01)

(52) U.S. Cl.
    CPC .......... *G01N 33/58* (2013.01); *C07D 345/00* (2013.01); *C07D 421/06* (2013.01); *C07H 15/04* (2013.01); *G01N 33/569* (2013.01); *G01N 2458/15* (2013.01); *G01N 2560/00* (2013.01)

(58) Field of Classification Search
CPC .. G01N 33/58; G01N 33/569; G01N 2560/00; G01N 2458/15; C07H 15/04; C07D 345/00
USPC ...................................................... 544/162
See application file for complete search history.

(56) References Cited

U.S. PATENT DOCUMENTS 8,304,036 B2    11/2012  Jansen et al.
10,222,380 B2 *  3/2019  Nitz ....................... G01N 33/58

FOREIGN PATENT DOCUMENTS

WO    2007/044641 A2    4/2007
WO    2007/137418 A1    12/2007

OTHER PUBLICATIONS

O. Ornatsky, et al. Highly multiparametric analysis by mass cytometry. J. Immunol. Methods, 2010, 361, 1-20.
S. C. De Rosa, et al. 11-color 13-parameter flow cytometry: Identification of human naive T cells by phenotype, function, and T-cell receptor diversity. Nat. Med., 2001, 7, 245-8.
S. C. Bendall et al. A deep profiler's guide to cytometry. Trends Immunol., 2012, 33, 323-32.
S. C. Bendall et al. Single-Cell Mass Cytometry of Differential Immune and Drug Responses Across a Human Hematopoietic Continuum. Science, 2011, 332, 687-96.
Edgar, L.J. et al., Identification of hypoxic cells using an organotellurium tag compatible with mass cytometry. Angew Chem. Int. (2014) 53(43):11473-7.
Betley, Jason R. et al., Direct Screening for Phosphatase Activity by Turnover-Based Capture of Protein Catalysts. Angew. Chem. Int. (2002) 41, No. 5, 775-77.
L. A. Ba et al. Tellurium: an element with great biological potency and potential. Org. Biomol. Chem., 2010, 8, 4203-16.
R. Cunha et al. A glimpse on biological activities of tellurium compounds. An. da Acad. Bras., 2009, 81, 393-407.
S. Shaaban et al. Sulfur, selenium and tellurium pseudopeptides: Synthesis and biological evaluation. Bioorg. Med. Chem., 2014, 22, 3610-9.
L. Piovan et al. 20S proteasome as novel biological target for organochalcogenanes. Eur. J. Med. Chem., 2014, 73, 280-5.
P. Du et al. A new tellurium-containing amphiphilic molecule induces apoptosis in HCT116 colon cancer cells. Biochim. Biophys. Acta, 2014, 1840, 1808-16.
W. Cao et al. Tellurium-Containing Polymer Micelles: Competitive-Ligand Regulated Coordination Responsive Systems. J. Am. Chem. Soc., 2014, 136, 5132-7.

(Continued)

*Primary Examiner* — Kahsay Habte
(74) *Attorney, Agent, or Firm* — Bereskin & Parr LLP; Carmela De Luca

(57) ABSTRACT

A compound of formula (I):

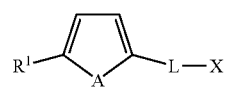

as described herein and methods and uses thereof as for mass tagging a biosensor or biologically active material.

13 Claims, 15 Drawing Sheets

(56) References Cited

OTHER PUBLICATIONS

S. G. N. Wollenhaupt et al. Seleno-and Telluro-xylofuranosides attenuate Mn-induced toxiity in C. ELEGANS VIA THE daf-16/FOXO pathway. Food Chem. Toxicol., 2014, 64, 192-199.

P. Du et al. Synthesis of amphiphilic, chalcogen-based redox modulators with in vitro cytotoxic activity against cancer cells, macrophages and icrobes. U. M. Viswanathan, K. Khairan, T. Buric, N. E. B. Saidu, Z. Xu, B. Hanf, I. Bazukyan, Medchemcomm, 2014, 5, 25.

A. Müller et al. A Novel Biologically Active Seleno-Organic Compound-I Glutathione Peroxidase-Like Activity In Vitro and ANtioxidant Capacity of PZ 51 (EBSELEN). Biochem. Pharmacol., 1984, 33, 3235-3239.

V. Jamier et al. Selenium- and Tellurium-Containing Multifunctional Redox Agents as Biochemical Redox Modulators with Selective Cytotoxicity. Chem.—A Eur. J., 2010, 16, 10920-8.

D. F. Meinerz et al. Sub-acute administration of (S)-dimethyl 2-(3-(phenyltellanyl) propanamido) succinate induces toxicity and oxidative stress in mice: unexpected effects of N-acetylcysteine. Springerplus, 2013, 2,10920-10928.

A. Cristina et al 2-Phenylethynyl-butyltellurium improves memory in mice. Neurochem. Int., 2012, 60, 409-414.

A. Ouchi et al. Sunlight Oxidation of Alkyl Aryl Tellurides to the Corresponding Carbonyl Compounds: A New Carbonyl Precursor. Org. Lett., 2009, 11, 4870-4873.

N. Kuhn et al. Ein Einfaches Verfahren Zur Synthese Von [EMe3] I UND EMe2. J. Organomet. Chem., 1986, 302, 6-8 (English abstract only).

G. Kirsch, et al. Organotellurium Compounds of Biological Interest—Unique Properties of the N-Chlorosuccinimide Oxidation Product of 9-Telluraheptadecanoic Acid. Organometallics, 1983, 2, 357-363.

K. Kobayashi, et al. Syntheses and Properties of Ditelluroxanes and Oligochalcogenoxanes: Hypervalent Oligomers with Te-O Apical Linkages in the Main Chain. Chem.—A Eur. J., 2001, 7, 4272-4279.

W. Nakanishi, The Structure of 2-Carboxyphenyl Methyl Selenoxide, Its Sodium Salt and Related Compounds in Solution, Studies by H, C and Se NMR Org. Magn. Reson., 1982, 20, 117-122.

W. Bell, et al. Homolytic reactions of diorganotellurium and diorganoditellurium compounds in solution; and EPR study J. Organomet. Chem., 1992, 430, 43-52.

R. U. Kirss and D. W. Brown, Ligand-Exchange Reactions in Organotellurides by Te NMR Spectoscopy. Organometallics, 1991, 10, 3597-3599.

D. W. Brown, et al. Pyrolysis Pathways of Symmetrical and Unsymmetrical Organotellurium (II) Compounds. Organometallics, 1991, 10, 3589-3596.

W. Tyrra, et al. Tetramethylammonium trifluoromethyltellurate(0), [NMe4] TeCF3, synthesis, characterisation and properties. J. Fluor. Chem., 2004, 125, 1437-1440.

T. M. Mccormick, et al. Reversible oxidation of a water-soluble tellurophene. ChemComm, 2013, 49, 15 11182-11184.

A. a Jahnke, Poly(3-alkyltellurophenes)s Are Solution-Processable Polyheterocycles. J. Am. Chem. Soc., 2013, 135, 951-4.

G. L. Gibson, et al. Effect of Group-14 and Group 16 Substitution on the Photophysics of Structurally Related Donor-Acceptor Polymers. J. Phys. Chem., 2013, 117, 16606-16615.

M. Kaur, A novel tellurophene-containing conjugated polymer with a dithiophenyl diketopyrrolopyrrole unit for use in organic thin film transistors. Chem. Commun. (Camb)., 2013, 49, 5495-7.

M. M. Campos-vallette and R. E. Clavijo C. Molecular Vibrational Constants and Chemical Bonding in Five-Membered Heteratomic Compounds. Spectrosc. Lett., 1985, 18, 759-766.

D. P. Sweat and C. E. Stephens, A modified synthesis of tellurophene using NaBH4 to generate sodium telluride. J. Organomet. Chem., 2008, 693, 2463-2464.

T. J. Barton and R. W. Roth, A convenient synthesis of tellurophene. J. Organomet. Chem., 1972, 39, 66-68.

S. Kotha and P. Khedkar, Rongalite: A Useful Green Reagent in Organic Synthesis. Chem. Rev., 2012, 112, 1650-80.

J. P. Marino and H. N. Nguyen, Bulky Trialkylsilyl Acetylenes in the Cadiot-Chodkiewicz Cross-Coupling Reaction. J. Org. Chem., 2002, 67, 6841-6844.

M. X.-W. Jiang, et al. Contingency and Serendipity in the Reactions of Fischer Carbene Complexes with Conjugated Triynes. J. Am. Chem. Soc., 2004, 126, 5970-5971.

L. Engman, et al. Thioredoxin Reductase and Cancer Cell Growth Inhibition by Organotellurium Compounds that Could be Selectively Incorporated into Tumor Cells. Biochim. Biophys. Acta, 2003, 11, 5091-5100.

M. McNaughton, et al. Cyclodextrin-Derived Diorganyl Tellurides as Glutathione Peroxidase Mimics and Inhibitors of Thioredoxin Reductase and Cancer Cell Growth. J. Med. Chem., 30 2004, 47, 233-9.

C. Pavlik, et al. Synthesis and fluorescent characteristics of imidazole-indocyanine green conjugates. Dyes Pigm. 011, 89, 9.

C. Giesen et al. Highly multiplexed imaging of tumor tissues with subcellular resolution by mass cytometry. Nature Methods 11: 417-422 (2014).

X Lou, et al. Polymer-Based Elemental Tags for Sensitive Bioassays. Angew Chem Int Ed Engl 2007 46:6111-4.

D Majonis et al. Synthesis of a Functional Metal-Chelating Polymer and Steps toward Quantitative Mass Cytometry Bioassays. Anal Chem 2010 82: 8961-9.

Galasso, V. et al., "Theoretical study of the chalcogen-carbon coupling constants in the chalcogen heterocyclopentadienes". Journal of Molecular structure, Jan. 1, 1982 pp. 53-58.

Park, H. et al., Organotellurium scaffolds for mass cytometry reagent development. Org. Biomol. Chem. (2015) 13 (25):7027-33.

* cited by examiner

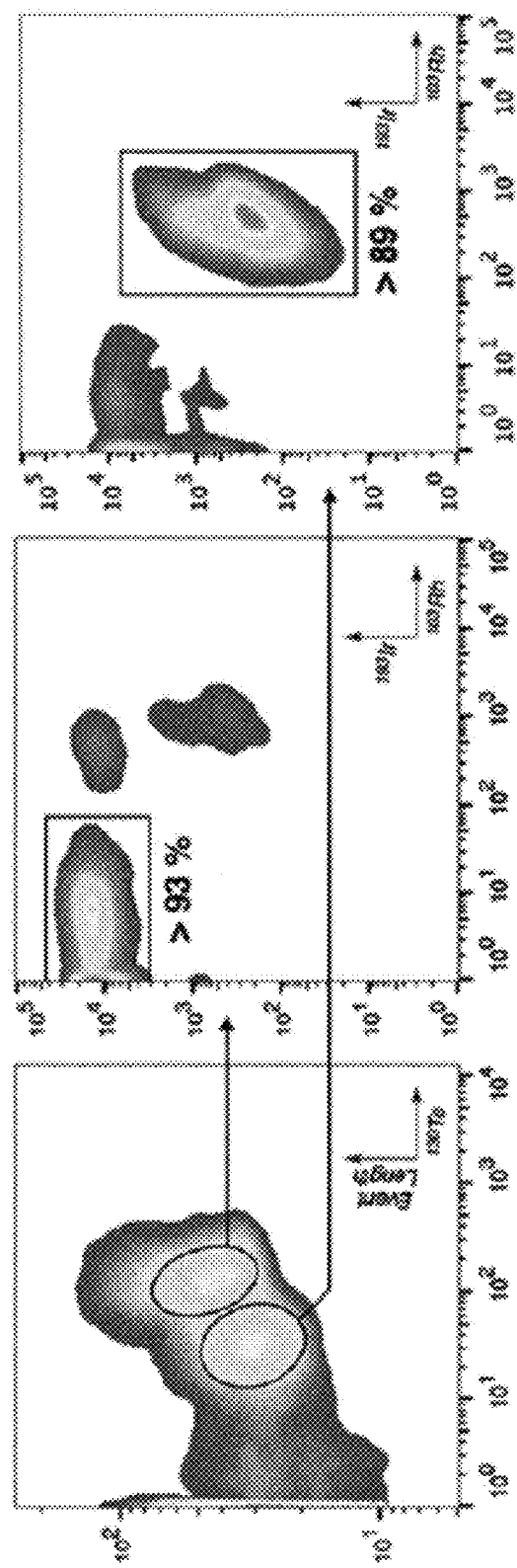

ORGANOTELLURIUM COMPOUNDS, COMPOSITIONS AND METHODS OF USE THEREOF

CROSS REFERENCE TO RELATED APPLICATIONS

The present application is a continuation of copending U.S. patent application Ser. No. 15/505,197, filed Feb. 20, 2017, which is a National stage entry of International Application No. PCT/CA2015/050793, filed Aug. 20, 2015, which claims priority to U.S. Provisional Patent Application No. 62/039,762, filed Aug. 20, 2014 and U.S. Provisional Patent Application No. 62/165,002, filed May 21, 2015, each of which are incorporated herein by reference in their entirety.

FIELD

The application pertains to organotellurophene compounds and particularly to organotellurophene probes for mass cytometry.

BACKGROUND

Characterization of single cells in tissue samples requires a highly parameterized assay.[1] Fluorescence-based flow cytometry (FC) has been the method of choice to study heterogeneous cell populations as it allows for 5-10 parameters to be routinely analyzed.[2] However, FC cannot be used for highly parameterized assays (>20 parameters) due to the spectral overlap of the fluorophores used for analyte detection.[3] A solution to this problem is to substitute the optical detection and fluorescently tagged antibodies in FC, for mass detection with an inductively-coupled plasma spectrometer (ICP-MS) and isotope-tagged antibodies. This technology, known as mass cytometry (MC), is capable of detecting numerous bioorthogonal isotopes (theoretically >100) with single mass unit resolution over multiple orders of magnitude.[3] MC allows experiments analogous to flow cytometry but with significantly greater parameterization. MC has been used to detect and quantify 34 cellular parameters simultaneously to reveal the drug response across a human hematopoietic continuum.[4]

MC experiments can be done by using commercially available MaxPar® to label antibodies with metal chelating polymers that bind a range of high molecular weight metal isotopes, usually lanthanides. Element tags attached to polymer backbones are described in U.S. Pat. No. 9,012,239. Specific examples disclosed include elemental tags comprising the metal chelating groups diethylenetriaminepentaacetate (DTPA) and 1,4,7,10-tetraazacyclododecane-1,4,7,10-tetraacetic acid (DOTA).

Other mass tagged reagents are desirable.

The first organotellurium compound was synthesized by Wöhler in 1840.[6] Increasingly organotellurium compounds are being investigated in living systems, although this area of research remains underdeveloped.[7,8] Tellurium has no known biological role in prokaryotic or eukaryotic cells. In biological systems, tellurium metabolism is poorly understood, however it is presumed to follow the metabolic pathway of its analogue, selenium. Microorganisms have been found to methylate inorganic tellurium to volatile or ionic species for excretion. Experimental evidence of this process is scarce due to the instability of the metabolites[7]. However the number reports of cellular studies involving aryl, vinylic, alkynyl and alkyl telluroethers in biological systems are increasing.[9-14] The majority of this research has been based upon the ability of aryl telluroethers to mimic glutathione peroxidase activity providing, in some cases, resistance to oxidative stress and in other case disregulating redox homeostatsis leading to appoptosis.[15,16] Recent murine studies have shown diverse effects from the expected toxicity of an amino acid based aryl telluroether to increased memory in mice treated with an alkyl telluroether.[17,18]

SUMMARY

Mass Cytometry (MC) probes that can, in an embodiment, be used to assay cellular biochemistry are described herein. FIG. 1 depicts an embodiment of an MC probe. Ideally, the mass tag should be accessible in a high yielding synthesis amenable to isotope incorporation, be stable under biologically-relevant conditions and have low toxicity. An MC-probe (Telox) for measuring cellular hypoxia was constructed (described in U.S. application Ser. No. 62/039,-762).[5] This probe used a 2-nitroimidazole as the activity group for hypoxic-specific labelling and a methyl telluroether functionality as the tag unit for MC detection.[5] Tellurium was chosen to be the element for detection as it is known to form stable bonds with carbon and it has 8 naturally occurring isotopes that can be accessed to generate a series of uniquely identifiable, biologically indistinguishable MC probes using the same chemistry.

In Telox, the telluroether functionality had moderate stability and a metabolic $LD_{50}$ value close to the required assay concentration.

Described herein are the synthesis, aqueous/aerobic stability and in vitro toxicity of a series of alkyl telluroethers and tellurophene functional groups.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

Embodiments of the present disclosure will now be described in relation to the drawings in which:

FIGS. 4A-E show a schematic representation and density maps and plots. FIG. 4A is a schematic representation of Telox/Telox2 cell labelling for analysis via mass cytometry on a second-generation CyTOF instrument. FIG. 4b) is a density map of signal event length vs. $^{130}$Te signal (arbitrary units). FIG. 4c) is a density plot output from the top-right gate in b) of $^{193}$Ir signal (arbitrary units) vs. $^{103}$Rh signal (arbitrary units). More than 93% of detected events fall in the square gate. FIG. 4d) is a density plot output from the bottom-left gate in b) of $^{193}$Ir signal (arbitrary units) vs. $^{103}$Rh signal (arbitrary units). More than 89% of detected events fall in the square gate. FIG. 4e) is a population histograms of cell $^{130}$Te content (arbitrary units). Oxygen concentrations are listed as numerical percentages, P=Pimonidazole (100 µM). Blue and red histograms are Pimonidazole-negative controls. Orange and green histograms are Pimonidazole- positive competition experiments. Note: warmer colors in density plots indicate higher cell population density.

FIGS. 8A and B show a) the absolute $^{130}$Te signal as a function of concentration as determined by mass cytometry analysis of HCT116 cells incubated with the exemplary compound, Telox-2, for 3 hours in either near-anoxic (~0% O$_2$), hypoxic (~1% O$_2$) or normoxic (21% O$_2$) atmosphere; and b) the signal-to-noise (fold-change) representation of the data presented in part a.

DETAILED DESCRIPTION OF THE DISCLOSURE

I. Definitions

Figure 1:
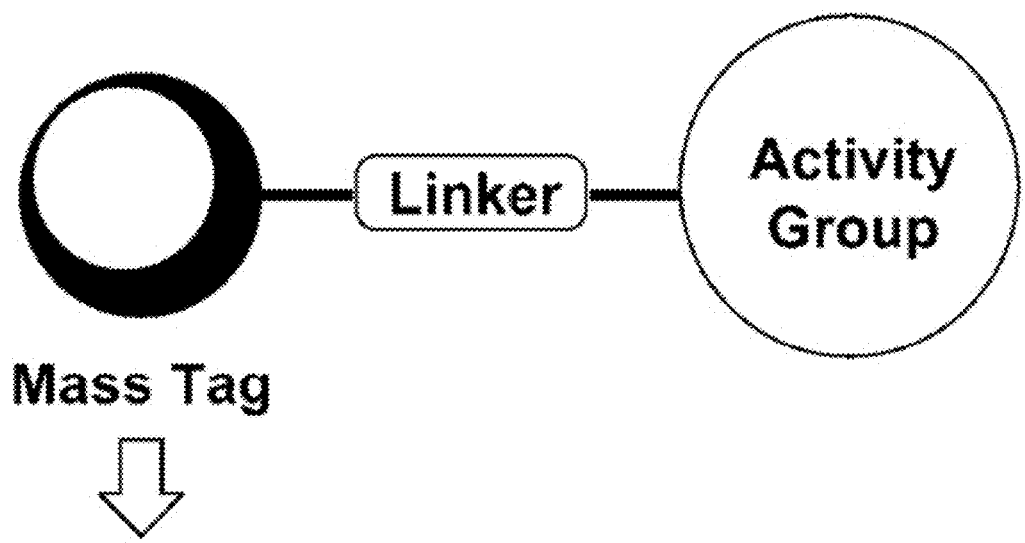
FIG. 1 shows the general requirements and design of a mass cytometry probe in certain embodiments of the present application.

The term "a cell" as used herein includes a single cell as well as a plurality or population of cells.

The term "antibody" as used herein is intended to include monoclonal antibodies, polyclonal antibodies, and chimeric antibodies and binding fragments thereof. The antibody may be from recombinant sources and/or produced in transgenic animals. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques. Antibody fragments as used herein mean binding fragments The term "biosensor" as used herein means any enzyme substrate that 1) is converted by an enzyme to reactive products (such as but not limited to, quinone methide intermediates), insoluble products and/or membrane localizing products (e.g. fatty acid containing products), wherein said products label a cell (e.g. a cell constituent), the local tissue environment or is an irreversible enzyme inhibitor that labels active enzymes, and 2) can be conjugated to an organotellurophene compound, optionally a compound of formula (I). In some embodiments, the biosensor is coupled to and/or further comprises one or more mass tags or a supporting structure of a mass tag.

The term "biologically active material" as used herein means an entity selected from a cell, virus, subcellular particle, polypeptide, nucleic acid, peptidic nucleic acid, oligosaccharide, polysaccharide lipopolysaccharide, cellular metabolite, hapten, hormone, pharmacologically active substance, alkaloid, steroid, vitamin, amino acid and sugar, and includes for example synthetic mimetics thereof. In some embodiments, the biologically active material is coupled to and/or further comprises one or more mass tags or a supporting structure of a mass tag.

The term "distinct tellurium isotope" as used herein refers to Te atoms in a compound having one or more atoms of a single tellurium isotope. For example, a series of mass tagged entities can be employed in an assay each having a different distinct terllurium isotope, such that each compound comprising a distinct tellurium isotope is distinguishable from other compounds.

The term "distinct mass" as used herein indicates that the compound has one or more atoms of a single tellurium isotope or a unique combination of tellurium isotopes alone (e.g. distinct tellurium mass) or in combination with other mass tags. An example includes a series of compounds, optionally polymers, each with different levels of different tellurium isotopes alone or combined with other mess tags, optionally for use in barcoding embodiments. Alternatively the compound for example an enzyme substrate may comprise multiple isotopes of tellurium alone or in combination with other mass tags. Upon cleavage of the substrate, a ratiometric approach can be used to assess whether the enzyme is active.

The term "mass tag" as used herein refers to a molecule that comprises at least one specific elemental isotopic composition that serves to distinguish a molecule to which the tag is attached, or optionally the tag itself, from other molecules comprising a different elemental isotopic composition using a mass spectral analysis. In some embodiments, the mass tag comprises at least one elemental isotope and a supporting structure for the at least one elemental isotope.

The term "metabolic labelling" as used herein refers to incorporation of a biomolecule into a macromolecule, for example incorporation of an amino acid into a protein, or a monosaccharide into a polysaccharide or glycoprotein.

As used herein "organotellurophene tag" means any tellurophene containing compound comprising a tellurophene moiety and a linker (L) that is for example compact and can be conjugated to biosensor, a polymeric backbone and/or a biologically active material and includes for example organotellurophene compounds described herein and/or described in U.S. application 62/039,762, hereby incorporated by reference. For example, the organotellurophene tag can comprise a tellurophene moiety, a linker conjugated to a biosensor such as an antibody either directly or indirectly, optionally indirectly via a polymer backbone.

The term "protease" as used herein is intended to include peptidases and proteinases and is the subset of enzymes that can catalyze the cleavage of a peptide bond and includes for example cysteine proteases, aspartate proteases, metalloproteases and serine proteases.

A "subcellular particle" as used herein includes an organelle, such as nucleus, lysosome, endosome, mitochondria, microsomes and the like.

As used in this application, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The present description refers to a number of chemical and biological terms and abbreviations used by those skilled in the art. Nevertheless, definitions of selected terms are provided for clarity and consistency.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

As used in this application, the singular forms "a", "an" and "the" include plural references unless the content clearly dictates otherwise. For example, an embodiment including "a compound" should be understood to present certain aspects with one compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In embodiments of the present application, the compounds described herein may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having alternate stereochemistry. It is intended that any optical isomers, as separated, pure or partially purified optical isomers or racemic mixtures thereof are included within the scope of the present application.

The term "alkyl" as used herein, whether it is used alone or as part of another group, means straight or branched chain, saturated alkyl groups. The number of carbon atoms that are possible in the referenced alkyl group are indicated by the numerical prefix "$C_{n1\text{-}n2}$". For example, the term $C_{1-6}$alkyl means an alkyl group having 1, 2, 3, 4, 5 or 6 carbon atoms.

The term "alkylene" as used herein, whether it is used alone or as part of another group, means straight or branched chain, saturated alkylene group; that is a saturated carbon chain that contains substituents on two of its ends. The number of carbon atoms that are possible in the referenced alkylene group are indicated by the numerical prefix "$C_{n1\text{-}n2}$". For example, the term $C_{4-20}$alkylene means an alkylene group having 4, 5, 6, 7, 8, 9, 10, 11, 12, 13, 14, 15, 16, 17, 18, 19 or 20 carbon atoms.

The term "aryl" as used herein, whether it is used alone or as part of another group, refers to mono-, bi- or tricyclic groups that contain at least one aromatic carbocycle. In an embodiment of the present application, the aryl group contains 6, 9, 10 or 14 carbon atoms, such as phenyl, naphthyl, indanyl or anthracenyl.

The term "tellurophene" as used herein refers to the a compound of the formula:

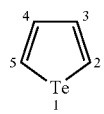

wherein the numbers are used in the naming of various substituents on the tellurophene ring.

The term "organotellurophene" refers to a tellurophene substituted with at least one carbon-containing group.

The term "electron withdrawing group" as used herein refers to an atom or functional group that removes electron density from a conjugated $\pi$ system, making the $\pi$ system more electrophilic.

The term "unsaturated" as used herein refers to compounds or groups comprising at least one double bond and includes compounds and groups with a maximum number of double bonds and aromatic compounds and groups.

The terms "protective group" or "protecting group" or "PG" or the like as used herein refer to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas). Examples of suitable protecting groups include, but are not limited to t-Boc, Ac, Ts, Ms, silyl ethers such as TMS, TBDMS, TBDPS, Tf, Ns, Bn, Fmoc, benzoyl, dimethoxytrityl, methoxyethoxymethyl ether, methoxymethyl ether, pivaloyl, p-methyoxybenzyl ether, tetrahydropyranyl, trityl, ethoxyethyl ethers, carbobenzyloxy, benzoyl and the like.

The term "functional group" as used herein refers to a group of atoms or a single atom that will react with another group of atoms or a single atom (so called "complementary functional group") to form a chemical interaction between the two groups or atoms.

The term "complementary functional group" as used herein means a functional group that interacts, or reacts, with another specified functional group, to form a chemical interaction. In an embodiment, the chemical interaction is a covalent bond or an ionic bond. In another embodiment, the chemical interaction is a covalent bond.

The term "reacts with" as used herein generally means that there is a flow of electrons or a transfer of electrostatic charge resulting in the formation of a chemical interaction.

The term "chemical interaction" as used herein refers to the formation of either a covalent of ionic bond between the reactive functional groups.

The term "available hydrogen atoms" as used herein refers to hydrogen atoms on a molecule that can be replaced with another group under conditions that will not degrade or decompose the parent compound. Such conditions include the use of protecting groups to protect sensitive functional groups in the molecule while the hydrogen atom is being replaced.

The term "compound(s) of the application" or "compound(s) of the present application" and the like as used herein includes organotellurophene compounds comprising a tellurophene moiety, a linker and a reactive functional group wherein the reactive functional group is capable of being functionalized with a biosensor, a biologically active material and/or a polymeric backbone, organotellurophene compounds comprising a tellurophene moiety, a linker and a biosensor, a biologically active material and/or a polymeric backbone and particularly compounds of formula (I), (II) and (IIa), and pharmaceutically acceptable salts and/or solvates thereof as defined herein.

An acid addition salt means any organic or inorganic salt of any basic compound. Basic compounds that form an acid addition salt include, for example, compounds comprising an amine group. Illustrative inorganic acids which form suitable salts include hydrochloric, hydrotrifluoroacetic, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to one skilled in the art.

A base addition salt means any organic or inorganic base addition salt of any acidic compound. Acidic compounds that form a base addition salt include, for example, compounds comprising a carboxylic acid group. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. The selection of the appropriate salt will be known to a person skilled in the art.

The formation of a desired compound salt is achieved using standard techniques. For example, the neutral compound is treated with an acid or base in a suitable solvent and the formed salt is isolated by filtration, extraction or any other suitable method.

The term "solvate" as used herein means a compound of the formula (I) or formula II or a pharmaceutically acceptable salt of a compound of the formula (I) or formula (II), wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the appliction will vary depending on the compound and the solvate. In general, solvates are formed by dissolving the compound in the appropriate solvent and isolating the solvate by cooling or using an antisolvent. The solvate is typically dried or azeotroped under ambient conditions.

As used herein, the term "effective amount" means an amount effective, and for periods of time necessary, to achieve a desired result.

The term "polymeric backbone" as used herein refers to the main chain of a suitable polymer comprising a series of covalently bonded atoms that together create the continuous chain (straight or branched) of the polymeric molecule. The polymer is any suitable polymer or copolymer comprising at least one compound of formula (IIa) covalently linked thereto. In some embodiments, the polymeric backbone comprises functional atoms that increase water solubility, for example, polyethyleneglycol units, and/or, attached functional groups that increase water solubility, for example, zwitter ionic groups. In some embodiments, the polymeric backbone is coupled to and/or further comprises one or more biosensors, biologically active materials, mass tags and/or a supporting structure of a mass tag.

The definitions and embodiments described in particular sections are intended to be applicable to other embodiments herein described for which they are suitable as would be understood by a person skilled in the art. For example, in the following passages, different aspects are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Compounds, Compositions and Kits

Functionalized organotellurophene compounds as probes for mass cytometry (MC) have been prepared as described in the present application. The organotellurophene compounds were characterized by nuclear magnetic resonance spectroscopy and their stability monitored through ultraviolet-visible spectroscopy. The metabolic toxicity and their subsequent potential as MC probes have also been assessed in the studies of the present application.

Accordingly, the present application includes an organotellurophene compound, comprising a tellurophene moiety, a linker and a reactive functional group wherein the reactive functional group is capable of being functionalized with a biosensor, a biologically active material or a polymeric backbone. In a further embodiment, the present application includes an organotellurophene compound, comprising a tellurophene moiety, a linker and a biosensor, a biologically active material and/or a polymeric backbone.

In an embodiment, the organotellurophene compounds of the application comprise a tellurophene optionally functionalized at the 5-position with a bulky group and/or an electron withdrawing group and at the 2-position with a linker group that is attached to a reactive functional group X. In another embodiment, the organotellurophene compounds comprise of a tellurophene optionally functionalized at the 5-position with a bulky group and/or an electron withdrawing group and at the 2-position with a linker group that is attached to a biosensor, a biologically active material and/or a polymeric backbone. It is an embodiment that the substituent at the 5-position helps to stabilize the organotellurophene compound, for example by inhibiting oxidation of the Te atom.

In another embodiment, the present application includes an organotellurophene compound of formula (I):

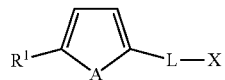

(I)

wherein A is a naturally occurring isotope of Te;
$R^1$ is selected from H, unsubstituted or substituted C1-C20alkyl, unsubstituted or substituted C3-C20cycloalkyl, unsubstituted or substituted aryl and an electron withdrawing group;
L is $C_{1-30}$alkylene, unsubstituted or substituted with one or more substituents and/or optionally interrupted with one or more heteromoieties independently selected from O, S, $NR^7$, and/or optionally interrupted with one or more of C(O) and C(S);
$R^7$ is independently selected from H, PG and $C_{1-6}$alkyl;
X is a reactive functional group selected from halo, OH, OTs, OMs, C(O)H, C(O)$OR^8$, C(O)$NR^9R^{10}$, O—C(O)—$OR^{11}$, O—C(O)—$NR^{12}$, C(O)$ONR^{13}R^{14}$, C(O)$R^{15}$, C(O)$SR^{16}$ and $NR^{17}R^{18}$;
$R^8$ is selected from H, $C_{1-6}$alkyl, aryl and $C_{1-6}$alkylenearyl, the latter three groups being unsubstituted or substituted with one or more of halo and $NO_2$;
$R^9$ and $R^{10}$ are independently selected from H, $C_{1-6}$alkyl, aryl and $C_{1-6}$alkylenearyl, the latter three groups being unsubstituted or substituted with one or more of halo and $NO_2$, or $R^9$ and $R^{10}$, together with the N atom to which they are bonded, form a 4 to 12 membered monocyclic or bicyclic, saturated or unsaturated ring unsubstituted or substituted with one or more =O, =S, halo and C1-6alkyl;
$R^{11}$ is selected from $C_{1-6}$alkyl, aryl and $C_{1-6}$alkylenearyl, the latter three groups being unsubstituted or substituted with one or more of halo and $NO_2$;
$R^{12}$ is selected from $C_{1-6}$alkyl, aryl and $C_{1-6}$alkylenearyl, the latter three groups being unsubstituted or substituted with one or more of halo and $NO_2$;
$R^{13}$ and $R^{14}$ are independently selected from H, $C_{1-6}$alkyl, aryl and $C_{1-6}$alkylenearyl, the latter three groups being unsubstituted or substituted with one or more of halo and $NO_2$, or
$R^{13}$ and $R^{14}$, together with the N atom to which they are bonded, form a 4 to 12 membered monocyclic or bicyclic, saturated or unsaturated ring unsubstituted or substituted with one or more =O, =S, halo and $C_{1-6}$alkyl;
$R^{15}$ is halo;
$R^{16}$ is selected from $C_{1-6}$alkyl, aryl and $C_{1-6}$alkylenearyl, the latter three groups being unsubstituted or substituted with one or more of halo and $NO_2$;
$R^{17}$ and $R^{18}$ are independently selected from H, C(O)$C_{1-6}$alkyl, $C_{1-6}$alkyl, aryl and $C_{1-6}$alkylenearyl, the latter three groups being unsubstituted or substituted with one or more of halo and $NO_2$, or
$R^{17}$ and $R^{18}$, together with the N atom to which they are bonded, form a 4 to 12 membered monocyclic or bicyclic, saturated or unsaturated ring unsubstituted or substituted with one or more =O, =S, halo and $C_{1-6}$alkyl; and
one or more available hydrogens are optionally replaced with D;
or a salt and/or solvate thereof;
with proviso that when X is C(O)$OR^{19}$ and $R^{19}$ is H or $C_{1-6}$alkyl, L is not $C_{1-8}$alkylene; and
when X is OH, L is not $C_{1-2}$alkylene.

In an embodiment, $R^1$ in the compounds of formula (I) is an electron withdrawing group selected from $C(O)R^2$, $C(R^3)_3$, $C\equiv N$, and $NO_2$, wherein $R^2$ is selected from H and $C_{1-6}$alkyl and $R^3$ is halo.

In an embodiment, the substituents on $R^1$ in the compounds of formula (I) are independently selected from one or more of halo, $C_{1-6}$ alkyl and $C_{1-6}$alkoxy.

It is a further embodiment that $R^1$ in the compounds of formula (I) is H, unsubstituted or substituted $C_1$-$C_{10}$alkyl, unsubstituted or substituted $C_3$-$C_{10}$cycloalkyl, unsubstituted or substituted phenyl and an electron withdrawing group selected from $C(O)R^2$ and $C(R^3)_3$. In another embodiment, the substituents on $R^1$ are independently selected from one or more of halo and $C_{1-3}$alkyl, $R^2$ is selected from H and $C_{1-6}$alkyl; and $R^3$ is F, Cl, Br, and I. In a further embodiment, $R^1$ is selected from H and $C(R^3)_3$ wherein $R^3$ is F. It is an embodiment that $R^1$ is H.

In an embodiment, the substituents on L in the compounds of formula (II) are independently selected from halo, $C_{1-6}$alkyl, $C_{1-6}$alkoxy, $C(O)R^4$ and $NR^5R^6$, wherein $R^4$ is selected from H and $C_{1-6}$alkyl; and $R^5$ and $R^6$ are independently selected from H, PG, $C(O)C_{1-20}$alkyl and $C(O)OC_{1-20}$ alkyl.

In an embodiment, L in the compounds of formula (I) is a $C_{1-25}$alkylene, unsubstituted or substituted with one or more substituents independently selected from $C_{1-3}$alkyl, $C(O)R^4$ and $NR^5R^6$, and/or optionally interrupted with one or more heteromoieties independently selected from O and $NR^7$, and/or optionally interrupted with $C(O)$, $R^4$ is selected from H and $C_{1-2}$alkyl, $R^5$ and $R^6$ are independently selected from H, PG, $C(O)C_{1-6}$alkyl and $C(O)OC_{1-6}$alkyl, and $R^7$ is independently selected from H and PG.

In another embodiment, L in the compounds of formula (I) is a $C_{1-26}$alkylene, unsubstituted or substituted with one or more substituents independently selected from $NR^5R^6$, and/or optionally interrupted with one or more heteromoieties independently selected from O and $NR^7$, and/or optionally interrupted with $C(O)$; $R^5$ and $R^6$ are independently selected from H, PG, and $C(O)OC_{1-4}$alkyl; and $R^7$ is H.

In an embodiment, X in the compounds of formula (I) is a reactive functional group selected from Cl, Br, I, OH, $C(O)OR^8$, $C(O)NR^9R^{10}$, $O$—$C(O)$—$OR^{11}$, $C(O)ONR^{13}R^{14}$, $C(O)R^{15}$ and $NR^{15}R^{18}$; $R^8$ is selected from H and $C_{1-2}$alkyl; $R^9$ and $R^{10}$ are independently selected from H, $C_{1-6}$alkyl, aryl and $C_{1-6}$alkylenearyl, wherein the latter three groups are unsubstituted or substituted with one or more of halo and $NO_2$; $R^{11}$ is a phenyl, unsubstituted or substituted with one or more of F, Cl, Br, I and $NO_2$, $R^{13}$ and $R^{14}$ are independently selected from H and $C_{1-2}$alkyl or $R^{13}$ and $R^{14}$, together with the N atom to which they are bonded, form a 4 to 10 membered monocyclic or bicyclic ring unsubstituted or substituted with one or more =O, and =S; $R^{15}$ is Cl or Br; and $R^{17}$ and $R^{18}$ are independently selected from H, $C(O)C_{1-3}$alkyl or $R^{17}$ and $R^{18}$, together with the N atom to which they are bonded, form a 4 to 12 membered monocyclic or bicyclic ring unsubstituted or substituted with one or more =O, and =S.

In another embodiment, X in the compounds of formula (I) is a reactive functional group selected from Cl, OH, $C(O)OR^8$, $C(O)NR^9R^{10}$, $O$—$C(O)OR^{11}$, $C(O)ONR^{13}R^{14}$ and $NR^{17}R^{18}$; wherein $R^8$ is H; $R^9$ and $R^{10}$ are independently selected from H, $C_{1-6}$alkyl and $C_{1-6}$alkylenearyl, wherein the latter three groups are unsubstituted or substituted with one or more of halo and $NO_2$; $R^{11}$ is a phenyl substituted with $NO_2$, $R^{13}$ and $R^{14}$ together with the N atom to which they are bonded, form a 4 to 6 membered monocyclic ring substituted with =O; and $R^{17}$ and $R^{18}$ are independently selected from H, $C(O)C_{1-2}$alkyl or $R^{17}$ and $R^{18}$, together with the N atom to which they are bonded, form a 4 to 10 membered bicyclic ring substituted with =O.

In an embodiment, the compound of formula (I) is selected from:

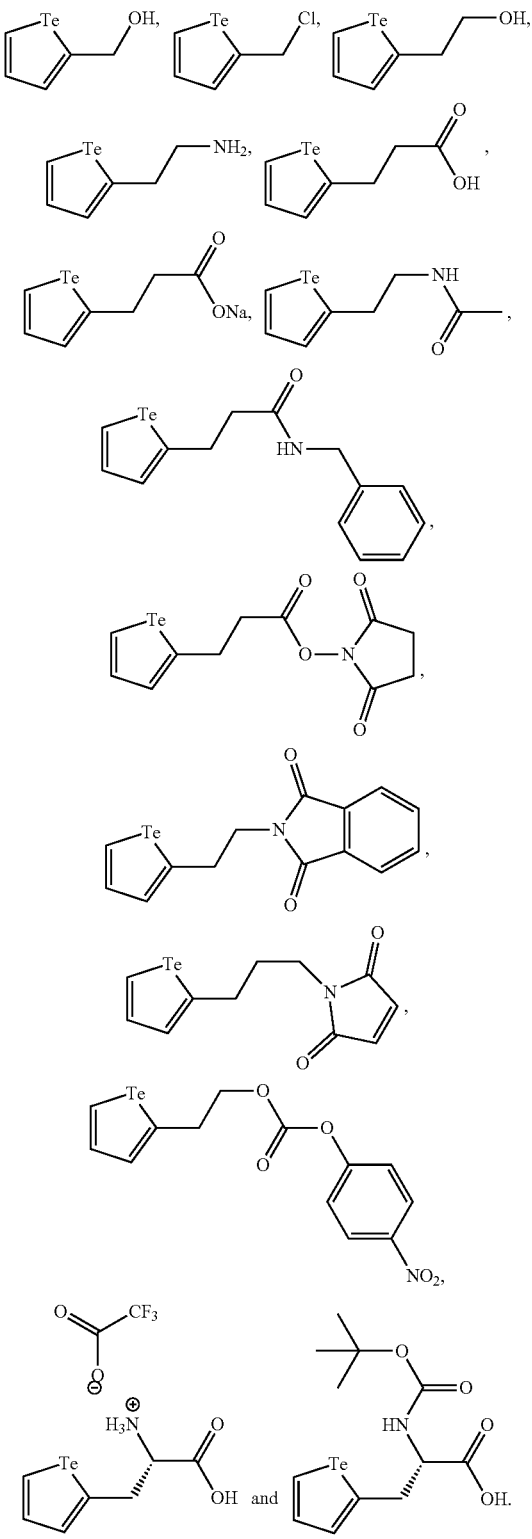

In an embodiment, the present application also includes an organotellurophene compound of formula (II):

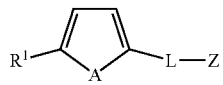

wherein A is a naturally occurring isotope of Te;
R1 is selected from H, unsubstituted or substituted C1-C20alkyl, unsubstituted or substituted C3-C20cycloalkyl, unsubstituted or substituted aryl and an electron withdrawing group;
L is $C_{1-20}$alkylene, unsubstituted or substituted with one or more substituents and/or optionally interrupted with one or more heteromoieties independently selected from O, S, $NR^7$, and/or optionally interrupted with one or more of C(O) and C(S);
$R^7$ is independently selected from H, PG and $C_{1-6}$alkyl. and
Z is a biosensor, biologically active material, or polymeric backbone; and
or a salt and/or solvate thereof.

In an embodiment, $R^1$ in the compounds of formula (II) is an electron withdrawing group selected from $C(O)R^2$, $C(R^3)_3$, C≡N, and $NO_2$, wherein $R^2$ is selected from H and $C_{1-6}$alkyl and $R^3$ is halo.

In an embodiment, the substituents on $R^1$ in the compounds of formula (II) are independently selected from one or more of halo, $C_{1-6}$ alkyl and $C_{1-6}$alkoxy.

In another embodiment, $R^1$ in the compounds of formula (II) is selected from H, unsubstituted or substituted $C_1$-$C_{10}$alkyl, unsubstituted or substituted $C_3$-$C_{10}$cycloalkyl, unsubstituted or substituted phenyl and an electron withdrawing group selected from $C(O)R^2$ and $C(R^3)_3$; the substituents on $R^1$ are independently selected from one or more of halo and $C_{1-3}$alkyl; $R^2$ is selected from H and $C_{1-6}$ alkyl; and $R^3$ is F, Cl, Br, and I.

In a further embodiment, $R^1$ in the compounds of formula (II) is selected from H and $C(R^3)_3$ wherein $R^3$ is F.

In yet a further embodiment, $R^1$ in the compounds of formula (II) is H.

In an embodiment, the substituents on L in the compounds of formula (II) are independently selected from halo, $C_{1-6}$alkyl, $C_{1-6}$alkoxy, $C(O)R^4$ and $NR^5R^6$, wherein $R^4$ is selected from H and $C_{1-6}$alkyl; and $R^5$ and $R^6$ are independently selected from H, PG, $C(O)C_{1-20}$alkyl and $C(O)OC_{1-20}$alkyl.

In an embodiment, L in the compounds of formula (II) is a $C_{1-26}$alkylene, unsubstituted or substituted with one or more substituents independently selected from $C_{1-3}$alkyl, $C(O)R^4$ and $NR^5R^6$, and/or optionally interrupted with one or more heteromoieties independently selected from O and $NR^7$, and/or optionally interrupted with C(O); $R^4$ is selected from H and $C_{1-2}$alkyl; $R^5$ and $R^6$ are independently selected from H, PG, $C(O)C_{1-6}$alkyl and $C(O)OC_{1-6}$alkyl; and $R^7$ is independently selected from H and PG.

In another embodiment, L in the compounds of formula (II) is a $C_{1-26}$alkylene, unsubstituted or substituted with one or more substituents independently selected from $NR^5R^6$, and/or optionally interrupted with one or more heteromoieties independently selected from O and $NR^7$, and/or optionally interrupted with C(O); $R^5$ and $R^6$ are independently selected from H, PG, and $C(O)OC_{1-4}$alkyl; and $R^7$ is H.

In an embodiment, Z in the compounds of formula (II) is a biosensor.

In an embodiment, biosensor is an oxidoreductase substrate, such as a xanthine oxidase substrate or a P450 substrate. As described herein, xanthine oxidase catalyzes the reduction the of 2-nitroimidazole component of Telox and Telox2.

In another embodiment, the biosensor further comprises a mass tag or a supporting structure of a mass tag, wherein the mass tag or supporting structure is optionally directly attached to the biosensor or attached through a linker, such as a linker L as defined herein.

In another embodiment, the biosensor is 2-nitroimidazole.

In a further embodiment, the compound of formula (II) is selected from:

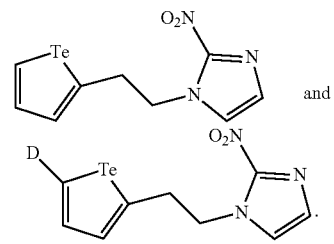

As demonstrated herein, these compounds could be used to label cells under hypoxic conditions. Such compounds when incubated with cells under low oxygen conditions undergo an enzyme catalyzed reduction of the 2-nitroimidazole functionality to produce the electrophilic protein-labelling nitrenium ion which forms adducts, allowing labelling of hypoxic cells.

In an embodiment, a series of these compounds, each comprising one or more different isotopes of Te can be used, for example, to profile different test variables in a single mass cytometry.

A variety of enzyme substrates can be used as biosensors including for example substrates for oxidoreductases, glycosyl hydrolases, lipases, phosphatases, kinases and proteases Active site specific reactive compounds specific for proteases, for, example comprising an electrophilic group which covalently binds to the catalytic nucleophiles, (e.g. Ser, Cys or Thr in serine, cysteine and threonine proteases respectively) located at the active site of the enzymes.

Other biosensors include for example protease substrates that produce a reactive product or are irreversible inhibitors that selectively label active enzymes. In an embodiment, the protease is a cysteine protease substrate.

Other biosensors include for example glycosyl hydrolase substrates. In an embodiment the glycosyl hydrolase substrate is a B-galactosidase substrate including for example compound 24 described herein. This B-galactosidase substrate upon substrate cleavage produces a quinone methide tellurophene labelled compound that reacts with cell components thereby labelling the cell.

In one embodiment, the reactive product is a quinone methide.

In an embodiment, the biosensor comprises a membrane targeting moiety such as a fatty acid. The fatty acid can for example comprise an aliphatic tail with at least 4 carbons, at least 6 carbons or any number of carbons between 4 and 22 carbons In an embodiment, the biosensor is a cathepsin protease substrate, such as a cathepsin S protease substrate. In an embodiment, the tellurophene tagged biosensor comprises

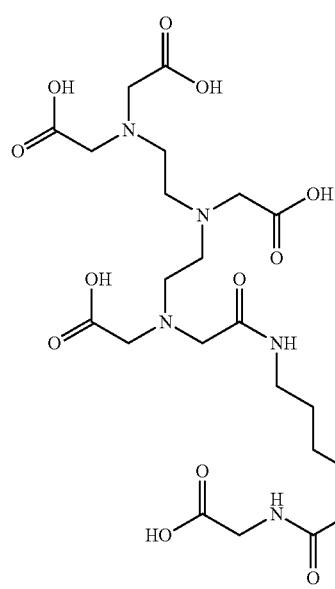
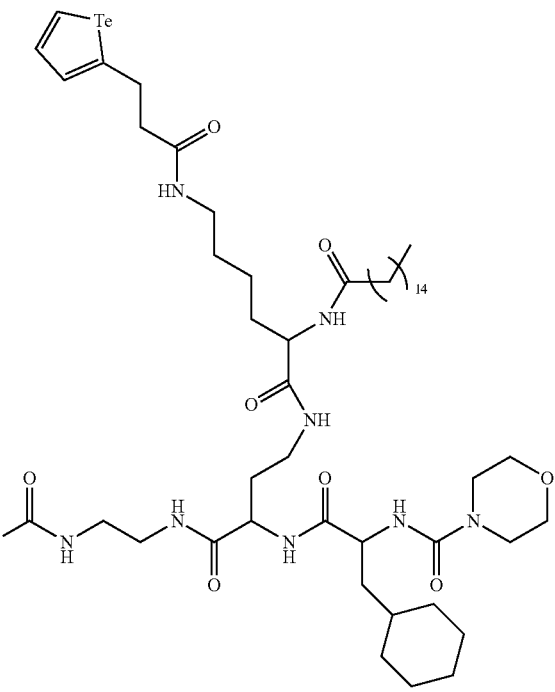

The compound is a cathepsin S peptide substrate and is membrane associated. In an embodiment, the substrate is labelled with two mass tags, optionally two organotellurophene moieties each comprising a different isotope of Te. In such an embodiment, cellular cathepsin S activity results in cleavage of the substrate and release of one of the mass tags. A ratio of the two mass tags can be calculated and is indicative of cathepsin activity.

Yet other biosensors include for example phosphatase substrates such as alkaline phosphatase substrates, as well as ATPase active site-specific reactive compounds, GTPase active site-specific reactive compounds and kinase active site-specific reactive compounds In another embodiment, Z in the compounds of formula (II) is a biologically active material.

In a further embodiment, the biologically active material is selected from a cell, virus, subcellular particle, polypeptide, nucleic acid, peptidic nucleic acid, oligosaccharide, polysaccharide, lipopolysaccharide, cellular metabolite, hapten, hormone, pharmacologically active substance, alkaloid, steroid, vitamin, amino acid and sugar.

In yet a further embodiment, the biologically active material is selected from a polypeptide, oligosaccharide, polysaccharide, lipopolysaccharide, sugar, cellular metabolite, pharmacologically active substance and amino acid.

In yet another embodiment, the biologically active material is selected from a sugar, pharmacologically active substance and amino acid.

In an embodiment, the amino acid is lysine, phenylalanine, tyrosine or tryptophan.

In another embodiment, the biologically active material is an affinity reagent selected from an antibody or binding fragment thereof, aptamer, avidin reagent, nucleic acid or lectin.

In another embodiment, the biologically active material further comprises a mass tag or a supporting structure of a mass tag, wherein the mass tag or supporting structure is optionally directly attached to the biosensor or attached through a linker, such as a linker L as defined herein.

In yet a further embodiment, the compound of formula (II) is selected from:

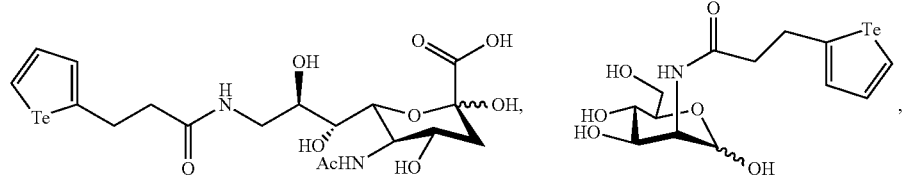

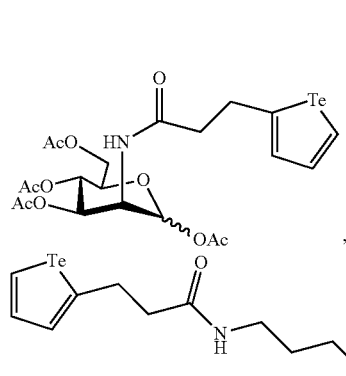
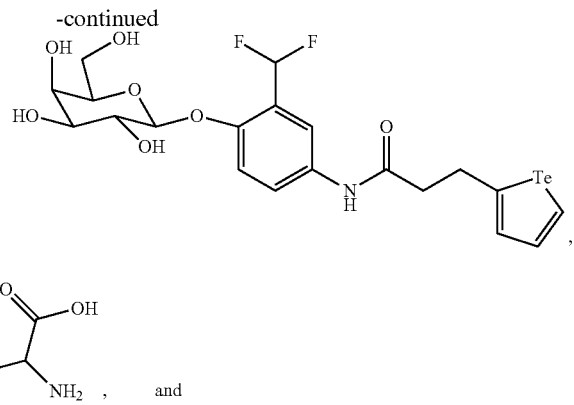

-continued

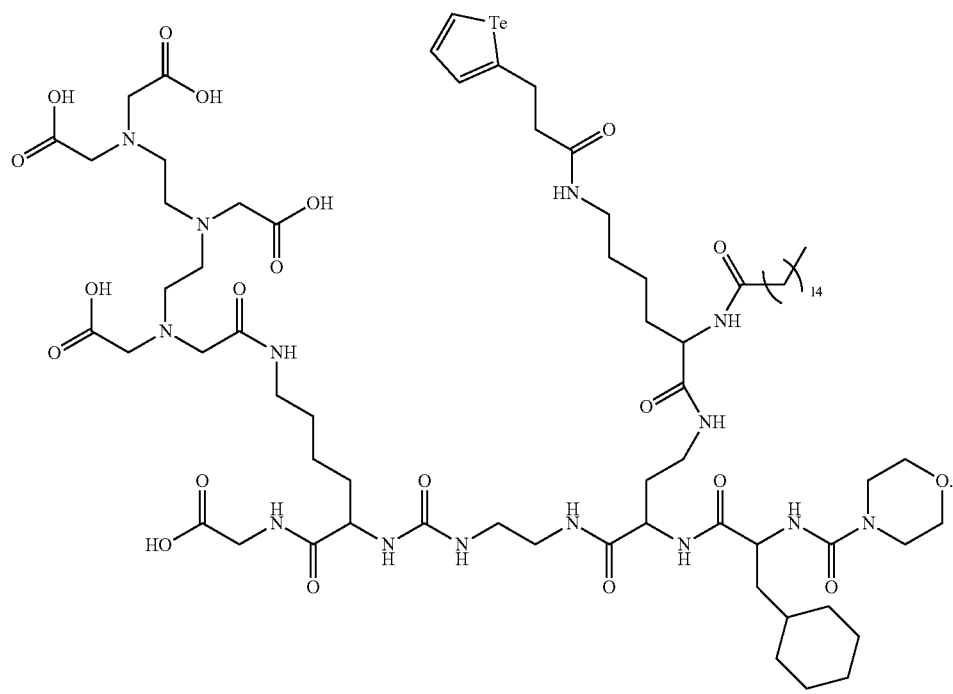

In an embodiment, Z in the compounds of formula (II) is a monomeric unit of a polymeric backbone and the compound comprises at least one of formula (IIa):

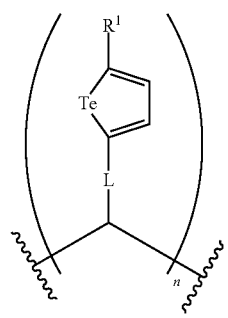

(IIa)

wherein n is an integer representing the number of repeating monomeric units of formula (IIa).

In another embodiment, the polymeric backbone further comprises monomers containing negative charges and/or side chains that improve water solubility.

In a further embodiment, the monomers that improve water solubility comprise of polyethyleneglycol units and/or zwitter ions.

In another embodiment, the polymeric backbone further comprises one or more biosensors, and/or biologically active materials, optionally directly attached or attached through a linker, such as linker L as defined herein. In another embodiment, polymeric backbone further comprises a mass tag or a supporting structure of a mass tag, wherein the mass tag or supporting structure is optionally directly attached to the biosensor or attached through a linker, such as a linker L as defined herein.

In an embodiment, the polymer backbone is one described in Lou et al, Angew. Chem Int Ed 2007 [42], or Majonis et al, Anal Chem 2010 [43], each hereby incorporated by reference.

In yet a further embodiment, the compound of formula (IIa) is selected from:

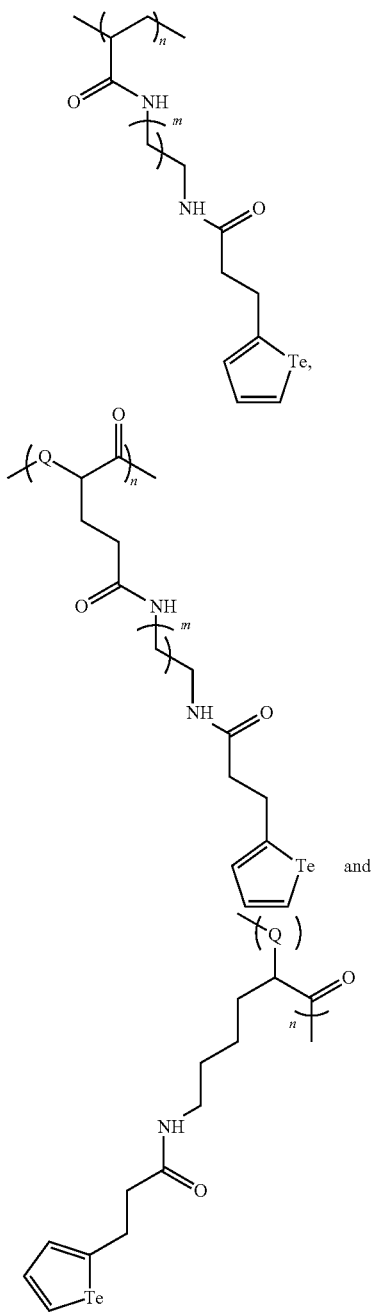

wherein Q is O or NH.

In an embodiment, a compound of formula (I), a compound of formula (II) or a compound of formula (IIa) comprise a tellurium isotope selected from $^{120}$Te, $^{122}$Te, $^{123}$Te, $^{124}$Te, $^{125}$Te, $^{126}$Te, $^{128}$Te and $^{130}$Te.

The compounds described herein can be attached to a solid support such as a bead, slide, synthetic membrane, plate, tube or column. For example, the bead can be an agarose bead or a silica bead The solid support can comprise one or more different compounds and/or a distinct tellurium mass and/or distinct tellurium isotope such that it is distinguishable from other types of solid supports by tellurium mass analysis.

The compound of formula (I) are prepared using methods known in the art from materials that are either commercially available or are also prepared using methods known in the art. For example, the compounds of formula (I) are prepared by combining a compound of formula (III), or a protected form thereof:

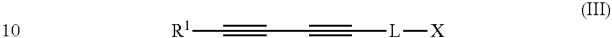

(III)

wherein $R^1$, L and X are as defined above, with an aqueous suspension of one or more naturally occurring isotopes of $Te^0$ and a basic Rongalite solution under conditions to provide the compound of formula (I). The compounds of formula (II) are prepared from the compounds of formula (I) by reacting a suitable precursor to the biosensor, biologically active material, or polymeric backbone, the suitable precursor comprising a complementary functional group to X.

The conversion of a compound of formula (I) to a compound of formula (II), is performed using methods known in the art, for example using nucleophilic addition conditions and activated acid substitution conditions. The polymeric backbone and attachments of biosensors biologically active materials, mass tags and/or mass tag supporting structures thereto are made using methods known in the art, for example, as described in U.S. Pat. No. 9,012,239, herein incorporated by reference.

The reaction conditions will depend, for example, on the identity of the reactive functional group and the biosensor, biologically active material, mass tag, supporting structure in a mass tag and/or polymeric backbone and may involve one or more presteps. For example the biologically active material may be pre-treated to activate groups that can react with the organotellurophene tag functional group and/or the organotellurophene tag may be pre-treated to activate groups that can react with the biologically active material. Further, the reactions may need to be modified to include the use of protecting groups.

Purifying the mass tagged biosensor, biologically active material and/or polymer can comprise removing unreacted starting materials and can comprise one or more steps of filtering, column purification, centrifuging and/or washing and recovering the mass tagged biosensor, biologically active material or polymer.

In an embodiment, the present application also includes compositions comprising one or more compounds selected from a compound of formula (I) and a compound of formula (II), and salts and/or solvates thereof. In an embodiment, the composition further comprises a carrier. Examples of carriers include, but are not limited to, solvents, adjuvants and excipients. In a further embodiment the composition further comprises other components, for example, for the stability, of the composition, such as antioxidants and/or antimicrobial agents. In an embodiment, the composition comprising one or more compounds of formula (II), and/or salts and/or solvates thereof, is compatible with biological systems, including cells. In an embodiment, "compatible with" means non-toxic to, or at least having a toxicity that is below acceptable levels.

In an embodiment, the compositions of the application comprise a plurality of compounds of formula (I) and/or (II) each having a different tellurium isotope.

In an embodiment, the compositions of the application comprise a plurality of compounds of formula (II), each having a different biosensor, a different biologically active material (optionally a different antibody) and/or a different polymer.

In an embodiment, the compositions of the application comprise an effective amount of one or more compounds selected from a compound of formula (I) and a compound of formula (II), and salts and/or solvates thereof.

In an embodiment, the compound or composition of the application is comprised in a vial. For example, the vial is a light blocking vial for light sensitive compounds or compositions. In an embodiment, the compounds or compositions are stored in the vial under inert atmospheric conditions, particularly for example for oxygen reactive compounds.

In an embodiment, the application includes a kit comprising a compound, composition or vial described herein and instructions or reagents for reconstituting and/or using the compound or composition in, for example, a mass detection assay. For example the kit can comprise an alkaline phosphatase substrate tagged with a tellurophene compound of formula (I). In an embodiment, the instructions are for mass tagging a biosensor, biologically active material or a polymer backbone with a compound of formula (I) or performing a mass detection assay with the mass tagged biosensor or biologically active material. In an embodiment, the mass detection assay is a mass cytometry assay.

In an embodiment, the kit is a multiplex kit and comprises at least 2, 3, 4, 5, 6, 7 or 8 compounds, each compound comprising a different tellurium isotope, different combinations of tellurium isotopes such that the compounds have a distinct tellurium mass and/or a different biosensor, a different biologically active compound and/or polymeric backbone. The kit can comprise a series of compounds which are the same compound other than the tellurium isotope or they can be different compounds comprising different tellurium epitopes. Examples include a plurality of compounds of formula (I), each compound having the same structure and comprising a different tellurium isotope. Alternatively, the compounds can be compounds of formula (II), optionally wherein the biologically active material is for example an affinity reagent, such as an antibody specific for a particular antigen, with each compound comprising a different tellurium isotope.

The compounds, compositions, and kits described herein include components and/or can be packaged for particular assays.

In an embodiment, the kit comprises a standard such as an internal standard for example a calibration bead for use in mass cytometry applications.

III. Methods and Uses

One aspect described herein includes a method of mass tagging a biosensor, biologically active material or polymer backbone or the use of an organotellurophene tag (e.g. a compound of formula (I)) for preparing a mass tagged biosensor, a mass tagged biologically active material or a mass tagged polymer.

In an embodiment, the method comprises contacting an organotellurophene tag, comprising a linker and a reactive functional group with a biosensor, biologically active material or polymeric backbone under suitable reaction conditions; and purifying the mass tagged biosensor or mass tagged biologically active material.

In an embodiment, the organotellurophene tag is a compound of formula (I).

Different biosensors, biologically active materials, and polymeric backbones are described herein and can be employed in the methods and uses described herein. Synthetic schemes for a number of compounds of formula (II) are provided below. Accordingly, in an embodiment the method of mass tagging produces a compound of formula (II). In an embodiment the method employs a synthetic scheme described herein.

In an embodiment, the method contacting step comprises contacting a biologically active material selected from a cell, virus, subcellular particle, polypeptide, nucleic acid, peptidic nucleic acid, oligosaccharide, polysaccharide lipopolysaccharide, cellular metabolite, hapten, hormone, pharmacologically active substance, alkaloid, steroid, vitamin, amino acid and sugar with the tellurophene tag under suitable conditions.

In another embodiment, the biologically active material is selected from an affinity reagent selected from an antibody or binding fragment thereof, aptamer, avidin reagent, nucleic acid or lectin. The biologically active material can be tagged to the tellurophene tag through for example a thiol of a cysteine residue or a thiol engineered into the biologically active material. Reaction of the thiol with a thiol selective reagent, for example, a maleimide will give the desired construct. Alternatively free amines on the biologically active material can be acylated by the tellurophene tag.

The compounds described herein can be used in several assays including cytometry assays that can use fluorescent markers. For example, tellurophene mass tagged compounds as described herein can be coupled to affinity reagents such as antibodies, oligonucleotides, lectins, apatamers and the like and used for detecting a target analyte, optionally in or on a cell.

In particular, the compounds can be used for multiplex labelling of cells, viruses, subcellular particles, polypeptides, nucleic acids and the like. For example, mass tagged biologically active materials, such as mass tagged affinity reagent such as antibodies can be prepared as described for a number of target analytes. In an example, each mass tagged affinity reagent is directed to a different analyte and comprises a distinct tellurium mass or is used in combination with other non-tellurium mass tagged molecules to expand the number of parameters that can be assayed. Cells can be cultured under normal conditions, labelled with a desired combination of mass tagged affinity reagents in one reaction mixture to assay multiple parameters of a single cell population. Alternatively, cells can be labelled with affinity reagents to one or more target analytes in different reaction mixtures to assay one or more test parameters, wherein each reaction mixture is a cell population treated under a different test parameter. The cells can be washed, collected, fixed, optionally stained with one or more intercalators such as a Rhodium based nucleic acid intercalator (e.g MaxPar® Intercalotor-Rh, Fluidigm) to distinguish dead from live cells and/or singly nucleated cells from other cells and analysed by mass cytometry, for example as described for Telox/Telox2 hypoxia examples described herein.

Accordingly another aspect includes a method of detecting or quantifying a target activity or target analyte comprising the steps of:

providing a cell or cell population;

providing a tellurophene tagged biosensor or biologically active material optionally a compound of formula (II), wherein the biosensor is a substrate for the target activity and/or the biologically active material specifically binds the target analyte;

mixing the cell or cell population with the tellurophene tagged biosensor or biologically active material; and detecting tellurium labelling and/or quantitating the amount of tellurium labelling of the cell or cell population.

The target analyte can for example be a cell surface or intracellular entity in a cell of the cell population. Similarly, the activity can be a cell surface or intracellular enzymatic activity. As the tags can be compact, the tags can be used to label intracellular constituents as well as extracellular antigens. Assaying the tellurium labelling of the cell population indicates whether the target analyte or activity is present and/or the amount of analyte or activity.

Assays for detecting and/or quantitating the tellurium labelling of the target analyte and/or cell population include mass based methods which can monitor the distinct tellurium mass or distinct tellurium isotope such as a mass cytometry assay.

As described herein, detecting and/or quantitating the tellurium labelling using mass cytometry involves vaporizing cells and analyzing said cells by time of flight mass spectrometry.

Mass cytometry, in addition to enabling single cell analysis can include mass cytometry imaging methods for example as described in (Giesen et al 2014, incorporated herein by reference). In such methods, a tissue or cell population is labelled in vitro with mass tagged biosensors and/or biologically active materials, the tissue or cell population is subjected to laser ablation coupled to mass cytometry and the tellurium signal processed to provide an image showing single cell segmentation. Different tissue preparations can be used including for example formalin fixed and fresh tissue.

In other embodiments, the substrate may produce an insoluble tellurium containing compound that precipitates locally. The presence of the precipitate is imaged, and can provide an indication of enzyme localization in a cell or tissue.

The detecting and/or quantitating tellurium labelling can also employ an enzyme linked assay. In enzyme linked assays, the enzyme substrate, optionally an alkaline phosphatase substrate, is tagged with a tellurophene tag. The substrate upon cleavage produces a reactive product such as a quinone methide. In the presence of enzyme, the reactive tellurium containing product would be formed and would covalently label the enzyme or other local biomolecules. Tellurium presence can be measured and is indicative of the presence and/or amount of enzyme or enzyme activity.

Different tellurophene tags each comprising distinct mass can be used to analyse a number of parameters in parallel.

In an embodiment, a tellurophene tagged biologically active material is provided. In an embodiment, the target analyte is a polypeptide and the biosensor biologically active material is a polypeptide affinity reagent optionally an antibody, aptamer avidin reagent such as streptavidin, or deglycosylated avidin.

Nucleic acid probes can also be prepared comprising a tellurophene tag. Accordingly in an embodiment, the target analyte is a nucleic acid and the biologically active material is a polynucleotide probe.

In an embodiment, a tellurophene tagged biosensor is provided.

As demonstrated herein, in addition to looking at static biomarkers, tellurophene tagged biosensors such as the ones described herein can be used advantageously to probe cellular enzymatic and/or metabolic activity. In an embodiment, the tellurium labelling is indicative of the presence or amount target activity For example, compounds comprising the hypoxia sensitive biosensor 2-nitroimidazole are described. These compounds as demonstrated herein can be used for detecting or labelling oxygen deprived cells. Telox and Telox2 as well as other 2-nitroimidizole comprising compounds are enzymatically processed and form reactive intermediates under low oxygen conditions. Said reactive intermediates form adducts thereby labeling the cells. Assaying the cells for tellurium isotopes identifies cells that exposed to low oxygen conditions.

Accordingly in an embodiment, the activity is oxidoreductase activity. In an embodiment, the method is for detecting and/or labelling oxygen deprived cells, the method comprising: incubating a population of cells with the compound of formula (II) wherein Z is a biosensor comprising 2-nitroimidazole, detecting and/or quantitating the amount of tellurium labelling in the cell population, wherein tellurium labelling is indicative of oxygen deprivation.

The population of cells can for example be in a tissue sample or can be subjected to different test conditions to assess whether hypoxia is induced. In an embodiment, the tellurium labelling is measured by mass cytometry.

In an embodiment, the method further comprises quantifying the number of oxygen deprived cells in the population.

In an embodiment, the method comprises one or more of the steps in FIG. 4 or described herein. In an embodiment, the quantitating comprises comparing to a control.

Other enzyme activities can also be measured using organotellurophene mass tagged compounds. Proteases comprise an active site that is available to substrates when the protease is active. For example, a cathepsin S substrate is described that can be used to measure cathepsin S activity, the cathepsin S substrate being

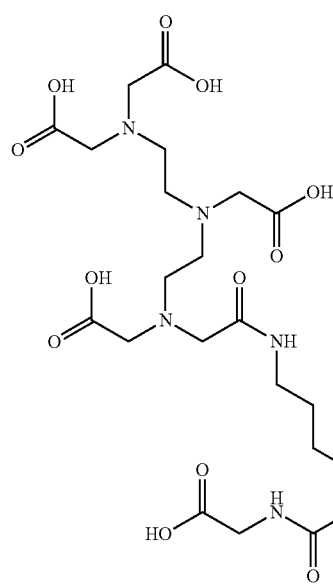
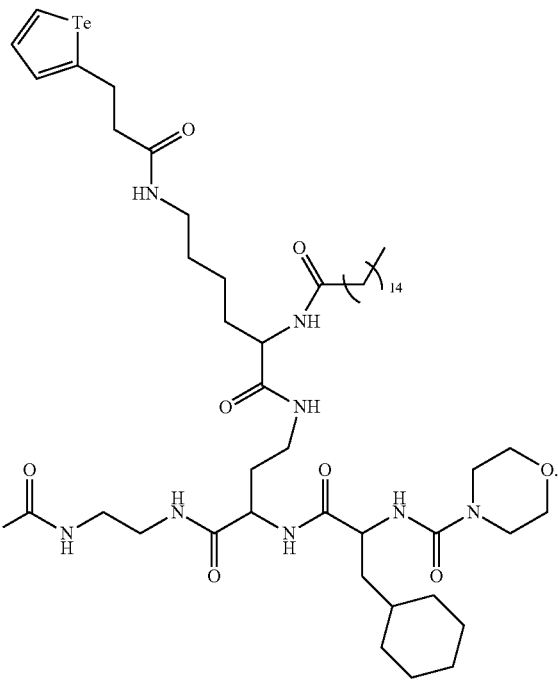

In the presence of active cathepsin, cleavage of the substrate results in production of a tellurium containing peptide (tellurium isotope 1) which is localized to the membrane. A second isotope (or other metal tag, optionally a lanthanide) can be bound to the DTPA portion of the molecule, and is released as a soluble entity after protease cleavage. The ratio of tellurium isotope 1 to the other isotope (or other metal tag) can be used to quantify the level of cathepsin activity.

Accordingly, in an embodiment, the activity is protease activity. In another embodiment, the activity is cathepsin S activity.

In another embodiment, the activity is glycosylhydrolase activity. Described herein is a B-galactosidase tellurophene tagged substrate (compound 24). Upon cleavage by B-galactosidase a quinone methide is produced. Cells that comprise active B-galactosidase are labelled and can be detected by for example mass cytometry methods.

B-galactosidase or LacZ is used in a number of applications. Different tellurophene isotopes alone or in combination with other metal tags can for example be used to assess the B-galactosidase activity of a series of clones.

In another embodiment, the activity is a phosphatase activity, kinase activity or lipase activity. In an embodiment, the phosphatase activity is alkaline phosphatase.

In an embodiment, the biosensor is selected from 2-nitroimidazole, oxidoreductase substrate, protease substrate, phosphatase substrate, kinase substrate, glycosyl hydrolase substrate or lipase substrate.

Amino acids such as lysine, phenylalanine, tyrosine and tryptophan can also be mass tagged. In addition, nucleotides, sugars can also be mass tagged. Such organotellurophene tagged reagents can be used for metabolic labelling. In an embodiment, the method comprises incubating a population of cells in media wherein a natural molecular building block is replaced with a mass tagged analog, the incubation being under conditions and for sufficient time for target analyte biomolecule synthesis, for example to allow incorporation of the mass tagged analog into the biomolecule target analyte, detecting and/or measuring the tellurium labelling of the cell population and/or target analyte by for example mass cytometry.

In some embodiments, a plurality of target analytes and/or target activities are detected and/or quantified and the method comprises providing a plurality of tellurophene tagged biosensors and/or biologically active materials, optionally a plurality of compounds of formula (II), wherein each compound comprises a different biosensor or different biologically active material, optionally an affinity reagent and a different tellurium isotope, thereby allowing multiplexing.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Abbreviations and Definitions
CDCl$_3$=deuterated chloroform; DART MS=direct analysis in real time mass spectrometry; DCC=N,N'-dicyclohexylcarbodiimide; DCU=dicyclourea; DCM=dichloro methane; DME=dimethyl ethane; DMSO=dimethyl sulphoxide; ESI=electrospray ionization; EtOAc=ethyl acetate; FBS=fetal bovine serum; HPLC=high performance liquid chromatography; LC-MS=liquid chromatography mass spectrometry; MC=mass cytometry; NHS=N-hydroxysuccinimide; NMR=nuclear magnetic resonance; O.N=over night; PBS: phosphate buffered saline; p-NP=para-nitrophenol; ppm=parts per million; RPMI=Roswell Park Memorial Institute; THF=tetrahydrofuran; TLC=thin layer chromatography; WST-1=water soluble tetrazolium salt 1

Methods

Instrumentation:

Rotary evaporation was performed using a Heidolph rotary evaporator. All NMR spectra were recorded at 25° C. on one of the following spectrometers: Agilent DD2 600 MHz (with OneNMR H/F{X} probe), Agilent DD2 500 MHz (with Xsens cold probe), or a Varian 400 MHz (with AutoX probe). One-dimensional proton and carbon chemical shifts are reported in parts per million and referenced to residual proton signals of NMR solvents (CD3OD; δ 3.31 ppm, CDCl3; 7.26 ppm). All coupling constants are reported in hertz (Hz) and protons multiplicities are described as either s=singlet, d=doublet, dd=doublet of doublets, t=triplet, q=quartet, p=pentet, or m=multiplet. NMR data is reported in the following order/format; chemical shift (multiplicity, integration, coupling constant, assignment). High-resolution mass spectra were recorded using a JEOL AccuTOF mass spectrometer with a direct analysis in real time (DART) ionization source. ICP-MS data was obtained using a PerkinElmer ELAN-9000 spectrometer. Mass cytometry data was obtained using a second-generation CyTOF (DVS Sciences/Fluidigm). UV-Vis spectroscopy data was recorded using an Agilent ultraviolet-visible photospectrometer (model #8453).

High resolution mass spectrometry was obtained by one of the following: JEOL AccuTOF model JMS-T1000LC mass spectrometer equipped with DART ion source or Agilent 6538 Q-TOF mass spectrometer equipped with Agilent 1200 HPLC and an ESI ion source.

Reagents and General Conditions:

Solvents were removed under vacuum at approximately 40° C. All reactions were performed under inert atmosphere using N₂ gas. Dry THF (Acros Organics), methanol (Acros Organics), pyridine (Acros Organics), ethylenediamine (Alfa Aesar), and all other reagents (Sigma-Aldrich) were used as supplied.

Example 1

Synthesis of N-(2-aminoethyl)-2-(2-nitro-1H-imidazol-1-yl)acetamide

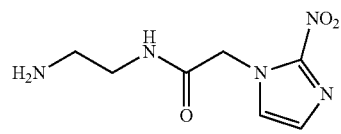 [SMILES: NCCNC(=O)Cn1ccnc1[N+](=O)[O-]]

An oven-dried 50 mL round bottom flask was charged with a solution of methyl 2-(2-nitro-1H-imidazol-1-yl)acetate[40] (500 mg, 2.7 mmol) in methanol (4.72 mL) and a magnetic stir bar. Ethylenediamine (0.722 mL, 10.8 mmol) was added dropwise to this solution over 1 minute and the mixture was allowed to stir at room temperature for 18 hours. Solvent was then removed via rotary evaporation and the resultant solid was dried under vacuum for 2 days to afford 3 (575 mg, ~quantitative) as an amorphous pale yellow solid. $^1$H NMR (500 MHz, MeOD): δ 7.45 (d, 1H, J=1.2 Hz, Ar), 7.17 (d, 1H, J=1.2 Hz, Ar), 5.17 (s, 2H, Ar—CH₂—CO—), 3.31 (t, 2H, J=6.2 Hz, —CH2-CH₂—NHCO—+residual MeOD overlap), 2.75 (t, 2H, J=6.2 Hz, H₂N—CH₂—CH₂—); $^{13}$C NMR (125 MHz, MeOD): δ 167.00, 128.00, 126.97, 51.48, 41.74, 40.47. HRMS m/z calcd. for $C_7H_{12}N_5O_3$ (MH⁺) 214.0940, found 214.0937.

Example 2

Synthesis of Compounds 1-5

Scheme 1. The synthesis of compounds 1-5. The yields of the following reactions are as follows: 1 = 66%, 2 = 74%, 3 = 85%, 4 = 91% and 5 = 50%.

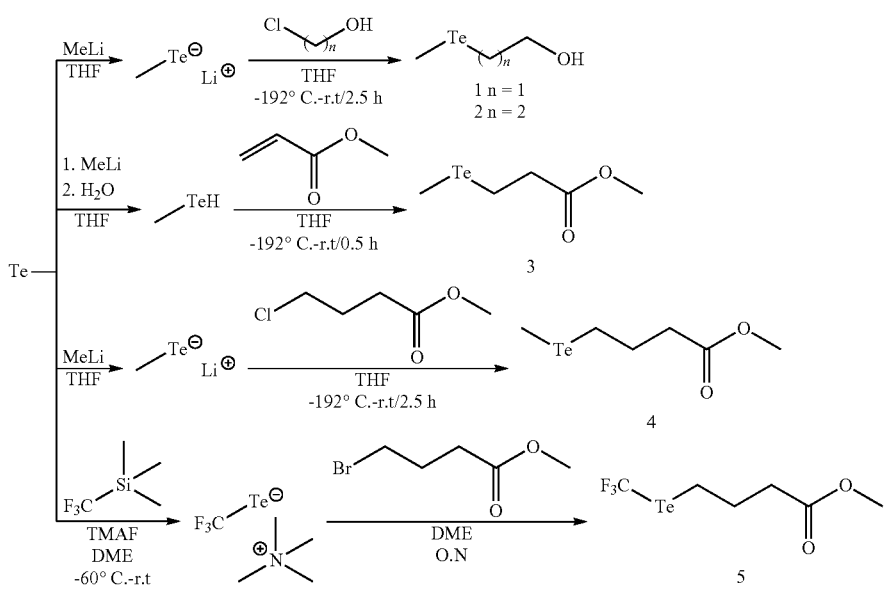

3-methyltellanyl-1-ethanol (1): Tellurium metal (granular,−5-+50 mesh, 500 mg, 3.9 mmol) was grounded to a fine powder using a mortar and pestle and suspended in THF (50 mL). Methyl lithium (2.5 mL, 4.0 mmol) was added drop-wise to the suspension until the solution became a homogenous yellow solution at room temperature. The resulting mixture was cooled to −196° C. in a liquid nitrogen bath. Upon freezing, 2-chloro-ethanol (0.261 mL, 3.9 mmol) was added in one portion and the reaction was warmed to room temperature. The reaction mixture was stirred at room temperature for 2.5 hours. Once the reaction was complete by TLC, sat. NH$_4$Cl (100 mL) was added to the mixture. The solution was extracted into diethyl ether (2×100 mL). The combined organic layer was washed with brine (1×100 mL), dried over MgSO$_4$, filtered and concentrated. The crude compound was purified by column chromatography on silica gel (10% EtOAc in Pentane) and dried under vacuum to give a viscous yellow oil. Yield: 66%, 488 mgs. $^1$H NMR (500 MHz, CDCl$_3$, δ): 3.78 (s, —CH$_2$OH, 2H), 2.80 (t, J=6.8 Hz, —CH$_2$CH$_2$OH, 2H), 1.88 (s, —TeCH$_3$, 3H); $^{13}$C NMR (125 MHz, CDCl$_3$, δ): 62.59 (—CH$_2$OH), 8.40 (—CH$_2$—Te), −22.41 (—Te—CH$_3$). [M+NH$_4$]$^+$=207.99829.

3-methyltellanyl-1-propanol (2): Tellurium metal (granular,−5-+50 mesh, 500 mg, 3.9 mmol) was ground to a fine powder using a mortar and pestle and suspended in THF (50 mL). Methyl lithium (2.5 mL, 4.0 mmol) was added drop-wise to the suspension until the solution turned yellow at room temperature. The resulting mixture was cooled to −196° C. in a liquid nitrogen bath. Upon freezing, 1-chloro-3-propanol (0.326 mL, 3.9 mmol) was added in one portion and the reaction was warmed to room temperature. The reaction mixture was stirred at room temperature for 2.5 hours. Once the reaction was complete by TLC, sat. NH$_4$Cl (100 mL) was added to the mixture. The solution was extracted into diethyl ether (2×100 mL). The combined organic layer was washed with brine (1×100 mL), dried over MgSO$_4$, filtered, concentrated and dried under vacuum to give a viscous dark orange oil product. Yield: 74%, 581 mgs. Characterization equivalent to that of literature. *Angew. Chem. Int. Ed. Engl.*, 2014, 53, 11473-11477.

methyl 3-methyltellanyl-propionate (3): Tellurium metal (granular,−5-+50 mesh, 500 mg, 3.9 mmol) was ground to a fine powder using a mortar and pestle and suspended in THF (50 mL). Methyl lithium (2.5 mL, 4.0 mmol) was added drop-wise to the suspension until the solution turned yellow at room temperature. Water (0.18 mL) was added to the solution, inducing a color change to a dark brown mixture. The resulting mixture was cooled to −196° C. in a liquid nitrogen bath. Upon freezing, methyl acrylate (0.355 mL, 3.9 mmol) was added in one portion and the reaction was warmed to room temperature. The reaction mixture was stirred at room temperature for 0.5 hours. Once the reaction was complete by TLC, sat. NH$_4$Cl (100 mL) was added to the mixture. The solution was extracted into diethyl ether (2×100 mL). The combined organic layer was washed with brine (1×100 mL), dried over MgSO$_4$, filtered, concentrated and dried under vacuum to give a viscous dark yellow oil. Yield: 85%, 775 mgs. $^1$H NMR (500 MHz, CDCl$_3$, δ): 3.68 (s, —COOCH$_3$, 3H), 2.86 (m,—CH$_2$COOCH$_3$, 2H), 2.76 (m,—CH$_2$CH$_2$Te—, 2H), 1.92 (s, —Te—CH$_3$, 3H); $^{13}$C NMR (125 MHz, CDCl$_3$, δ): 173.87 (C=O), 52.11 (—COOCH$_3$), 37.17 (—CH$_2$COOCH$_3$), −4.72 (—TeCH$_2$CH$_2$—), −21.35 (—Te—CH$_3$). [M+H]$^+$=232.98149.

methyl 4-methyltellanyl-butanoate (4): Tellurium metal (granular,−5-+50 mesh, 500 mg, 3.9 mmol) was ground to a fine powder using a mortar and pestle and suspended in THF (50 mL). Methyl lithium (2.5 mL, 4.0 mmol) was added drop-wise to the suspension until the solution turned yellow at room temperature. The resulting mixture was cooled to −196° C. in a liquid nitrogen bath. Upon freezing, methyl-4-chlorobutyrate (0.478 mL, 3.9 mmol) was added in one portion and the reaction was warmed to room temperature. The reaction mixture was stirred at room temperature for 2.5 hours. Once the reaction was complete by TLC, sat. NH$_4$Cl (100 mL) was added to the mixture. The solution was extracted into diethyl ether (2×100 mL). The combined organic layer was washed with brine (1×100 mL), dried over MgSO$_4$, filtered, concentrated and dried under vacuum to give a viscous dark yellow oil. Yield: 91%, 877 mgs. $^1$H NMR (500 MHz, CDCl$_3$, δ): 3.64 (s, —COOCH$_3$, 3H), 2.60 (t, J=7.6 Hz, —TeCH$_2$— 2H), 2.39 (t, J=7.4 Hz, —CH$_2$COOCH$_3$, 2H), 2.01 (m, —CH$_2$CH$_2$CH$_2$—, 2H), 1.86 (s, —TeCH$_3$, 3H); $^{13}$C NMR (125 MHz, CDCl$_3$, δ): 173.09 (C=O), 51.36 (—COOCH$_3$), 35.71 (—CH$_2$C=O—), 26.76 (—CH$_2$CH$_2$C=O—), 1.92 (—TeCH$_2$CH$_2$—), −22.52 (—TeCH$_3$). [M+H]$^+$=246.99690.

methyl 4-((trifluoromethyl)tellanyl)butanoate (5): Tellurium metal (granular,−5-+50 mesh, 500 mg, 3.9 mmol) was ground to a fine powder using a mortar and pestle and suspended in 7 mL of DME. The solution was cooled to −60° C. using a 40% ethylene glycol 60% ethanol and dry ice cooling bath. Upon cooling, trimethyl(trifluoromethyl)silane (0.356 mL, 2.61 mmol) and tetramethylammonium fluoride (243 mg, 2.61 mmol) were added to the reaction mixture. The reaction was stirred vigorously for 1 hour at −60° C. and for 3 hours at room temperature. Once the reaction was complete, the yellow supernatant was decanted off and the solid residues remaining were washed with DME. The supernatant and the washes were combined and concentrated. To the concentrated crude mixture, 3 mL of DME and methyl 4-bromobutyrate (0.230 mL, 1.82 mmol) were added. The reaction mixture was stirred over-night at room temperature. Once the reaction was complete, the DME was removed by rotary-vaporization and the remaining crude mixture was taken up in EtOAc. This organic layer was washed with water (3×), brine (1×), dried over MgSO$_4$, filtered and concentrated. The crude mixture was purified by column chromatography (Toluene on silica gel). Yield: 50%, 270 mgs. $^1$H NMR (500 MHz, CDCl$_3$, δ): 3.68 (s, —COOCH$_3$, 3H), 3.13 (t, J=7.7 Hz, —TeCH$_2$—, 2H), 2.47 (t, J=7.7 Hz, —CH$_2$COOCH$_3$, −2H), 2.26 (p, J=7.1 Hz, —CH$_2$CH$_2$CH$_2$—, 2H); $^{13}$C NMR (125 MHz, CDCl$_3$, δ): 172.82 (C=O), 103.79-95.40 (q, J=351.5 Hz, —Te—CF$_3$), 51.763 (—COOCH$_3$), 35.41 (—CH$_2$CH$_2$CH$_2$Te—), 27.08 (—CH$_2$CH$_2$CH$_2$—), 8.20 (—TeCH$_2$—). [M+NH$_4$]$^+$=317.99529.

Example 3

Synthesis of Compounds 6 and 7

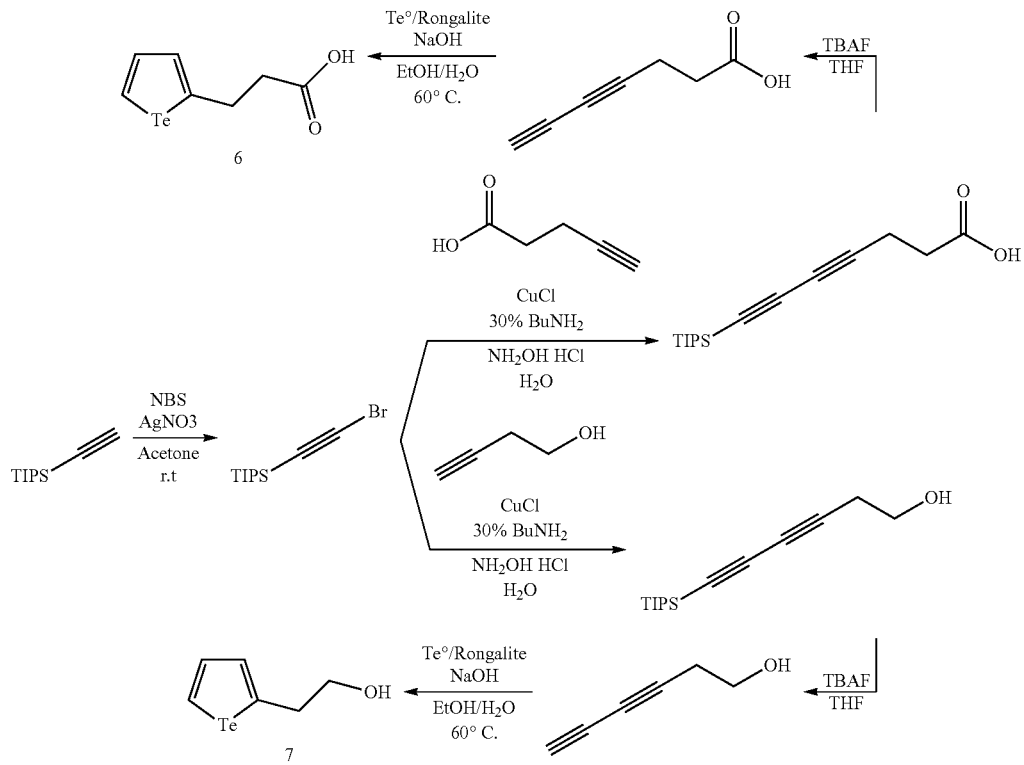

Scheme 2. The synthesis of compounds 6 & 7. The yields of the reactions: 6 = 70% & 7 = 66%.

1-(bromoethynyl)triisopropylsilane: N-bromosuccinimide (5.15 g, 29 mmol), silver nitrate (4.28 g, 25.2 mmol) and TIPS-acetylene (5.6 mL, 25.2 mmol) were added to 200 mL of acetone. The solution mixture was stirred vigorously for 3 hours at room temperature. Once the reaction was complete, 150 mL of water was added to the mixture. The solution was extracted into hexane (3×125 mL). The combined organic layer was washed with brine (2×), dried over MgSO$_4$, filtered, concentrated and dried under vacuum to give a clear oil product. Yield: 6.51 g, 98%. Ref: *Org. Lett.* 2011, 13, 537-539.

hepta-4,6-diynoic acid intermediates: Cadiot-Chodkiewics coupling was completed according to literature. (J. P. Marino, H. N. Nguyen, *J. Org. Chem.,* 2002, 67, 6841-6844.) CuCl (15 mg, 0.15 mmol) was added to an aqueous solution of 30% BuNH$_2$ (25 mL) at room temperature which generated a transparent blue solution. A few hydroxylamine hydrochloride crystals were added to this solution mixture to discharge the color. 4-pentynoic acid (901 mg, 9.2 mmol) was added to the mixture at once, resulting in a yellow suspension. This solution was cooled using an ice-water bath. Upon cooling, 2-bromo-1-triisopropylsilyl acetylene (2 g, 7.6 mmol) was added drop-wise. Additional crystals of hydroxylamine hydrochloride were added to maintain the yellow solution when blue-green color changes occurred. The reaction was stirred vigorously for 0.5 hours. Once the reaction was complete by TLC, the solution was extracted with EtOAc (2×100 mL). The combined organic layer was washed with 1M HCl (1×100 mL), brine (1×100 mL), dried with MgSO$_4$, filtered, concentrated and dried under vacuum to give a dark brown crude crystalline product (1.6 g, 76%). The crude product of 6-(triisopropylsilyl)hepta-4,6-diynoic acid (388 mg, 1.39 mmol) was dissolved in THF (15 mL). This solution mixture was cooled using an ice-water bath. While cooling, tetrabutylammonium fluoride (1.39 mL, 1M in THF) was added dropwise until the solution reached room temperature. The reaction was stirred vigorously for 3 hours. Once the reaction was complete, the solution was extracted with EtOAc (3×100 mL). The combined organic layer was washed with 1M citric acid (3×100 mL), brine (3×100 mL), dried with MgSO$_4$, filtered, and dried under vacuum to give a brown crude oil product. The compound was taken directly to the next step of 2-(tellurophene-2-yl) propanoic acid synthesis.

2-(tellurophen-2-yl)propanoic acid (6): Tellurium metal (granular,–5-+50 mesh, 3.0 g, 12.68 mmol) was ground to a fine powder using a mortar and pestle. The tellurium powder was added to an aqueous solution of 1M NaOH (30 mL). To the reaction mixture, sodium hydroxymethylsulfinate (6.0 g, 21.18 mmol) was added and stirred vigorously. The reaction solution was heated using an oil bath, to 95° C. for 0.5 hours and the solution turned a deep purple color. The reaction solution was cooled to 60° C. and stirred for an additional 5 mins. In 5 mL of ethanol, hepta-4,6-diynoic acid (388 mg, 3.17 mmol) was added to the reaction mixture. This solution mixture was stirred for 1.5 hours at 60° C. The reaction was then exposed to oxygen by removing the septa and allowing in atmosphere. The reaction was allowed to cool to room temperature and stirred for 15 mins. Upon cooling, the reaction was diluted with a sat. NH$_4$Cl solution (100 mL). The solution was extracted with EtOAc (2×100 mL). The combined organic layer was washed with 1M HCl (2×100 mL), brine (2×100 mL), dried over MgSO$_4$, filtered, concentrated, and dried under vacuum to give a dark yellow solid crude product. The crude product was purified by flash chromatography (5%-50% EtOAc/Hexanes on silica gel) to give a light yellow solid (563 mg, 70%). $^1$H NMR (500 MHz, CDCl$_3$, δ): 8.71 (dd, J=6.9, 1.2 Hz, —HCTe—, 1H), 7.59 (m, —HCHCTe—, 1H), 7.38 (m, —TeCCH—, 1H), 3.22 (t, J=7.3, Tephene-CH$_2$—, 2H), 2.73 (t, J=7.3, —CH$_2$CH$_2$COOH, 2H); $^{13}$C NMR (125 MHz, CDCl$_3$, δ): 178.94 (C=O), 148.69 (—TeCCH—), 137.42 (—HCHCTe—), 136.15 (—TeCCH—), 125.29 (—HCTe—), 37.95 (Tephene-CH$_2$—), 32.01 (—CH$_2$CH$_2$COOH). [M+H]$^+$=254.96665.

hexa-3,5-diyn-1-ol intermediate: Cadiot-Chodkiewics coupling. CuCl (7.5 mg, 0.08 mmol) was added to an aqueous solution of 30% BuNH$_2$ (25 mL) at room temperature that generated a transparent blue solution. A few hydroxylamine hydrochloride crystals were added to this solution mixture to discharge the color. 3-Butyn-1-ol (1 g, 3.83 mmol) was added to the mixture resulting in a yellow suspension. This solution was cooled using an ice-water bath. Upon cooling, 2-bromo-1-triisopropylsilyl acetylene (832 mg, 3.19 mmol) was added drop-wise. Additional crystals of hydroxylamine hydrochloride were added to prevent the solution from turning a blue-green color. The reaction was stirred vigorously for 0.5 hours. Once the reaction was complete by TLC, the solution was extracted with EtOAc (2×100 mL). The combined organic layer was washed with 1M HCl (1×100 mL), brine (1×100 mL), dried with MgSO4, filtered, concentrated and dried under vacuum to give a neat dark brown oil.

This product was directly deprotected to produce 2-(tellurophen-2yl)ethan-ol. The product, 6-(triisopropylsilyl) hexa-3,5-diyn-1-ol (873 mg, 1.44 mmol) was dissolved in THF (15 mL). This solution mixture was cooled using an ice-water (1:1) bath. Upon cooling, tetrabutylammonium fluoride (1.44 mL, 1M in THF) was added dropwise and the solution was allowed to warm to room temperature. The reaction was stirred vigorously for 3 hours. Once the reaction was complete by TLC, the solution was extracted with EtOAc (3×100 mL). The combined organic layer was washed with 1 M citric acid (3×100 mL), brine (3×100 mL), dried with MgSO$_4$, filtered, concentrated and dried under vacuum to give a brown oil. This crude product was immediately taken to the next step for the synthesis of 2-(tellurophen-2yl)ethan-ol since the compound possess limited stability as a free diacetylene.

2-(tellurophen-2-yl)ethan-ol (7): Tellurium metal (granular,–5-+50 mesh, 3.2 g, 41.96 mmol) was ground to a fine powder using a mortar and pestle. The tellurium powder was added to an aqueous solution of 1M NaOH (30 mL). To the reaction mixture, sodium hydroxymethylsulfinate (6.4 g, 42.47 mmol) was added and stirred vigorously. The reaction solution was heated using an oil bath, to 95° C. for 0.5 hours and the solution turned a deep purple color. The reaction solution was cooled to 60° C. and stirred for an additional 5 mins. In ethanol (5 mL), hexa-3,5-diyn-1-ol (600 mg, 6.37 mmol) was added to the reaction mixture. This solution mixture was stirred for 1.5 hours at 60° C. At this point, the reaction was exposed to oxygen by removing the septa and exposing the reaction to atmosphere. The reaction was cooled to room temperature and allowed to stir for 15 mins. Upon cooling, the reaction was diluted with a sat. NH$_4$Cl solution (100 mL). The solution was extracted with EtOAc (2×100 mL). The combined organic layer was washed with 1M HCl (2×100 mL), brine (2×100 mL), dried with MgSO$_4$, filtered concentrated, and dried under vacuum to give a dark yellow oil crude product. The crude product was purified by flash chromatography (10%-30% EtOAc/Hexanes on silica gel stationary phase) to give a light yellow oil (949 mg, 66%). $^1$H NMR (400 MHz, CDCl$_3$, δ): 8.71 (dd, J=6.9, 1.2 Hz, —HCTe—, 1H), 7.65 (m, —HCHCTe—, 1H), 7.44 (m, —TeCCH—, 1H), 3.82 (t, J=6.0 Hz, Tephene-CH$_2$—, 2H), 3.13 (t, J=6.4 Hz, —CH$_2$CH$_2$OH, 2H), 2.68 (s, —OH, 1H). $^{13}$C NMR (100 MHz, CDCl$_3$): 145.37 (—TeCCH—), 136.34 (—HCHCTe—), 135.48 (—TeCCH—), 124.89 (—HCTe—), 63.64 (—CH$_2$CH$_2$OH), 38.85 (-Tephene-CH$_2$—). [M+H]$^+$=254.96665

Example 4

Carbamylation of Compound 2 with Benzylamine

Scheme 3. Carbamylation of compound 2 with benzylamine. 77% yield over 2 steps.

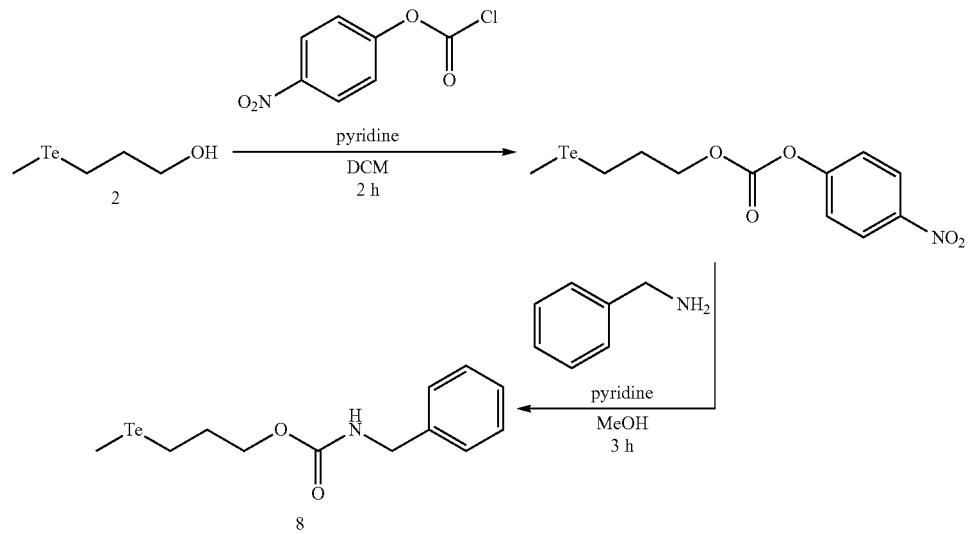

Example 5

Amidation of Compounds 4-6 with Benzylamine

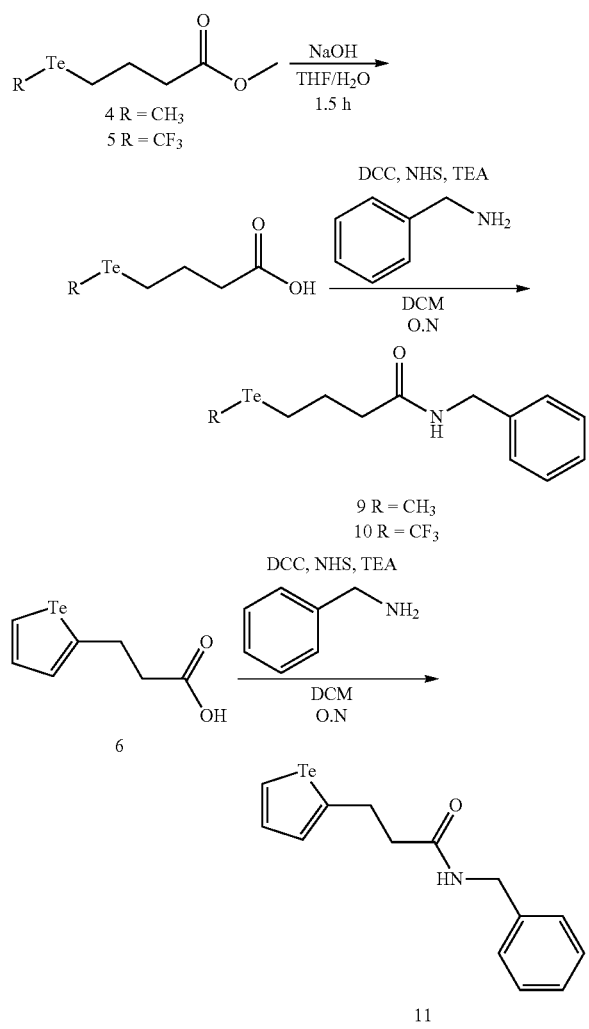

Scheme 4. Amidation of compounds 4-6 with with benzylamine. The yields of the reactions 9 = 81%, 10 = 30%, & 11 = 81%.

N-benzyl-4-(methyltellanyl)butanamide (9): Compound 4 (400 mg, 1.64 mmol) was dissolved in THF (25 mL) and stirred vigorously. To the mixture, 1 M NaOH (25 mL) was added and a biphasic mixture was generated. This solution was stirred for 1 hour. The reaction was then diluted with $H_2O$ (50 mL) and 1 M citric acid was added until the reaction mixture was acidic by pH paper. The resulting mixture was extracted into diethyl ether (3×100 mL) and washed with brine (2×100 mL). The solvent was removed from the combined organic layers by rotary evaporation. This compound was re-dissolved in DCM (5 mL) and added to a new round bottom flask where DCC (355 mg, 1.72 mmol) was added and stirred for 5 minutes. Once the mixture became a milky solution, NHS (198.2 mg, 1.72 mmol) was added to the mixture and stirred for an additional 5 minutes. To this resulting solution, a mixture of benzylamine (215 µL, 1.97 mmol) and TEA (275 µL, 1.97 mmol) in DCM (5 mL) were added at room temperature. The reaction was stirred overnight. Once the reaction was complete by TLC, the stir bar was removed and the solvent was removed by rotary evaporation. The resulting product was re-dissolved in cold EtOAc (100 mL) where white precipitate formed in the solution. The precipitate, presumed to be DCU, was removed by filtration. This process was repeated 3 times to remove the DCU. The filtrate was washed with 0.5 M citric acid (2×100 mL), $NaHCO_3$ (2×100 mL) and brine (1×100 mL). The organic layers were combined, dried with $MgSO_4$, filtered, concentrated and dried under vacuum to give a light yellow solid product (440 mg, 81%). $^1H$ NMR (500 MHz, $CDCl_3$, δ): 7.33 (m, aryl-, 5H), 5.92 (s, —NH-1H), 4.40 (d, J=5.8 Hz, aryl-$CH_2$NH— 2H), 2.62 (t, J=7.4 Hz, —Te$CH_2$—, 2H), 2.29 (t, J=7.3 Hz, —CO$CH_2$$CH_2$$CH_2$Te—, 2H), 2.06 (m, —CO$CH_2$$CH_2$$CH_2$Te—, 2H), 1.86 (s, —Te$CH_3$, 3H). $^{13}C$ NMR (125 MHz, $CDCl_3$, δ): 172.25 (C=O), (138.63, 129.08, 128.17 & 127.89, aryl), 43.99 (aryl-$CH_2$—NH—), 38.66 (—$CH_2$$CH_2$$CH_2$Te—), 27.78 (—$CH_2$$CH_2$$CH_2$Te—), 2.90 (—$CH_2$Te$CH_3$), −21.95 (—Te$CH_3$). $[M+H]^+$=322.04378.

N-benzyl-4-((trifluoromethyl)tellanyl)butamide (10): Compound 5 (400 mg, 1.4 mmol) was dissolved in 25 mL of THF and stirred vigorously. To the mixture, 25 mL of 1 M NaOH was added and a biphasic mixture was generated. This solution was stirred for 1 hour. Upon completion, the reaction was diluted and 1 M citric acid was added until the reaction mixture was acidic. The resulting mixture was extracted into ethyl acetate (3×100 mL) and washed with brine (2×100 mL). The combined organic layers were combined and the solvent was removed by rotary evaporation. This compound was re-dissolved in DCM (5 mL) and added to a new round bottom flask where DCC (303 mg, 1.47 mmol) was added and stirred for 5 minutes. Once the mixture became a milky solution, NHS (169 mg, 1.47 mmol) was added to the mixture and stirred for an addition 5 minutes. To this resulting solution, a mixture of benzylamine (180 µL, 1.68 mmol) and TEA (235 µL, 1.68 mmol) in 5 mL of DCM was added at room temperature. The reaction was stirred overnight. Upon completion, the stir bar was removed and the solvent was removed by rotary evaporation. The resulting product was redissolved in cold EtOAc (100 mL) where white precipitate formed. The precipitate, presumed to be DCU, was removed by filtration. The filtrate was washed with 0.5 M citric acid (2×100 mL), $NaHCO_3$ (2×100 mL) and brine (1×100 mL). The organic layers were combined, dried with $MgSO_4$, filtered, concentrated and dried under vacuum to give a yellow solid product (157 mg, 30%). $^1H$ NMR (500 MHz, $CDCl_3$, δ): 7.33 (m, aryl-, 5H), 5.79 (s, —NH—, 1H), 4.41 (d, J=5.7 Hz, aryl-$CH_2$NH—, 2H), 3.14 (t, J=6.9 Hz, —$CH_2$Te—, 2H), 2.34 (m, —$CH_2$$CH_2$$CH_2$Te—, 2H), 2.28 (p, J=6.8, —$CH_2$$CH_2$$CH_2$Te—, 2H). $^{13}C$ NMR (125 MHz, $CDCl_3$, δ): 171.87 (C=O), (138.40, 129.19, 128.26 & 128.07, aryl), (104.84-96.44, —$CF_3$), 44.15 (aryl-$CH_2$—NH—), 37.94 (—$CH_2$$CH_2$$CH_2$Te—), 27.75 (—$CH_2$$CH_2$$CH_2$Te—), 9.05 (—$CH_2$$CH_2$$CH_2$Te—). $[M+H]^+$=376.0175.

N-benzyl-3-(tellurophen-2-yl)propanamide (11): Compound 6 (100 mg, 0.4 mmol) was dissolved in dissolved in DCM (5 mL) and DCC (86 mg, 0.42 mmol) was added and stirred for 5 minutes. Once the mixture became a milky solution, NHS (48 mg, 0.42 mmol) was added and stirred for an addition 5 minutes. To this resulting solution, a mixture of benzylamine (52 µL, 0.48 mmol) and TEA (67 µL, 0.48 mmol) in 5 mL of DCM was added at room temperature. The reaction was stirred overnight. Upon completion, the stir bar was removed and the solvent was removed by rotary evaporation. The resulting product was redissolved in cold EtOAc (150 mL) where white precipitate crashed out of solution. The precipitate, presumed to be DCU, was removed by filtration and the filtrate was washed with 0.5 M citric acid (2×150 mL), NaHCO₃ (2×150 mL) and brine (1×150 mL). The organic layers were combined, dried with MgSO₄, filtered, concentrated and dried under vacuum to give a yellow solid. The product was purified by flash chromatography (5%-25% EtOAc/Hexanes) to give a yellow solid (440 mg, 81%). ¹H NMR (500 MHz, CDCl₃, δ): 8.71 (dd, J=6.9, 1.3 Hz, —HCTe—, 1H), 7.57 (m, —HCHCTe—, 1H), 7.31 (m, —TeCCH— & aryl, 7H), 5.76 (s, —NH—, 1H), 4.41 (d, J=5.7 Hz, aryl-CH₂NH—, 2H), 3.25 (t, J=7.6 Hz, Tephene-CH₂CH₂—, 2H), 2.53 (t, J=7.6 Hz, Tephene-CH₂CH₂—, 2H). ¹³C NMR (125 MHz, CDCl₃, δ): 171.31 (C=O), 148.96 (—TeCCH—), 137.85 (—HCHCTe—), 136.73 (—TeCCH—), (135.54, 128.84, 128.56, 127.7, 127.39 & 124.87, aryl), 43.58 (aryl-CH₂NH—), 39.88 (Tephene-CH₂CH₂—), 32.33 (Tephene-CH₂CH₂—). [M+H]⁺= 344.02941

Example 6

2-(tellurophen-2yl)methanol (12)

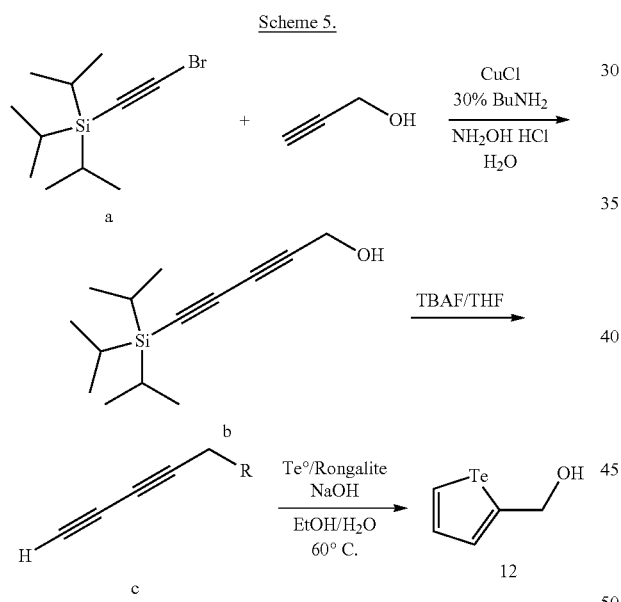

2-(tellurophen-2yl)methanol (12): Tellurium metal (granular,−5-+50 mesh, 640 mg, 5 mmol) was ground to a fine powder using a mortar and pestle. The tellurium powder was added to an aqueous solution of 1M NaOH (30 mL). To the reaction mixture, sodium hydroxymethylsulfinate (1.18 g, 10 mmol) was added and stirred vigorously. The reaction solution was heated using an oil bath, to 95° C. for 0.5 hours and the solution turned a deep purple color. The reaction solution was cooled to 60° C. and stirred for an additional 5 mins. In 5 mL of ethanol, penta-2,4-diyn-1-ol (c) (100 mg, 1.25 mmol) was added to the reaction mixture. Compound c was prepared analogously to compound 6. This solution mixture was stirred for 1.5 hours at 60° C. The reaction was then exposed to oxygen by removing the septa and allowing in atmosphere. The reaction was allowed to cool to room temperature and stirred for 15 mins. Upon cooling, the reaction was diluted with a sat. NH₄Cl solution (100 mL). The solution was extracted with EtOAc (2×100 mL). The combined organic layer was washed with 1M HCl (2×100 mL), brine (2×100 mL), dried over MgSO₄, filtered, concentrated, and dried under vacuum to give a dark orange-brown oil crude product. The crude product was purified by flash chromatography (5%-50% EtOAc/Hexanes on silica gel) to give a light yellow solid (200 mg, 76%). ¹H NMR (500 MHz, CDCl₃, δ): 8.83 (dd, J=6.9, 1.2 Hz, —HCTe—, 1H), 7.68 (m, —HCHCTe—, 1H), 7.49 (m, —TeCCH—, 1H), 4.83 (d, J=1.2 Hz, Tephene-CH₂—, 2H).

Example 7

2-(chloromethyl)tellurophene (13)

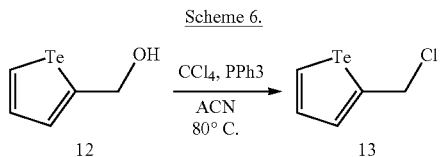

2-(chloromethyl)tellurophene (13): 2-(tellurophen-2yl) methanol (100 mg, 0.47 mmol) and triphenylphosphine (156 mg, 0.59 mmol) was added to solution of acetonitrile (15 mL). Carbon tetrachloride (300 uL, 0.47 mmol) was added drop-wise to the solution. The reaction was refluxed at 80° C. for 30 mins. The reaction was allowed to cool to room temperature and stirred for 5 mins. Upon cooling, the reaction was concentrated and dried under vacuum to give an orange oil crude product (55 mg, 41%). ¹H NMR (400 MHz, CDCl₃, δ): 7.61 (m, —HCTe—, 1H), 7.48 (m, —HCHCTe—, 1H), 7.41 (m, —TeCCH—, 1H), 4.74 (d, J=1.1 Hz, Tephene-CH₂—, 2H).

Example 8

2,5-dioxopyrrolidin-1-yl 3-(tellurophen-2-yl)propanoate (14)

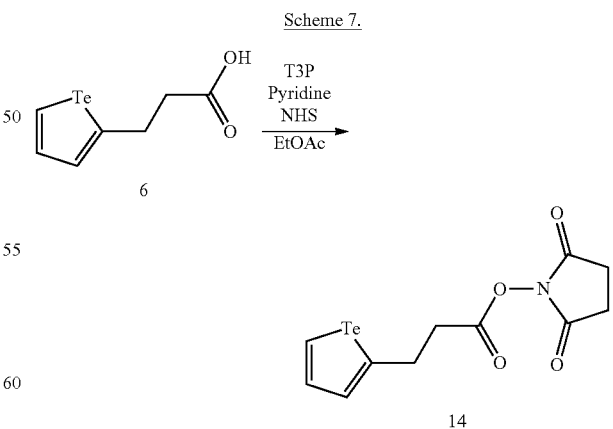

2,5-dioxopyrrolidin-1-yl 3-(tellurophen-2-yl)propanoate (14): 3-(tellurophen-2-yl)propanoic acid (150 mg, 0.59 mmol) was dissolved in a solution mixture of EtOAc (5 mL) and pyridine (2.5 mL). T3P (379 mg, 1.18 mmol) was added to the mixture and the reaction was cooled to 0° C. using an ice bath and stirred for 5 mins. Upon cooling, NHS (75 mg, 0.65 mmol) was added to the reaction and the reaction was allowed to reach room temperature. The reaction was stirred overnight at room temperature. Upon completion by TLC, the reaction was diluted with water (50 mL). The resulting reaction mixture was extracted into EtOAc (50 mL×3). The combined organic layers were concentrated and dried under vacuum to give the product (155 mg, 76%). %). $^1$H NMR (500 MHz, CDCl$_3$, δ): 8.73 (dd, J=6.9, 1.2 Hz, —HCTe—, 1H), 7.59 (m, —HCHCTe—, 1H), 7.41 (m, —TeCCH—, 1H), 3.33 (t, J=7.3, Tephene-CH$_2$—, 2H), 2.97 (t, J=7.3, —CH$_2$CH$_2$COOH, 2H), 2.84 (5, succinimide, 4H).

Example 9

(S)-2-((tert-butoxycarbonyl)amino)-7-(triisopropylsilyl)hepta-4,6-diynoic acid (15)

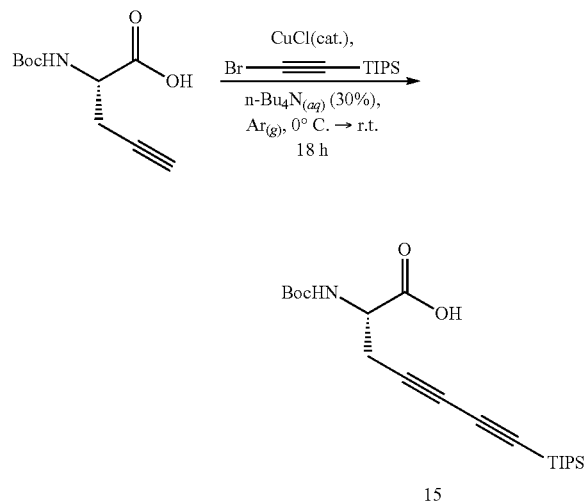

(S)-2-((tert-butoxycarbonyl)amino)-7-(triisopropylsilyl)hepta-4,6-diynoic acid (15): A scintillation vial was charged with CuCl (19 mg, 0.1914 mmol), aqueous n-butylamine (5.5 mL, 30% n-butylamine: H$_2$O (v/v)), and a magnetic stir bar. Several grains of hydroxylamine hydrochloride were added to the vigorously-stirring blue solution until the solution turned clear. Next, boc-L-propargylglycine (free acid, 428.5 mg, 2.01 mmol) was added quickly, the atmosphere of the vial was exchanged with argon, and the vial cooled in an ice bath. To the resultant yellow solution was added (bromoethynyl)triisopropylsilane 1, (500 mg, 1.914 mmol), dropwise, over 5 minutes. After this addition was complete the ice bath was removed and the reaction was allowed to stir for at least 4 hours at room temperature. If the reaction turned blue, additional grains of hydroxylamine hydrochloride were added; this reverted the solution back to a yellow/reddish-brown. Once the reaction was complete, the product was extracted into diethylether (3× wash with 1.0 M HCl), dried over anhydrous MgSO$_4$, and concentrated to afford the title compound as a viscous clear oil (750 mg, ~quantitative).

Example 10

(S)-2-((tert-butoxycarbonyl)amino)-3-(tellurophen-2-yl)propanoic acid (16)

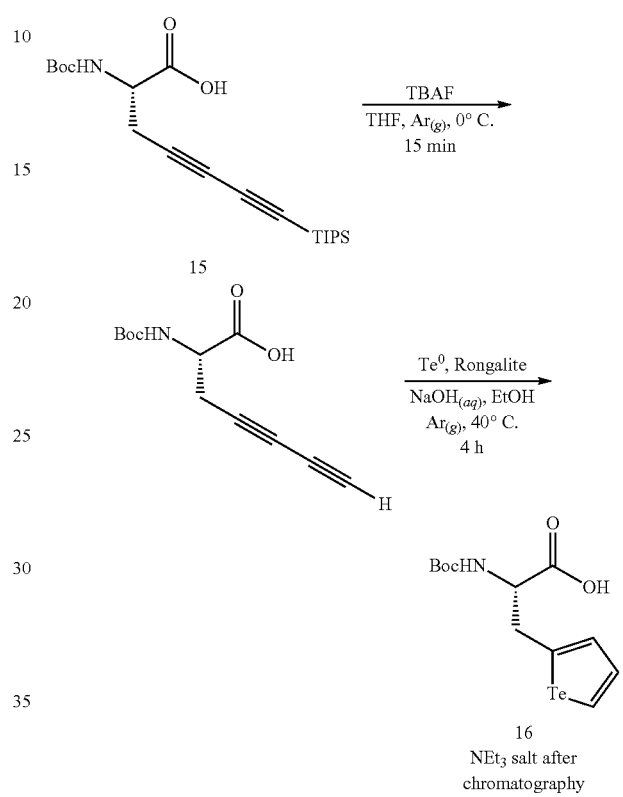

(S)-2-((tert-butoxycarbonyl)amino)-3-(tellurophen-2-yl)propanoic acid (16):

Part A: An oven-dried 25 mL round bottom flask was charged with (S)-2-((tert-butoxycarbonyl)amino)-7-(triisopropylsilyl)hepta-4,6-diynoic acid (750 mg, 1.9 mmol), dry tetrahydrofuran 15 (7.7 mL), and a dry magnetic stir bar. The flask was then cooled on an ice bath and the atmosphere exchanged with argon. Tetrabutylammonium fluoride (7.7 mL of a 1.0 M solution in anhydrous tetrahydrofuran, 7.6 mmol) was then added all at once. The reaction was allowed to stir on ice for 15 minutes, after which the entire mixture was injected all at once into the solution prepared in part B.

Part B: A 2-neck 250 mL round bottom flask was charged with monosodium hydroxymethanesulfinate dihydrate (3.26 g, 21.12 mmol), freshly-pulverized tellurium metal (from −5-+50 mesh pellets, 270 mg, 2.11 mmol), degassed aqueous sodium hydroxide (2.0 M, 20 mL), absolute ethanol (20 mL), and a magnetic stir bar. Argon gas was bubbled through the solution for 20 minutes with stirring. One neck of the reaction vessel was then fitted with a reflux condenser, and the other with a rubber septum. The vessel was then placed in a silicon oil bath at 75° C. and a constant stream of argon gas was maintained flowing through the flask. Once a deep purple solution formed, the temperature of the oil bath was lowered to 40° C. Once the contents of the flask equilibrated with the new temperature of the oil bath, the solution prepared in Part A was injected all at once through the rubber septum. The reaction was allowed to stir for at least 4 hours, after which the flask was removed from the oil bath, the contents exposed to air until unreacted tellurium metal precipitated, and the organic components extracted into ethyl acetate (5-10× wash with 1.0 M HCl), dried over anhydrous MgSO$_4$, and concentrated to afford the title compound as an impure yellow oil. The product was further purified via flash chromatography (silica gel stationary phase, 1% triethylamine, 3% methanol, 96% chloroform mobile phase, product R$_f$~0.55-0.6 on silica-coated thin layer chromatography plate with 2% triethylamine, 8% methanol, 90% chloroform mobile phase, staining with KMnO$_4$) to afford the triethylammonium salt of the title compound as a viscous clear oil (474 mg, 53% as calculated from the (bromoethynyl)triisopropylsilane starting material). $^1$H NMR (400 MHz, CDCl$_3$): δ 8.60 (dd, 1H, J=7.0, 1.2 Hz), 7.54 (dd, 1H, J=7.0, 3.9 Hz), 7.35 (m, 1H), 5.65 (br s, 1H), 4.26 (br s, 1H), 3.48 (br s, 2H), 1.41 (s, 9H) ppm.

Example 11

(S)-2-amino-3-(tellurophen-2-yl)propanoic acid triethylammonium salt (17)

Scheme 10.

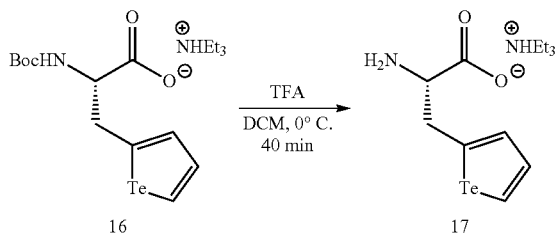

(S)-2-amino-3-(tellurophen-2-yl)propanoic acid triethylammoinum salt (17): An oven-dried scintillation vial in an ice bath was charged with the triethylammonium salt of (S)-2-((tert-butoxycarbonyl)amino)-3-(tellurophen-2-yl) propanoic acid (16) (234 mg, 0.5 mmol), dichloromethane (2.5 mL), trifluoroacetic acid (2.5 mL), and a dry magnetic stir bar. The reaction was allowed to stir in the ice bath for 40 minutes, after which the reaction was neutralized with triethylamine (monitored using litmus paper). The reaction was then concentrated, and reconstituted in a small volume of 2% methanol/H$_2$O. The product was purified on a C18 reverse-phase plug (2% methanol/H$_2$O to 1:1 methanol/H$_2$O mobile phase) to afford the title compound (100 mg, 54%) as a clear oil which solidified (white solid) upon freeze-drying. $^1$H NMR (400 MHz, MeOD-d$_4$): δ 8.92 (dd, 1H, J=7.0, 1.3 Hz), 7.63 (dd, 1H, J=7.0, 3.9 Hz), 7.52 (dd, 1H, J=3.9, 1.3 Hz), 4.21 (app t, 1H, J=5.0 Hz), 3.49 (m, 2H) ppm.

Example 12

(3S,4R,5S,6R)-6-(acetoxymethyl)-3-(3-(tellurophen-2-yl)propanamido)tetrahydro-2H-pyran-2,4,5-triyl-triacetate (18)

Scheme 11.

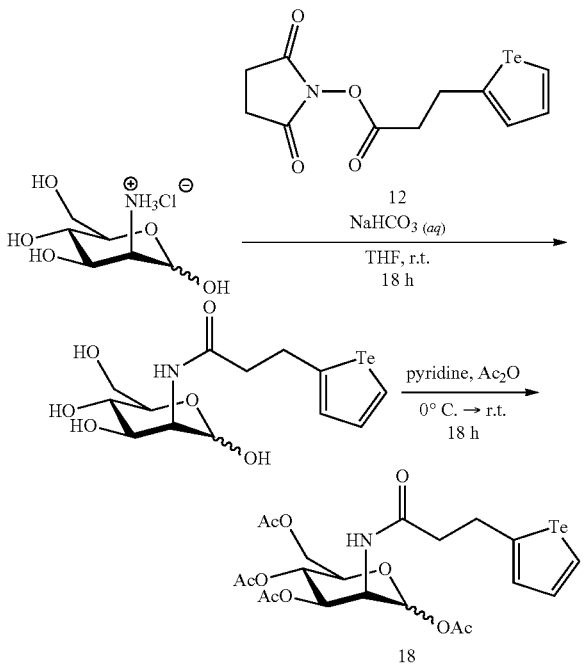

(3S,4R,5S,6R)-6-(acetoxymethyl)-3-(3-(tellurophen-2-yl)propanamido)tetrahydro-2H-pyran-2,4,5-triyl triacetate (18): A scintillation vial was charged with mannosamine hydrochloride (42.5 mg, 0.197 mmol), aqueous sodium bicarbonate (3 mL, 100 mM), tetrahydrofuran (2 mL), 2,5-dioxopyrrolidin-1-yl 3-(tellurophen-2-yl)propanoate (12) (86 mg, 0.247 mmol), and a magnetic stir bar. The mixture was allowed to stir at room temperature for 18 hours, after which the reaction was concentrated via rotary evaporation and further dried under high vacuum. Next, the dry reaction crude was reconstituted in anhydrous pyridine (4 mL) and cooled in an ice bath. Acetic anhydride (3 mL) was then added and the mixture was allowed to warm to room temperature over 18 hours (with stirring). Volatile compounds were removed via rotary evaporation (toluene was added to aid in evaporation of the pyridine). The product was purified via flash chromatography (silica gel stationary phase, 3:1 to 1:1 pentanes:ethyl acetate, product Rf~0.55 on silica-coated thin layer chromatography plate with 1:1 pentanes:ethyl acetate mobile phase, staining with ninhydrin) to afford the product as a clear oil (61 mg, 53%). $^1$H NMR (500 MHz, CDCl$_3$): δ 8.71 (dd, 1H, J=6.9, 1.3 Hz), 7.58 (dd, 1H, J=6.9, 3.8 Hz), 7.39 (m, 1H), 5.96 (d, 1H, J=1.9 Hz), 5.84 (br m, 1H), 5.31 (dd, 1H, J=10.2, 4.6 Hz), 5.10 (t, 1H, J=10.2 Hz), 4.64 (ddd, 1H, J=9.1, 4.6, 1.9 Hz), 4.24 (m, 1H), 4.03 (m, 2H), 3.24 (dt, 2H, J=6.9, 1.2 Hz), 2.60 (m, 2H), 2.17 (s, 3H), 2.08 (s, 3H), 2.05 (s, 3H), 1.96 (s, 3H) ppm.

Example 13

(4S,5R,6R)-5-acetamido-6-((1R,2R)-1,2-dihydroxy-3-(3-(tellurophen-2-yl)propanamido)propyl)-2,4-dihydroxytetrahydro-2H-pyran-2-carboxylic Acid Sodium Salt (19)

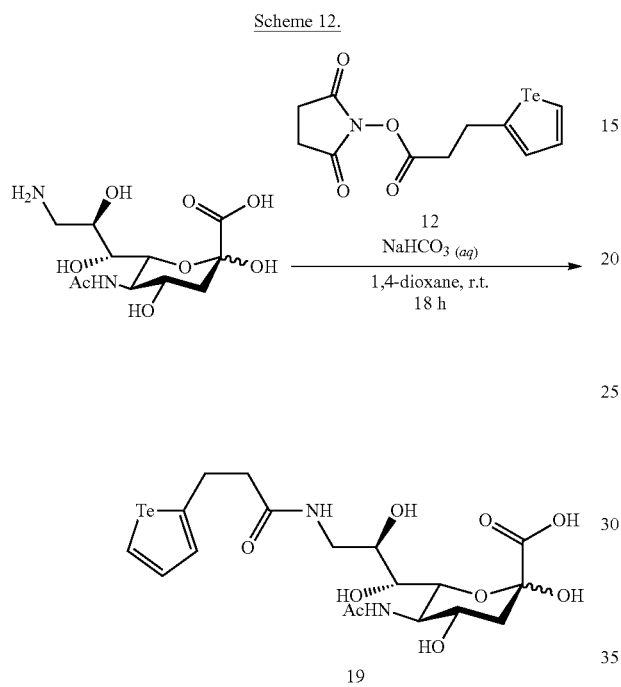

(4S,5R,6R)-5-acetamido-6-((1R,2R)-1,2-dihydroxy-3-(tellurophen-2-yl)propanamido)propyl)-2,4-dihydroxytetrahydro-2H-pyran-2-carboxylic acid sodium salt (19): A 25 mL round bottom flask was charged with (4S,5R,6R)-5-acetamido-6-((1R,2R)-3-amino-1,2-dihydroxpropyl)-2,4-dihydroxytetrahydro-2H-pyran-2-carboxylic acid (108 mg, 0.35 mmol), saturated aqueous sodium bicarbonate (5.9 mL), 1,4-dioxane (5.8 mL), 2,5-dioxopyrrolidin-1-yl 3-(tellurophen-2-yl)propanoate (12) (162.37 mg, 0.465 mmol), and a magnetic stir bar. The mixture was allowed to stir at room temperature for 18 hours, after which the reaction was concentrated via rotary evaporation. The crude mixture was then reconstituted in 2% methanol/$H_2O$ and the product purified on a C18 reverse-phase plug (2% methanol/$H_2O$ to 1:1 methanol/$H_2O$ mobile phase) to afford the title compound as a clear oil. $^1$H NMR (500 MHz, MeOD-$d_4$): δ 8.70 (dd, 1H, J=6.9, 1.3 Hz), 7.52 (dd, 1H, J=6.9, 3.9 Hz), 7.34 (m, 1H), 3.97 (m, 3H), 3.68 (m, 1H), 3.63 (dd, 1H, J=13.8, 3.2 Hz), 3.17 (m, 3H), 2.53 (t, 2H, J=7.3 Hz), 2.08 (dd, 1H, J=12.6, 4.4 Hz), 1.98 (s, 3H), 1.88 (t, 1H, J=11.8 Hz) ppm. NOTE: the missing resonance corresponding to a single proton may lie under the residual solvent peak at 3.31 ppm.

Example 14

1-(2-difluoromethyl-4-(3-(tellurophen-2-yl)propanamido)phenyl)-β-D-galactopyranose (24)

Scheme 13. Synthesis of B-galactosidase tellurophene probe (24).

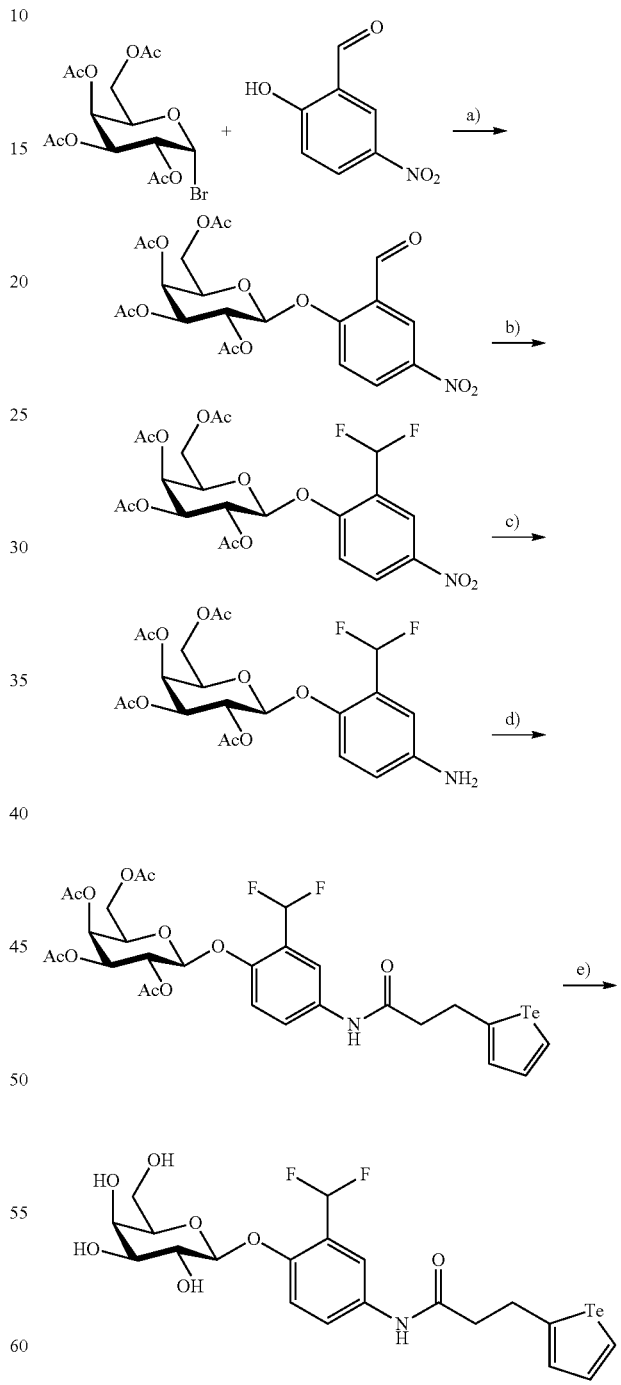

Reactions and conditions: a) Bu$_4$NBr, 1M NaOH:DCM (52%); b) dimethylaminosulfur trifluoride, DCM (89%); c) H$_2$, Pd/C, EtOAc (97%); d) 3-(tellurophen-2-yl)propanoic acid, T3P, pyridine:EtOAc (59%); e) NaOMe, MeOH (75%).

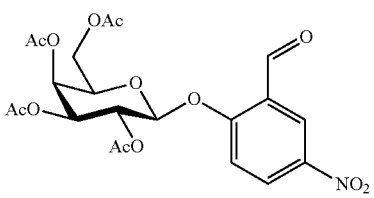

1-(2-formyl-4-nitrophenyl)-2-3,4,6-tetraacetyl-β-D-galactopyranose (20): A solution of tetrabutylammonium bromide (0.783 g, 2.43 mmol) in 1 M NaOH (3.7 mL) was added to 2-hydroxy-5-nitrobenzaldehyde (0.609 g, 3.65 mmol) in DCM (7.4 mL) with stirring at room temperature. A solution of 2,3,4,6-tetraacetyl-α-D-galactopyranosyl bromide (1.00 g, 2.43 mmol) in minimal DCM was added, and the mixture was stirred for three days at room temperature. It was subsequently diluted with DCM (200 mL) and washed with 2 M NaOH (4×200 mL) and brine (200 mL). The organic extract was dried over MgSO$_4$, filtered and concentrated to yield an orange solid. The crude product was purified via flash chromatography (stationary phase, silica gel; mobile phase, DCM, 0%-5% MeOH, 0.1% triethylamine) to afford compound 20 (1.23 g, 51%) as a viscous orange liquid. $^1$H NMR (500 MHz, CDCl$_3$) δ 10.33 (s, 1H, CHO), 8.71 (d, J=3.0 Hz, 1H, Ar—H), 8.42 (dd, J=9.0 Hz, 3.0 Hz, 1H, Ar—H), 7.25 (d, J=9.0 Hz, 1H, Ar—H), 5.61 (dd, J=10.5 Hz, 8.0 Hz, 1H, H-2), 5.51 (dd, J=3.5 Hz, 1H, H-4), 5.28 (d, J=7.5 Hz, 1H, H-1), 5.18 (dd, J=10.5 Hz, 3.5 Hz, 1H, H-3), 4.15-4.25 (m, 3H, H-5H-6a, H-6b), 2.20, 2.08, 2.07, 2.03 (s, 3H, 4×COCH$_3$).

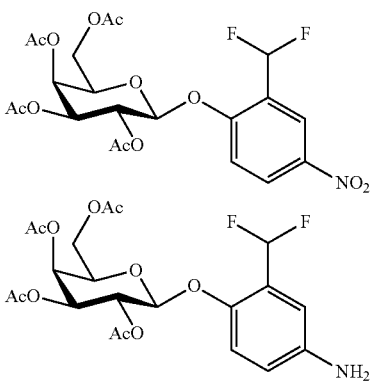

1-(2-difluoromethyl-4-nitrophenyl)-2-3,4,6-tetraacetyl-β-D-galactopyranose (21): Dimethylaminosulfur trifluoride (0.146 mL, 1.50 mmol) was added to a solution of 20 (0.622 g, 1.25 mmol) in dry DCM (16 mL). The reaction was stirred at room temperature under N$_2$ for 6.5 h, then quenched by the addition of ice (100 mL) and extracted into DCM (2×100 mL). The combined organic extracts were washed with water (100 mL) and brine (100 mL), dried over MgSO$_4$, filtered and concentrated to yield a yellow oil. The crude product was purified via flash chromatography (stationary phase, silica gel; mobile phase, DCM, 5% MeOH, 0.1% triethylamine) to afford compound 21 (0.577 g, 89%) as a viscous yellow liquid. $^1$H NMR (500 MHz, CDCl$_3$) δ 8.49 (dd, J=3.0 Hz, 1.5 Hz, 1H, Ar—H), 8.33 (dd, J=9.0 Hz, 2.0 Hz, 1H, Ar—H), 7.22 (d, J=9.5 Hz, 1H, Ar—H), 6.85 (t, J=54.5 Hz, 1H, CHF$_2$), 5.57 (dd, J=10.5 Hz, 8.0 Hz, 1H, H-2), 5.50 (app d, J=3.5 Hz, 1H, H-4), 5.16 (d, J=8.0 Hz, 1H, H-1), 5.15 (dd, J=11.0 Hz, 3.5 Hz, 1H, H-3), 4.15-4.25 (m, 3H, H-5H-6a, H-6b), 2.20, 2.09, 2.06, 2.03 (s, 3H, 4×COCH$_3$). DART-MS m/z calcd. for C$_{21}$H$_{23}$F$_2$NO$_{12}$ 519.40, found 537.15170 [M+NH$_4$]$^+$.

1-(2-difluoromethyl-4-aminophenyl)-2-3,4,6-tetraacetyl-β-D-galactopyranose (22): Pd/C (5% Pd, 0.220 g) was added to a stirring solution of 21 (1.08 g, 2.08 mmol) in ethyl acetate (5 mL) in a 25 mL three-necked round-bottom flask. The flask was purged with N$_2$, then H$_2$, then placed under 2.04 atm of fresh H$_2$ overnight at room temperature with stirring. Pd/C was filtered through celite, and the filtrate was concentrated to afford pure 22 (0.990 g, 97%) as an orange solid. $^1$H NMR (400 MHz, CDCl$_3$) δ 6.94 (s, 1H, Ar—H), 6.87 (dd, J=2.8 Hz, 1.6 Hz, 1H, Ar—H), 6.80 (t, J=55.6 Hz, 1H, CHF$_2$), 5.47 (dd, J=10.8 Hz, 8.0 Hz, 1H, H-2), 5.44 (dd, J=3.2 Hz, 0.8 Hz, 1H, H-4), 5.08 (dd, J=10.8 Hz, 3.6 Hz, 1H, H-3), 4.86 (d, J=8.0 Hz, 1H, H-1), 4.00-4.26 (m, 3H, H-5, H-6a, H-6b), 2.19, 2.08, 2.06, 2.01 (5, 3H, 4×COCH$_3$). $^{19}$F NMR (376 MHz, CDCl$_3$) δ -108.43 (dd, J=300.8 Hz, 56.4 Hz, 1F), -122.67 (dd, J=300.8 Hz, 56.4 Hz, 1F). DART-MS m/z calcd. for C$_{21}$H$_{25}$F$_2$NO$_{10}$ 489.14, found 490.2 [M+H]$^+$.

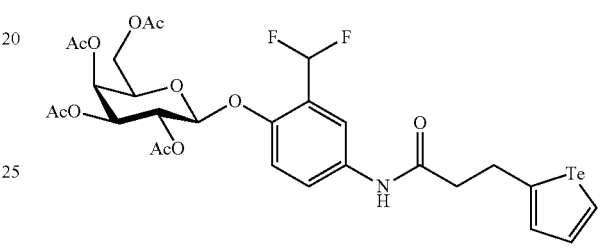

1-(2-difluoromethyl-4-(3-(tellurophen-2-yl)propanamido)phenyl)-2-3,4,6-tetraacetyl-β-D-galactopyranose (23): 22 (0.176 g, 0.360 mmol), 3-(tellurophen-2-yl)propanoic acid (6) (0.082 g, 0.327 mmol), pyridine (0.10 mL) and ethyl acetate (0.20 mL) were added to a 25 mL round-bottom flask at -20° C. under N$_2$. Propylphosphonic acid (T3P, 50 wt. % in ethyl acetate, 0.43 mL) was added dropwise and the solution was stirred at 0° C. for 20 h. The solution was diluted with DCM (40 mL) and washed with saturated sodium bicarbonate (3×40 mL), water (40 mL) and brine (40 mL). The organic extract was dried over MgSO$_4$, filtered and concentrated to yield a yellow solid. The crude product was purified via column chromatography (stationary phase, silica gel; mobile phase, DCM, 5% MeOH, 0.1% triethylamine) to afford 23 (0.153 g, 59%) as a yellow solid. $^1$H NMR (400 MHz, CDCl$_3$) δ 8.64 (dd, J=6.8 Hz, 1.2 Hz, 1H, TeAr—H), 7.96 (app. s, 1H, TeAr—H), 7.76 (dd, J=9.2 Hz, 0.4 Hz, 1H, Ar—H), 7.53 (dd, J=10.8 Hz, 4.0 Hz, 1H, TeAr—H), 7.45 (br s, 1H, NH), 7.33 (d, J=2.8 Hz, 1H, Ar—H), 7.04 (d, J=9.2 Hz, 1H, Ar—H), 6.77 (t, J=55.2 Hz, 1H, —CHF$_2$), 5.47 (dd, J=10.8 Hz, 8.0 Hz, 1H, H-2), 5.44 (app. d, J=2.8 Hz, 1H, H-4), 5.09 (dd, J=10.4 Hz, 3.2 Hz, 1H, H-3), 4.95 (d, J=8.0 Hz, 1H, H-1), 4.04-4.22 (m, 3H, H-5, H-6a, H-6b), 3.25 (t, J=6.8 Hz, 2H, —OC—CH$_2$—CH$_2$), 2.64 (t, J=6.8 Hz, 2H, —CH$_2$—CH$_2$—CTe), 2.15, 2.03, 2.02, 1.98 (s, 3H, 3×-COCH$_3$). DART-MS m/z calcd. for C$_{28}$H$_{31}$F$_2$NO$_{11}$ $^{130}$Te, 725.09, found 726.1 [M+H]$^+$.

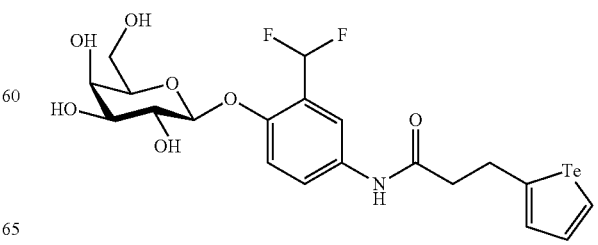

1-(2-difluoromethyl-4-(3-(tellurophen-2-yl)propanamido)phenyl)-β-D-galactopyranose (24): 23 (0.076 g, 0.106 mmol) was dissolved in dry methanol (2 mL) and a 0.5 M solution of NaOMe in methanol (0.20 mL) was added dropwise to the stirring solution. After 3 h, the reaction was quenched by the addition of Dowex® 50W×2 hydrogen form resin (50-100 mesh) until neutral pH, and the solution was concentrated to yield a pale yellow solid. The crude product was desalted using a reverse-phase cartridge (stationary phase, C18; mobile phase, $H_2O$, 50%-100% MeOH) to yield 24 (0.044 g, 75%) as a pale yellow solid. $^1$H NMR (500 MHz, $CD_3OD$) δ 8.71 (dd, J=6.8 Hz, 1.2 Hz, 1H, TeAr—H), 7.77 (d, J=2.5 Hz, 1H, TeAr—H), 7.63 (dd, J=9.0 Hz, 2.0 Hz, 1H, Ar—H), 7.54 (dd, J=7.0 Hz, 4.0 Hz, 1H, TeAr—H), 7.39 (dd, J=4.0 Hz, 1.5 Hz, 1H, Ar—H), 7.27 (s, 1H, Ar—H), 7.16 (t, J=55.5 Hz, 1H, —C$\underline{H}F_2$) 4.83 (d, J=8.0 Hz, 1H, H-1), 3.56-3.90 (m, 6H, H-2, H-3, H-4, H-5, H-6a, H-6b), 3.27 (t, J=8.0 Hz, 2H, —OC—C$\underline{H}_2$—CH$_2$), 2.69 (t, J=7.0 Hz, 2H, —CH$_2$—C$\underline{H}_2$—CTe). $^{13}$C NMR (126 MHz, $CD_3OD$) δ 171.58, 148.43, 136.07, 135.13, 133.49, 124.14, 123.54, 117.29, 116.75, 112.97, 111.11, 109.24, 102.64, 75.70, 73.43, 70.77, 68.76, 60.94, 39.81, 31.91. DART-MS m/z calcd. for $C_{20}H_{23}F_2NO_7$ $^{130}$Te, 557.05, found 575.08786 [M+NH$_4$]$^+$.

Example 15

Synthesis of Telox and Telox-2

Telox was made as described in Scheme 1 of U.S. Application Ser. No. 62/039,762. The structure of Telox is as follows:

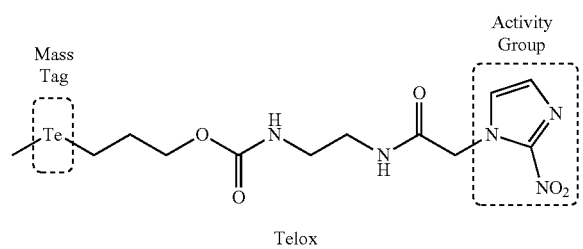

Telox

A tellurophene-containing hypoxia probe was accessed through the synthetic pathway described in Scheme 14. This molecule is referred to herein as Telox-2.

Scheme 14: a) AgNO$_3$ (1.0 eq.), NBS (1.15 eq.), Acetone, 18° C., 3 h, 85%; b) homopropargyl alcohol (1.2 eq.), CuCl (0.02 mol %), 30% BuNH2 (aq.), 0° C.-18° C., 30 min, 80%; c) tetrabutylammonium fluoride (3.3 eq.), THF, 0° C., 10 min, 70%; d) Te0 (4.0 eq.), rongalite (6.67 eq.), NaOH (aq.)/EtOH, 70° C., 2 h, 80%; e) azomycin (1.05 eq.), PPh$_3$ (1.05 eq.), diisopropyl azodicarboxylate (1.05 eq.), THF, 0° C.-18° C., 3 h, 25%.

Telox2 synthesized using 2-(tellurophen-2-yl)propanoic acid as a starting material is described below.

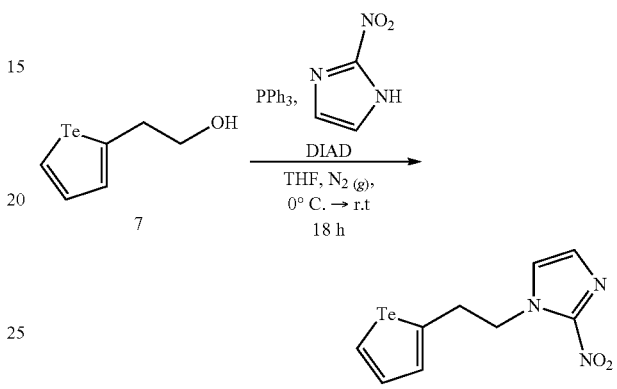

2-nitro-1-(2-(tellurophen-2-yl)ethyl)-1H-imidazole (Telox 2) (25): An oven-dried 50 mL round bottom flask was charged with 2-(tellurophen-2-yl)ethan-1-ol (7) (500 mg, 2.23 mmol), dry tetrahydrofuran (15 mL), triphenylphosphine (1.17 g, 4.47 mmol), azomycin (505.4 mg, 4.47 mmol), and a dry magnetic stir bar. The reaction vessel was flushed with nitrogen and cooled on an ice bath, Diisopropyl azodicarboxylate (0.822 mL, 4.47 mmol) was then added dropwise over 5 minutes and the reaction was allowed to stir, warming gradually to room temperature, for 18 hours. The reaction was then concentrated via rotary evaporation and the product directly purified via flash chromatography (silica gel stationary phase, 10-50% EtOAc/Pentanes, product R$_f$~0.5 on silica-coated thin layer chromatography plate with 1:1 Pentanes/EtOAc mobile phase, staining with KMnO$_4$) to afford the title compound (674.2 mg, 95%) as a yellow solid. $^1$H NMR (600 MHz, CDCl$_3$): δ 8.79 (dd, 1H, J=6.6, 1.2 Hz), 7.55 (dd, 1H, J=7.2, 4.2 Hz), 7.24 (m, 1H), 7.07 (d, 1H, Scheme 14

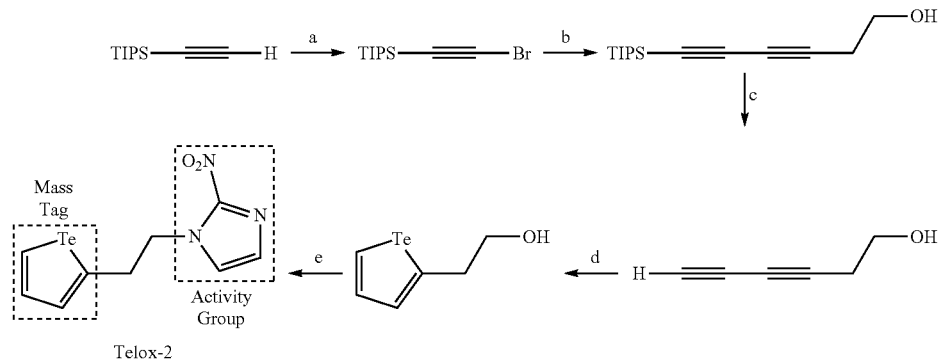

J=1.0 Hz), 6.93 (d, 1H, J=1.0 Hz), 4.65 (t, 2H, J=7.0 Hz), 3.41 (dt, 2H, J=7.0, 1.1 Hz) ppm.

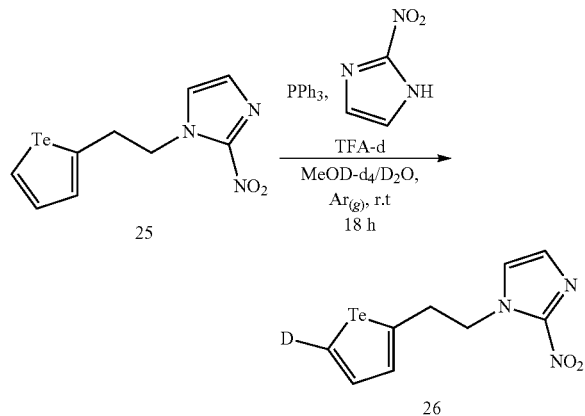

2-nitro-1-(2-(tellurophen-2-yl-5-d)ethyl)-1H-imidazole (Telox 2-d, 26): An oven-dried 20 mL scintillation vial was charged with 2-nitro-1-(2-(tellurophen-2-yl)ethyl)-1H-imidazole (Telox 2, 25, 25 mg, 0.0784 mmol), methanol-$d_4$ (1 mL), deuterium oxide (1 mL), trifluoroacetic acid-d (0.308 mL, 4 mmol), and a magnetic stir bar. The reaction was stirred under argon atmosphere for 18 hours at room temperature. The product was extracted out of solution into chloroform (3× wash with neutral deionized water), dried over anhydrous $MgSO_4$, and concentrated, and obtained as a yellow solid (25 mg, ~quantitative). $^1$H NMR (400 MHz, $CDCl_3$): δ 7.54 (d, 1H, J=3.84 Hz), 7.24 (dt, 1H, J=3.84, 1.1 Hz), 7.06 (d, 1H, J=1.1 Hz), 6.92 (d, 1H, J=1.1 Hz), 4.63 (t, 2H, J=6.9 Hz), 3.40 (dt, 2H, J=6.9, 1.1 Hz) ppm.

Example 16 i. Cell Culture and Maintenance

The HCT116, colorectal carcinoma cell line (CCL-247™) was obtained from American Type Culture Collection and cultured/maintained in RPMI 1640 medium supplemented with 10% fetal bovine serum.

ii. Hypoxia Exposure

HCT116 (500,000) cells were seeded in 60 mm plastic petri dishes (Corning Inc., NY) and incubated for 24 h at 37° C., 21% $O_2$/5% $CO_2$. The cells were transferred to hypoxia chambers (H35/H85 hypoxia workstation, Don Whitley Scientific) maintained at 1%/0.2% or <0.02% $O_2$ for 3 h. Hypoxia experiments (<0.02% $O_2$) were performed by seeding the cells in 60 mm glass plates (Corning Inc., NY).

iii. Confluency (Proliferative Toxicity) Assay

HCT116 cells (25,000) were seeded in a 24 well plate and incubated overnight to allow the cells to adhere. The medium was removed and fresh medium with 50-400 μM TELOX or Telox2 was added and incubated for 1 h. The cells were then transported to a INCUCYTE™ Kinetic Imaging System that was maintained either at 21% or 0.2% O2 at 37° C. Growth profiles were monitored by 10× objective every 4 h by IncuCyte™ ZOOM control software, using integrated confluence algorithm, until the control-untreated cells reached stationary phase. Sixteen high definition-quality images per well were collected in phase-contrast mode and averaged to provide a representative statistical measure of the well confluence.

iv. Metabolic Toxicity Assay

A 96 well clear fluorometer plate was loaded with 200 μL of Jurkat cells at a culture density of 1×10$^6$ cells per mL. To each well was added an appropriate amount of a stock solution of Telox/Telox2 in sterile DMSO to reach a desired concentration of Telox/Telox2 (1-1000 micromole). The concentration of DMSO was 1% in all wells. Cells were allowed to incubate for 24 h at 37° C. under normal atmosphere, after which 20 μL of a commercially available solution of WST-1 in PBS (Roche Diagnostics, product #05015944001) was added to each well (gentle pipetting evenly distributed the reagent throughout the well). Cells were allowed to incubate for a further 0.5 h at 37° C. under normal atmosphere, followed by subsequent measurement of the absorbance of each well at 450 nm using a TECAN Safire 2 plate reader. Data was background corrected vs. wells that contained cell growth media (without cells), an appropriate concentration of Telox2, a final concentration of DMSO=1%, and WST-1. Background correction wells were incubated in the same manner as described for cell-positive wells.

v. Xanthine Oxidase Assay

A septa-sealable quartz cuvette was charged with $K_2PO_4$ buffer (800 μL, 100 mM, pH 7.4), xanthine in $K_2PO_4$ buffer (100 μL, ~5.0 mM xanthine (saturated solution), 100 mM buffer, pH 7.4), and either pimonidazole, Telox or Telox2 in $K_2PO_4$ buffer (100 μL, 1.0 mM of the 2-NI, 100 mM buffer, pH 7.4). The cuvette was then sealed with a rubber septum and the entire solution was degassed with high purity helium gas. Xanthine oxidase (0.2 units of grade III enzyme in a $(NH_4)_2SO_4$ suspension, Sigma-Aldrich, lot # SLBB1572V) was then added via Hamilton syringe and the change in absorbance over time at 325 nm was recorded using an Agilent ultravioletvisible photospectometer (model #8453).

vi. Traditional ICP-MS Experiments

HCT 116 cells (see sections i and ii) were incubated in media containing Telox or Telox2 (100 μM, added as a neat solution in sterile DMSO; final [DMSO]=0.1%) for 3 hours under atmosphere containing an appropriate concentration of $O_2$. Following incubation, the media was removed, cells were washed with sterile PBS, and then separated from the incubation plate via trypsinization (37° C., 10 min) and gentle scraping. The cell suspension was pelleted and resuspended in PBS containing β-ME (1.0 mL, 100 mM). Cells were pelleted, resuspended in PBS (900 μL, no β-ME), and fixed with formaldehyde (100 μL, 37% solution) for 25 minutes.

Following fixation, cells were pelleted, resuspended in PBS containing β-ME (1.0 mL, 100 mM), and pelleted once again. The resultant pellet was then dissolved in ultra pure $HNO_3$ (1.0 mL, ~35% solution) and half of the sample was submitted for analysis via ICP-MS. Signal for $^{130}$Te was then normalized to signal for $^{115}$In at a known concentration (5 ppb, measured from ICPMS set-up solution, PerkinElmer) in order to account for detector sensitivity drift. The resultant signal was further normalized to give the sample with the maximum tellurium signal a value of 1.0. All experiments were performed in duplicate.

vii. Mass Cytometry Experiments

HCT 116 cells (see sections i and ii) were incubated in media containing Telox or Telox2 (100 μM, added as a neat solution in sterile DMSO; final [DMSO]=0.1%) for 3 hours under atmosphere containing an appropriate concentration of $O_2$. Following incubation, the media was removed, cells were washed with sterile PBS, and then separated from the incubation plate via trypsinization (37° C., 10 min) and gentle scraping. The cell suspension was pelleted and resuspended in PBS containing β-ME (1.0 mL, 100 mM). Cells were pelleted, resuspended in PBS (900 µL, no β-ME), and fixed with formaldehyde (100 µL, 37% solution) for 25 minutes. Following fixation, cells were pelleted, resuspended in PBS containing β-ME (1.0 mL, 100 mM), and pelleted once again. Cells were then resuspended in PBS (990 µM, no β-ME) and incubated with either the Ir-containing nucleic acid intercalator (hypoxic cells) or the Rh containing nucleic acid intercalator (normoxic cells) (10 µL, 100 µM solution in sterile PBS) for 20 minutes. Cells were then pelleted and resuspended in PBS (1.0 mL, no β-ME) twice. Cell pellets were then resuspended in PBS containing $^{151/153}$EU beads (1/10 dilution of CyTOF® calibration beads, DVS Sciences, 1.0-2.5 mL depending on pellet size). The two cells samples were then combined (250 µL of each) and 250 µL of the resultant sample was injected onto a second-generation CyTOF® instrument for MC analysis. For experiments involving Ir and Rh, cell samples were not mixed together, but rather, run separately on the CyTOF®. For the Pimonidazole competition experiment, cells were simultaneously incubated with Pimonidazole and Telox or Telox2 (100 µM of each), with all other steps executed in an identical manner to the experiment described above (Note: only the Ir-intercalator was used for this experiment since all samples were run separately).

Results and Discussion

Methyl Telluroether: Synthesis and Stability

The organotellurium functionality that was initially investigated was the methyl telluroether due to its small size and ease of synthesis (Table 1, Compounds 1-4, 8-9). Aryl telluroethers were not investigated due to numerous reports of their redox-activity in living systems and their reported instability under ambient light.[19] The methyl telluroethers were synthesized from nucleophilic lithium methyl tellurolate, using a modified procedure first established by N. Khun, followed by reaction with the desired nucleophile (Scheme 1).[20] The synthesis of compound 3 required quenching the methyl telluroate with water to generate the tellurol prior to the Michael-style addition to methyl acrylate. The yields of these additions ranged from 66 to 91%.

The relative chemical stability of the methyl telluroethers (1-4) were quantified using $^1$H NMR by integration of the $CH_3$—Te signals with respect to a residual DMSO-$d_5$ internal standard. Samples were prepared in a solution of DMSO-$d_6$ and placed under a slow continuous stream of dry ambient atmosphere in a clear glass desiccator. This setup allowed the compound's stability to be monitored without interference from atmospheric water (FIG. 2).

Figure 2A:
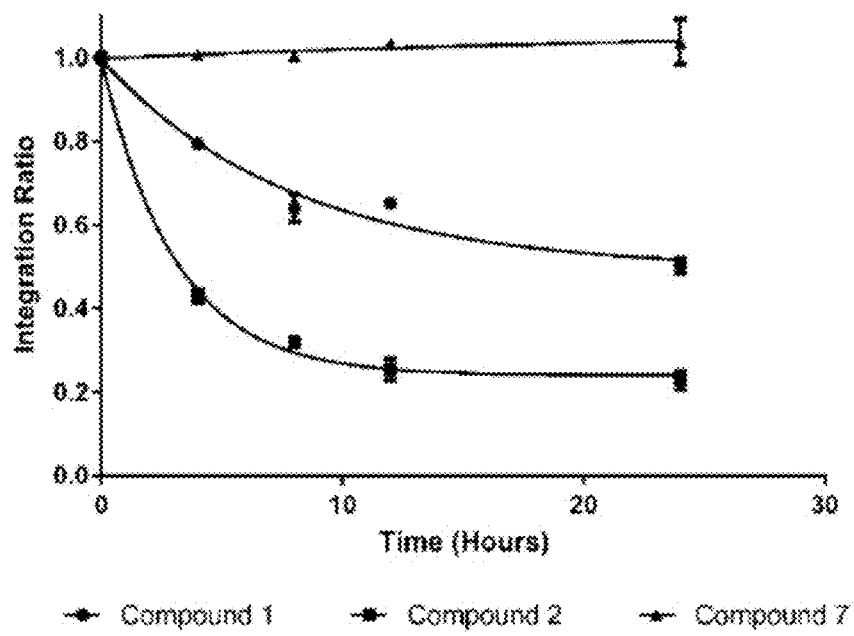
FIGS. 2A-C show the results of $^1$H NMR stability experiments for exemplary compounds 1-11. (A) Compounds 1, 2 and 7. (B) Compounds 3, 4, 5 and 6. (C) Compounds 8, 9, 10 and 11. The organotellurium compounds (~150 µM) were dissolved in d-DMSO with 1,3,5-trioxane, the secondary internal standard. The compounds were kept in clear glass 20 mL vials. The vials were kept in a moisture free environment for 24 hours with continuous supply of ambient atmosphere dried using a series of bubblers containing phosphoric acid, potassium hydroxide and calcium sulfate. Aliquots were analyzed by $^1$H NMR and the organotellurium signals and the d5-H-DMSO peaks were integrated. The ratio between the DMSO and the organotellurium protons at time 0 were taken and normalized to generate a degradation plot. Experimental error was calculated by generating triplicate integration data from each individual preliminary NMR data. This error takes into consideration of integration bias and instrument fluctuations.
Figure 2B:
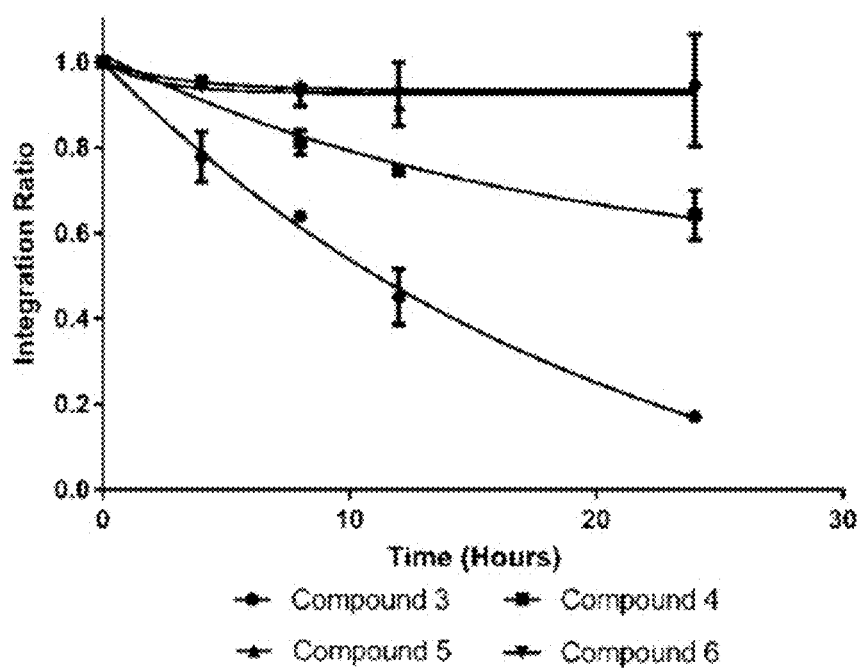

Compounds 1-4 all degraded over the course of the 24 hr. incubation. Compound 4 was the most stable alkyl telluride investigated, degrading approximately 15% over 24 hours (FIG. 2B). Compounds 2 (FIG. 2A) and 3 (FIG. 2B) showed the greatest degradation, approximately 75% and 85%, respectively. (FIG. 2A).

The alkyl tellurides are presumed to undergo oxidation under the experimental conditions. During incubation the initially yellow solutions became colourless with the formation of white precipitate, at varying rates. This phenomena has been previously observed and is presumed to be the telluroxide species forming polymeric structures or the formation of $TeO_2$.[21&22] In addition, it has been observed previously that solutions of TelOx showed the appearance of $^1$H NMR absorptions consistent with chalcogen oxidation.[5,23] Alkyl telluride compounds are also known to undergo hemolytic bond cleavage and this may result in the observed small quantities of dimethyl ditelluride and dimethyl telluride.[24-26] These species are volatile and are observed only in the early time points of compounds 1 and 2. The same species are observed in the 8 hour sample from compound 3. In addition, methyl acrylamide was produced during the degradation of compound 3. The remaining organic components resulting from these degradations could not be identified and may be lost due to their low molecular weight and volatility. To reduce the propensity for oxidative degradation of the telluroethers, the trifluoromethyl telluroethers, 5 and 10, and the tellurophenes 6, 7 and 11 were investigated.

Trifluoromethyl Telluroether: Synthesis and Stability

Compound 5 bearing a trifluoromethyl group will have reduced electron density at the tellurium center and thus should oxidize more slowly. Compound 5 was synthesized by the generation of tetramethylammonium trifluoromethyl tellurolate in situ by treating tellurium metal with trimethyl (trifluoromethyl)silane and tetramethyl ammonium fluoride.[27] Methyl-4-bromobutyrate was added to the solution to give the product 5 in 50% yield (Scheme 1).

The stability of the trifluoromethyl telluride 5 was evaluated under the same conditions as compounds 1-4 (FIG. 2B). Comparison of the structurally related compounds 4 and 5, supported the hypothesis that reducing electron density at the Te center would stabilize the compound, as no degradation was observed over the 24 hour incubation suggesting the trifluoromethyl functionality was stabilizing the telluroether as hypothesized.

Tellurophene: Synthesis and Stability

Tellurophenes have not been evaluated in biological systems, and only recently has the first water soluble tellurophene been reported.[28] Tellurophenes possess interesting photophysical properties and have been investigated as light harvesting agents for solar cell applications and in materials chemistry.[29,30,31] The chalcogen analogue, selenophenes, have been investigated in biological systems with promise as antioxidant molecules. Through computational analysis, ground state aromaticity of tellurophenes are considered to be more stabilized than selenophenes.[32] It was hypothesized that the aromatic nature of the tellurophene would provide greater chemical stability over the telluroether derivatives under the desired biological conditions.

The tellurophenes where synthesized via the addition of $Te^{2-}$ to a mono-functionalized diacetylene in a synthesis modified from Stephens and Sweat's initial report.[33, 34] In synthesizing these tellurophenes, the generation of $Te^{2-}$, commonly, performed by treating an aqueous suspension of $Te^0$ with $NaBH_4$, was carried out using a basic Rongalite ($NaHOCH_2SO_2$) solution which reproducibly generated $Te^{2-}$ and gave higher yields of the desired tellurophene[35]

The trialkylsilyl diacetylenes can, for example, be generated in excellent yield using the Cadiot-Chodkiewicz cross-coupling reaction (Scheme 2).[36] Bromination of triisopropylsilyl acetylene using N-bromosuccinimide and silver nitrate gave the known coupling intermediate using the conditions of Wulff et al.[37] This compound was then coupled using CuCl in 30% $BuNH_2$ with the desired acetylene component of choice. The synthesis of compound 6 utilized the starting material 4-pentynoic acid, and compound 7 utilized the starting material 3-butyn-1-ol. The trialkylsilyl protected diacetylene compounds were deprotected using tetrabutylammonium fluoride and cyclized into tellurophenes 6 and 7 using a basic solution of Rongalite and tellurium metal in good yield (Scheme 2).

The stability of the two tellurophenes was studied using the same protocol as the alkyl telluride species (FIGS. 2A and B). Compounds 6 and 7 have improved stability in comparison to the methyl alkyl telluroethers. Both tellurophene compounds degraded insignificantly over the 24 hr. incubation having similar stability to the trifluoromethyltelluroether 5.

Benzylamine Conjugated Organotellurium Derivatives: Synthesis and Stability

For the future generation of MC probes, the organotelluriums are conjugated to biologically relevant functional groups. Here two conjugation reactions were considered that provide a means to label primary amines, a carbamylation and an amidation reaction. Furthermore, forming benzylamine derivatives of the organotellurim compounds 2, 4, 5 and 7, leads to compounds (8-11) with more comparable partition coefficients for cell toxicity studies (Schemes 3 & 4).

Compound 8 was synthesized via a p-nitrophenyl carbonate generated by the treatment of compound 2 with p-nitrophenyl chloroformate. The reactive carbonate could be purified and stored. Compounds 9 and 10 were synthesized by hydrolysis of the methyl ester and, after isolation of the carboxylic acid, coupling proceeded with DCC in the presence of NHS and benzylamine. Compound 11 was synthesized analogously to 9 and 10 but column chromatography was used for purification.

Figure 2C:
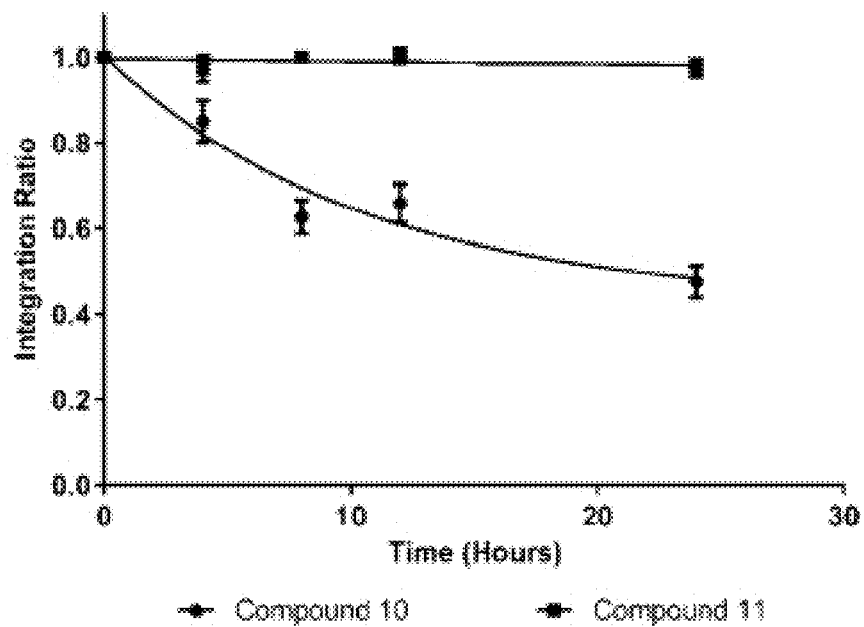

The stability of these benzylamine derivatives was assessed using the developed $^1$H NMR assay (FIG. 2C). The rate of degradation of these compounds mirrored those of the underivatized compounds with the methyl telluride species, compounds 8 and 9, degrading 20-25% over the incubation and compounds 10 and 11 being stable over the incubation. Interestingly the carbamate 8 was considerably more stable than the parent alcohol 2 suggesting the alcohol may directly contribute to the degradation mechanism.

Stability in PBS Buffer

Figure 3:
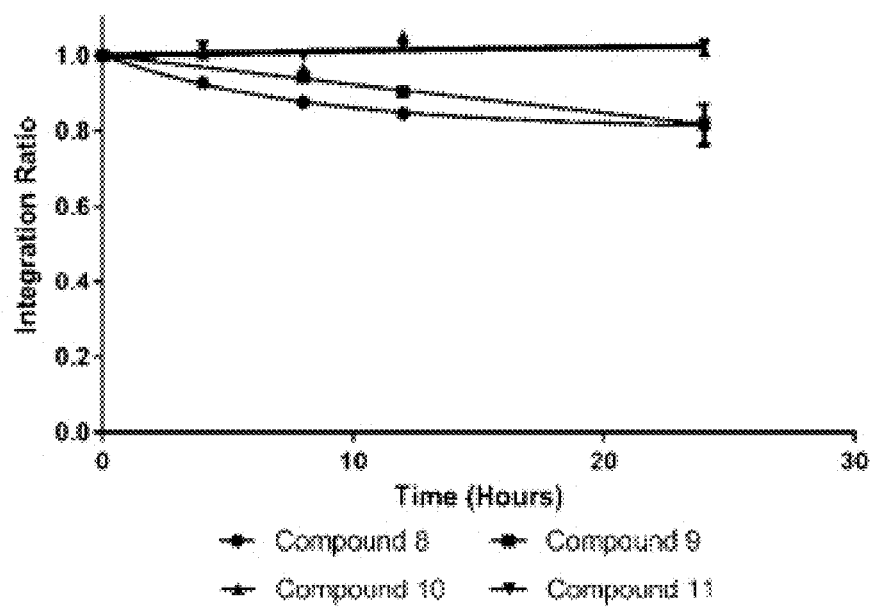
FIG. 3 shows the results of degradation NMR experiments for exemplary compounds 10 and 11 in 50% d-DMSO, d-PBS buffer solutions. The $^{19}$F NMR of compound 10 and $^1$H NMR of compound 11 were taken at shown time points. Compound 10 used trifluoroacetic acid as the internal standard and compound 11 used d5-DMSO.

Of the compounds evaluated, the trifluoromethyltelluroether-amide (10) and the tellurophene-amide (11) exhibited the best stabilities under aerobic conditions. To further validate these compounds as potential MC mass tags, the degradation was also studied in a buffered aqueous solution by dissolving the compounds in a 50/50 solution of d-DMSO/PBS buffer. The compounds were kept in an environment exposed to air and ambient lighting at room temperature. $^{19}$F NMR was used to study compound 10 using a trifluoroacetic acid internal standard while $^1$H NMR was used to study the degradation compound 11 using the d5-DMSO internal standard. As shown in FIG. 3, the trifluoromethyltelluroether 10 showed a 60% degradation after 24 hours. However, under the same conditions the tellurophene 11 was stable.

Cellular Toxicity

To investigate the organotellurium compounds of study as potential probe moieties for MC, the metabolic toxicity of the compounds was evaluated. Organotellurium compounds are often described as toxic, with aryl telluroethers showing cellular toxicity below 100 µM across a range of cell lines under different assay conditions.[9-11,38,39] The toxicity of compounds 8-11 was investigated in a commonly used Jurkat cell line after a 24 hour incubation using the metabolic probe WST-1 (Roche Diagnostics, Laval, Quebec) as per manufacturer's instructions. As compounds 8, 9 and 10 are expected to show degradation over the time frame of the toxicity assay, based on the NMR stability studies, these experiments show the relative toxicity of the compounds and their resulting degradation products (Table 2). Compound 8 had an apparent $LD_{50}$ value of 610 µM, but with a large experimental error due to the lack of solubility of compound 8 at higher concentrations. Compounds 9 and 10 were more toxic with an $LD_{50}$<200 µM, however the tellurophene 11 was less toxic with and $LD_{50}$ of 280 µM. These data suggest that, in general, the alkyl telluroethers and the tellurophenes are less toxic than previously investigated aryl telluroethers. The $LD_{50}$ values of the exemplary organotellurium compounds of the present application provide promise for their use as activity based MC probes since the general MC experiment can be achieved at concentrations of ~100 µM.[5]

Example 17

MC is a powerful analytical tool. Tellurium has valuable characteristics as a mass tag for MC including eight stable isotopes, minimal functional group size and minimal polarity. Various organotellurium compounds functionalized for MC probe development have been synthesized and characterized. The alkyl telluride species are synthetically tractable but have comparatively less compound stability. The tellurophene moiety is available in good yield, is chemically stable and is sufficiently non-toxic.

Telox-2 takes advantage of the same 2-nitroimidazole functionality as Telox, however, the tellurium-containing mass tag is significantly different. Instead of the methyltelluroether functionality in Telox, Telox-2 employs a tellurophene heterocycle (see the functionality labelled "mass tag" in Scheme 14).

Figure 5:
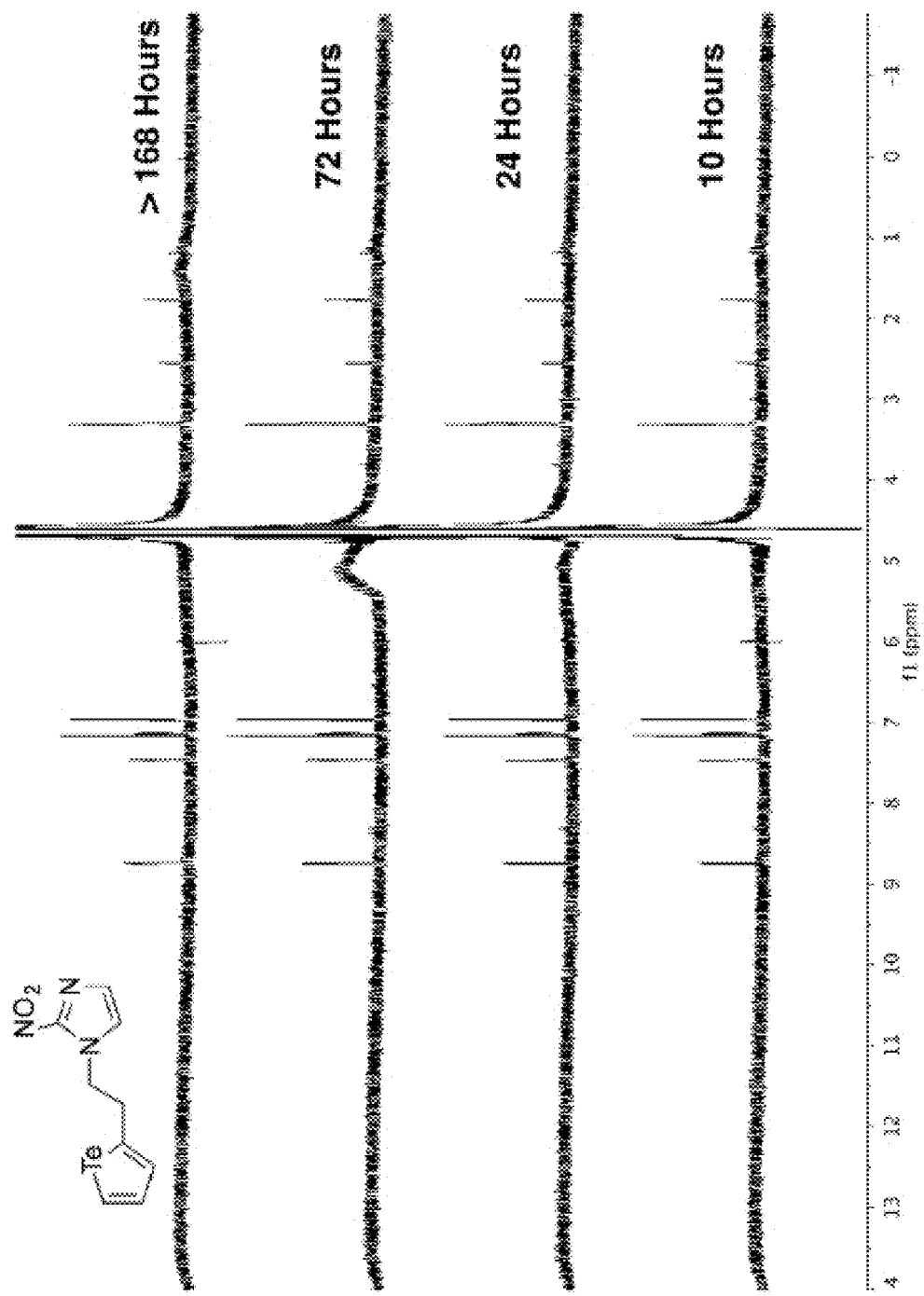
FIG. 5 shows the stability of an exemplary compound, Telox-2, as a function of time as monitored by $^1$H NMR. Concentration of Telox-2=200 µM (0.01% D$_6$-DMSO in D$_2$O).

To investigate the stability of Telox-2 compared to Telox $^1$H NMR spectra of Telox-2 were collected over a period of 1 week under biologically-relevant conditions (0.01% dDMSO in $D_2O$). Telox-2 exhibits remarkable stability for a heavy chalcogen-containing molecule, as NMR data suggests that no observable degradation occurs under the conditions tested (FIG. 5). Additionally, the lack of observable peak-broadening in the $^1$H NMR spectrum of Telox-2 at high concentrations (2 mM) suggests that Telox-2 does not form aggregates or micelles in aqueous solution.

Figure 6:
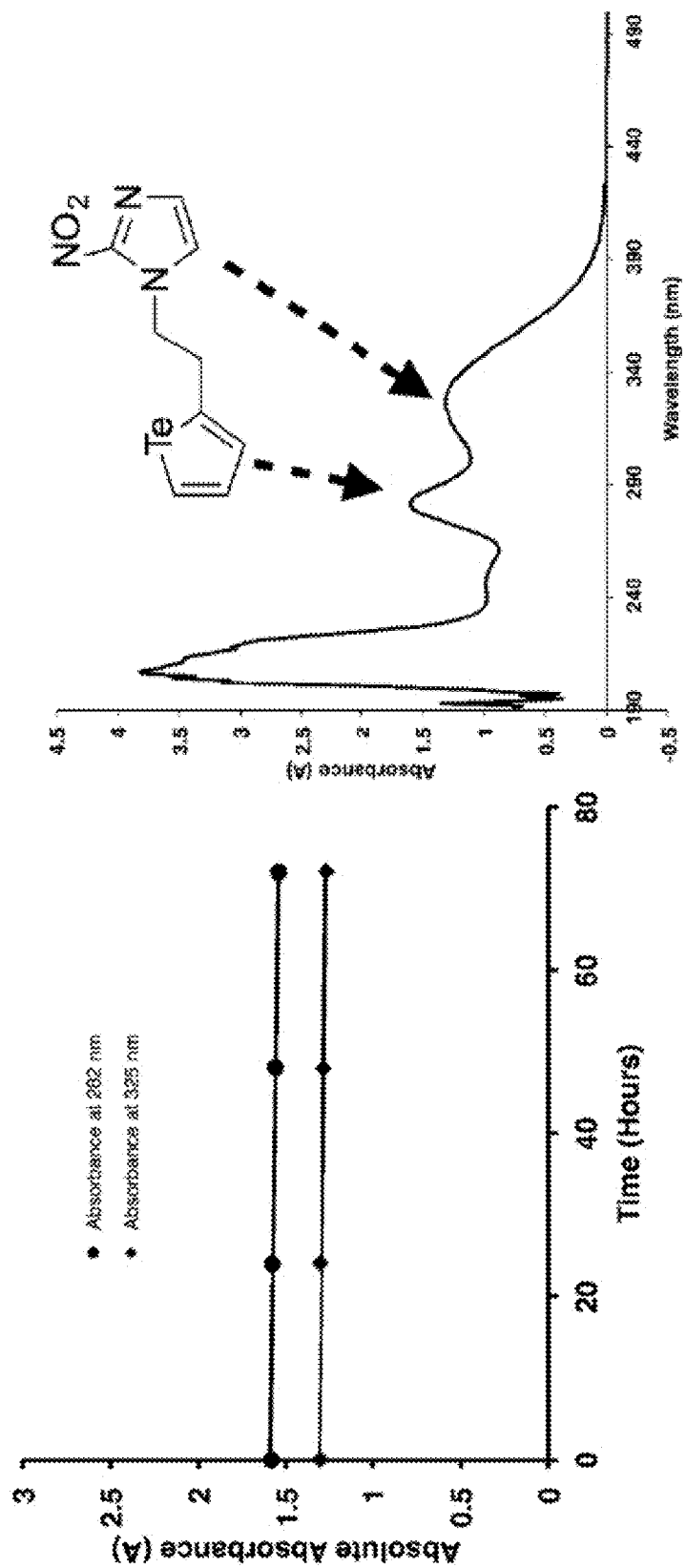
FIG. 6 shows the stability of exemplary compound, Telox-2, as a function of time as monitored by ultraviolet-visible spectroscopy. Concentration of Telox-2=200 µM (0.01% DMSO in phosphate-buffered saline). The small spectrum identifies the unique absorptions of the tellurophene and nitroimidazole functionalities.

An orthogonal stability assay using UV-Vis spectroscopy was performed to corroborate the NMR stability findings (FIG. 6). In this assay, UV-Vis spectra of Telox-2 were recorded at a fixed concentration in aqueous buffer over a period of 3 days. Loss of either heterocycle, tellurophene or nitroimidazole, as a result of degradation would be expected to cause a decrease in absorbance at 282 and/or 325 nm respectively. No change in absorbance was detected in this experiment, thus corroborating our NMR findings that Telox-2 is an exceptionally stable organochalcogen. The empirical log P value of 1.3 for Telox-2 was measured using similar UV-Vis assay conditions. This log P value is lower than would be predicted for the corresponding thiophene and partially explains the unusually high water solubility of Telox-2.

Figure 7A:
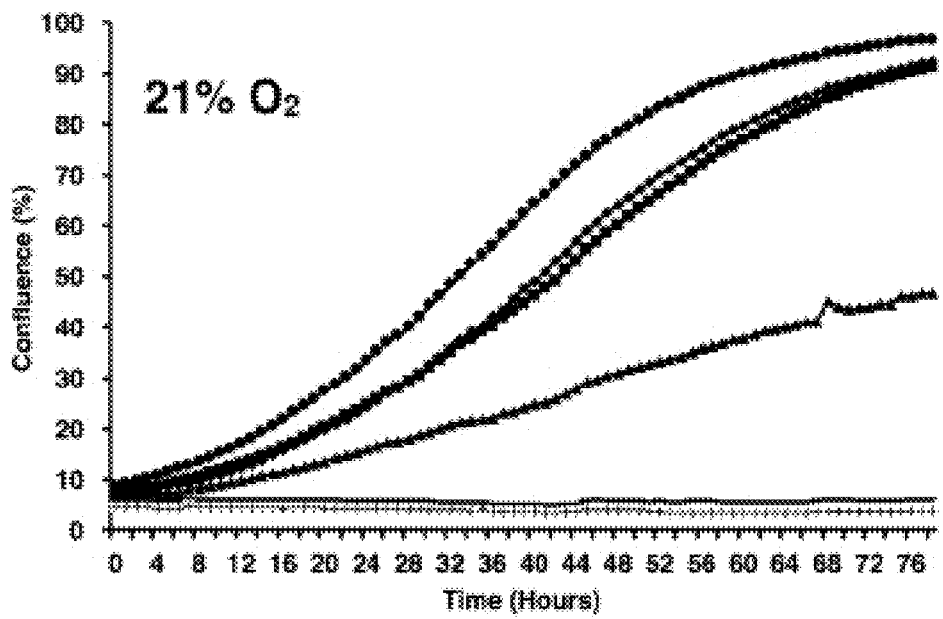
FIGS. 7A, B and C show a) and b) the cell proliferation rate of HCT116 cells as a function of time in the presence of various concentrations of the exemplary compound, Telox-2 (confluency analysis); and c) the metabolic toxicity of the exemplary compound, Telox-2, in Jurkat cells as measured by reduction of WST-1. Cells were incubated with Telox-2 for 24 hours prior to a 30 minute exposure to WST-1.
Figure 7B:
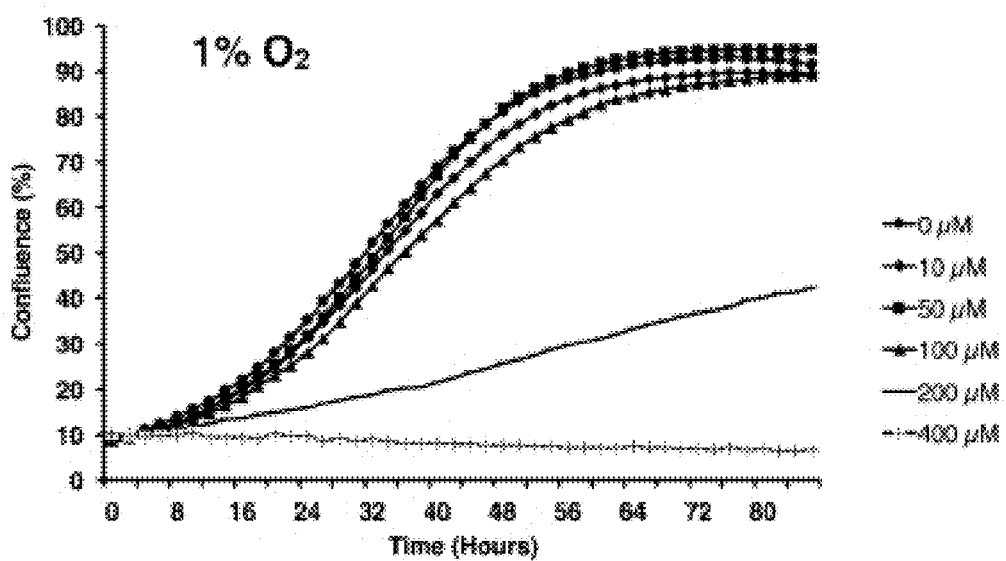
Figure 7C:
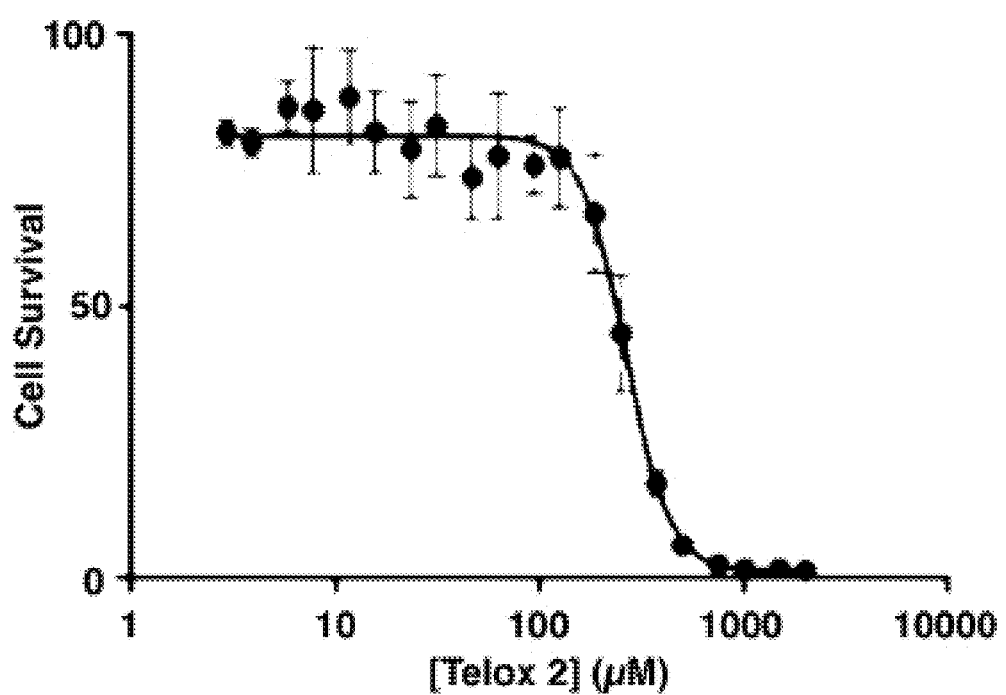

Next, the toxicity profile of Telox-2 was investigated using the same assays that were employed for Telox. Confluency analysis (FIG. 7 parts a and b) indicated that Telox-2 begins to slow cell proliferation at a concentration between 50 and 100 µM under normoxic and between 100 and 200 µM under hypoxic conditions. This proliferative toxicity profile is comparable to Telox, perhaps suggesting that the 2-nitroimidazole functionality is the limiting toxicity factor rather than the tellurium-containing functional group. Metabolic toxicity as measured via a WST-1 assay (FIG. 7 part c) indicated a metabolic $LD_{50}$ of ~270 µM for Telox-2; a value that is, once again, similar to Telox.

Figure 4A:
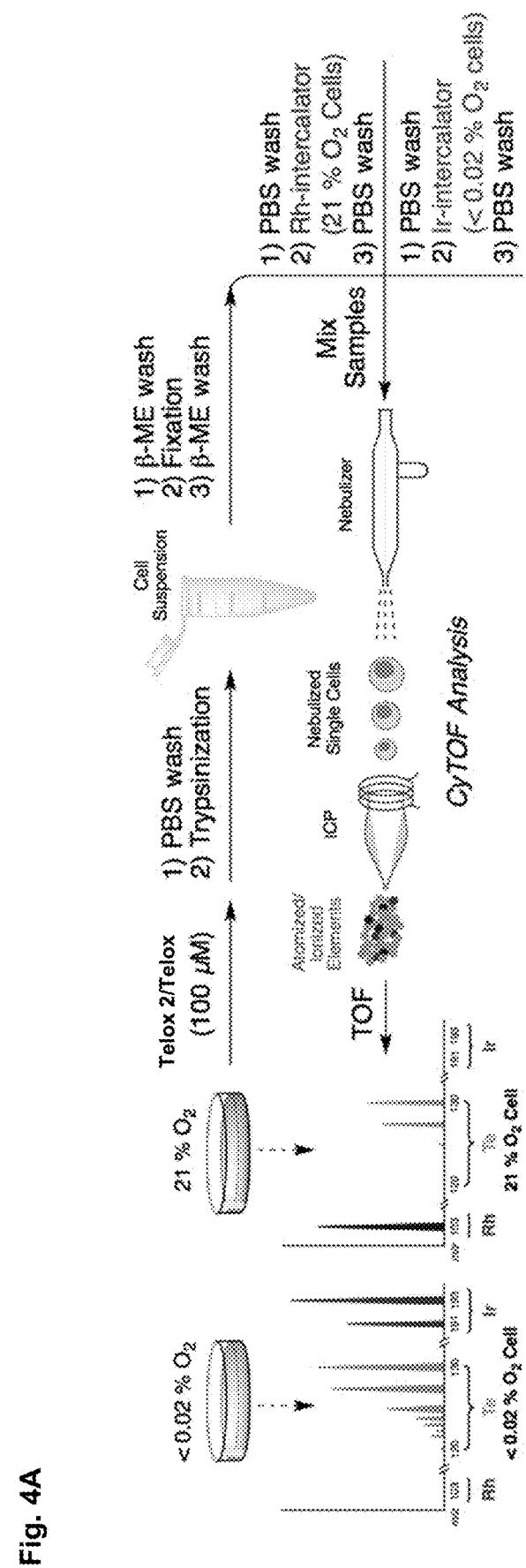
Figure 4E:
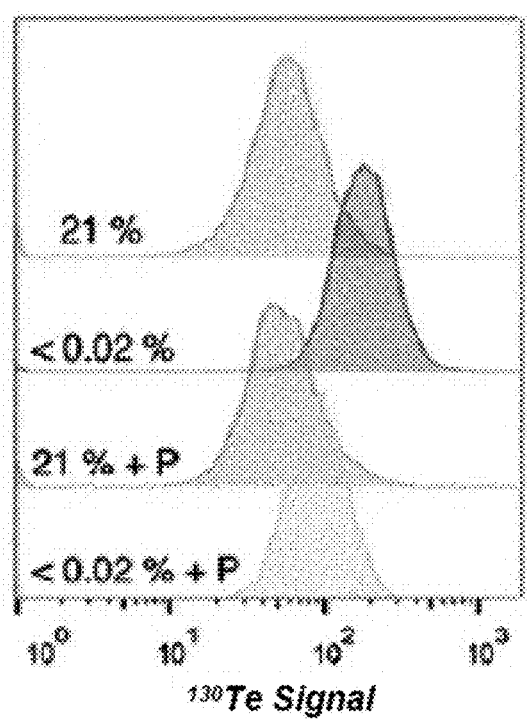
Figure 8B:
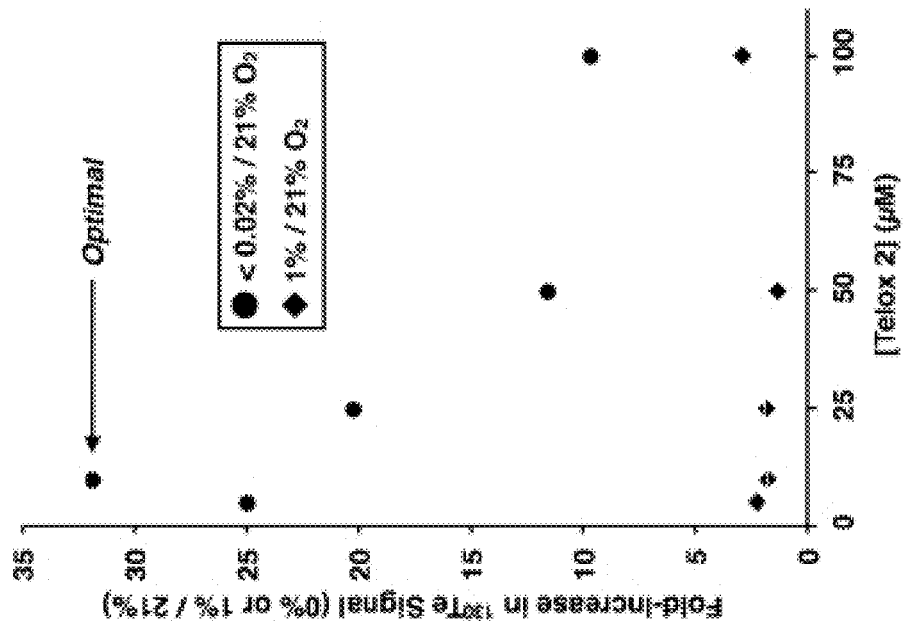
Figure 8A:
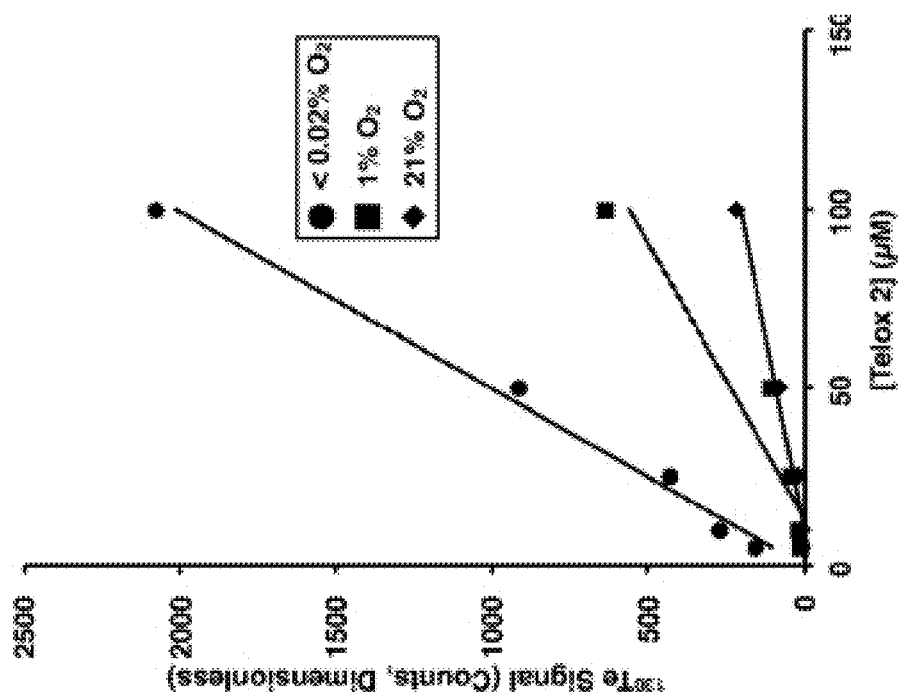

Oxygen labelling was investigated using the scheme in FIG. 4a. Results for Telox are shown in FIG. 4b-e).Evaluation of oxygen-labelling and dose-labelling relationships for Telox-2 (FIG. 8) in HCT116 cells revealed an optimal probe concentration of 10 µM (under these conditions) to maximize signal-to-noise (i.e. specific labelling+nonspecific binding) between cells incubated under normoxic conditions vs. those incubated under near-anoxic conditions. Signal-to-noise for cells incubated under moderately hypoxic conditions (1% $O_2$) was significantly lower than for their near-anoxic counterparts.

Figures 9A, 9B:
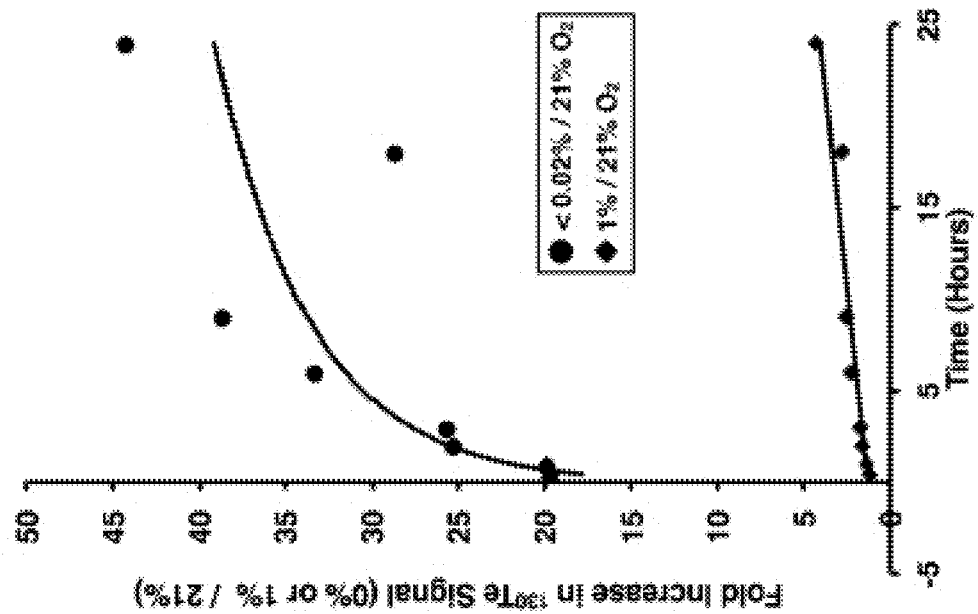
FIGS. 9A-D show a) Absolute $^{130}$Te signal as a function of time as determined by mass cytometry analysis of HCT116 cells incubated with 10 µM of the exemplary compound,Telox-2 (constant exposure), in either near-anoxic (~0% O$_2$), hypoxic (~1% O$_2$) or normoxic (21% O$_2$) atmosphere; b) the signal-to-noise (fold-change) representation of the data presented in part a; and c) the absolute $^{130}$Te signal as a function of time as determined by mass cytometry analysis of HCT116 cells incubated with 10 µM Telox-2 for 3 hours followed by replacement of Telox-2-containing media with fresh media in either near-anoxic (~0% O$_2$), hypoxic (~1% O$_2$) or normoxic (21% O$_2$) atmosphere; and d) the signal-to-noise (fold-change) representation of the data presented in part c.
Figures 9C, 9D:
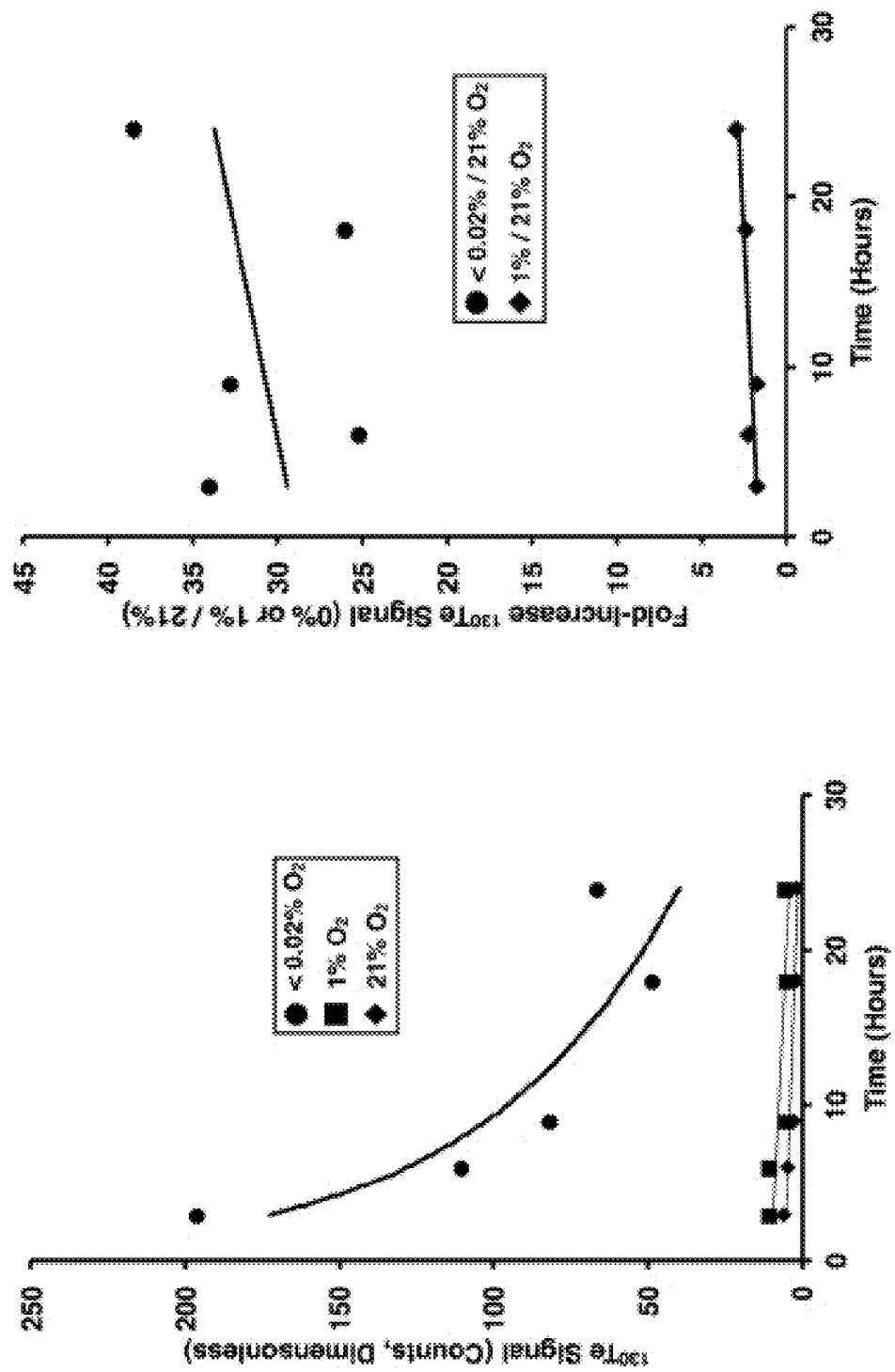
Figure 10C:
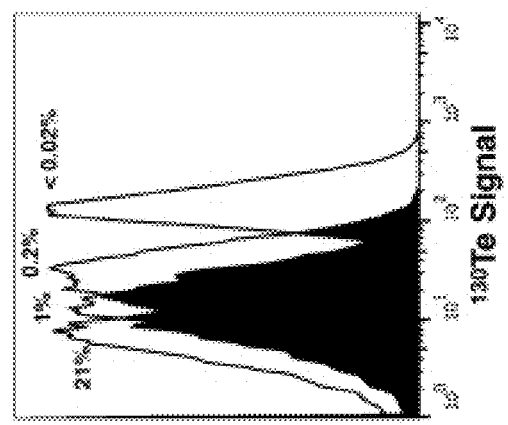
FIGS. 10A-C show a) the mass cytometry histograms of wild-type HCT116 cells incubated with 10 µM of the exemplary compound, Telox-2, for 3 hours in atmosphere containing either 21% O$_2$, 1% O$_2$, 0.2% O$_2$, or <0.02% O$_2$); b) the mass cytometry histograms of mutant HCT116 cells overexpressing POR incubated with 10 µM Telox-2 for 3 hours in atmosphere containing either 21% O$_2$, 1% O$_2$, 0.2% O$_2$ or <0.02% O$_2$; and c) the mass cytometry histograms of mutant HCT116 cells unable to express POR incubated with 10 µM Telox-2 for 3 hours in atmosphere containing either 21% O$_2$, 1% O$_2$, 0.2% O$_2$, or <0.02% O$_2$.
Figure 10B:
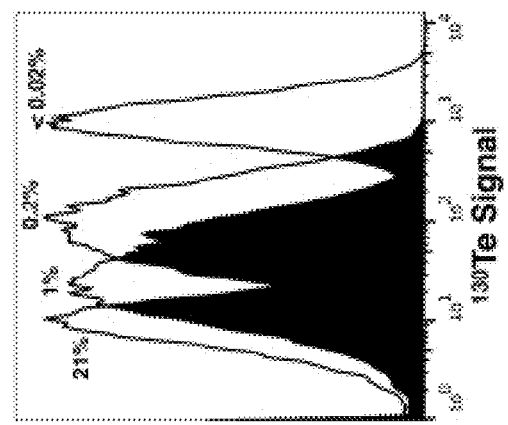
Figure 10A:
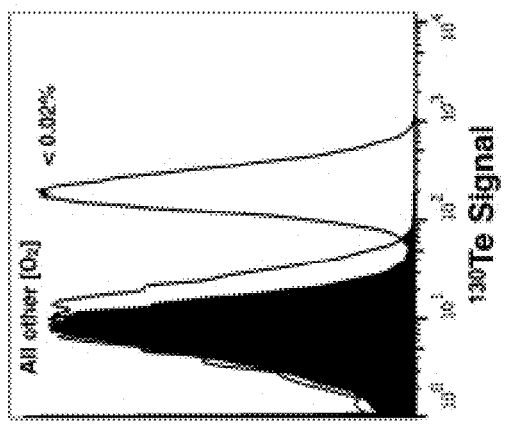

The time-dependence of labelling under conditions of constant drug exposure was then evaluated using the optimized dose (FIG. 10 part a). This experiment demonstrated that signal-to-noise is enhanced as incubation time increases when comparing both near-anoxic and moderately hypoxic cells to the normoxic control. Although a useful experiment for in vitro assays, constant drug exposure conditions are unrealistic for in vivo experiments since drug clearance would be expected to rapidly reduce the probe concentration in an animal model. In order to better simulate an in vivo scenario, the time-dependence of Telox-2 labelling after pulsed exposure to the probe was investigated. In this experiment, cells were exposed to Telox-2 for a period of 3 hours, after which probe-containing media was removed and replaced with fresh media. The cells were then allowed to incubate for (up to) an additional 21 hours before MC analysis was performed (FIG. 9 parts c and d). The results of this experiment indicated that Telox-2-protein conjugates (see Telox-2 Scheme part b) are lost according to an exponential-type decay (FIG. 9 part c). This is consistent with expectations, as the amount of Telox-2-protein conjugate per cell is expected to decrease with time in the absence of additional un-metabolized Telox-2 as cells are expected to divide over the time period investigated, thereby passing ~half of the Telox-2-protein conjugate to daughter cells after each division.

To confirm the reductive metabolism of Telox-2 it investigated using mutant HCT116 cell lines that either overexpressed NADPH:cytochrome P450 oxidoreductase (POR) or had this enzyme knocked out (FIG. 10 part b). In the cell line overexpressing POR, greatly enhanced labelling with Telox-2 (as compared to wild type cells) was observed, suggesting that this enzyme is important in the metabolism and subsequent activation of Telox-2. Interestingly, Telox-2 labelling in the POR-knockout cell line was nearly identical to that in the wild type (FIG. 10 part c). This suggests that cells are able to metabolize Telox-2 through alternative oxidoreductase enzymes that may be upregulated in compensation for the lack of POR.

Figure 11:
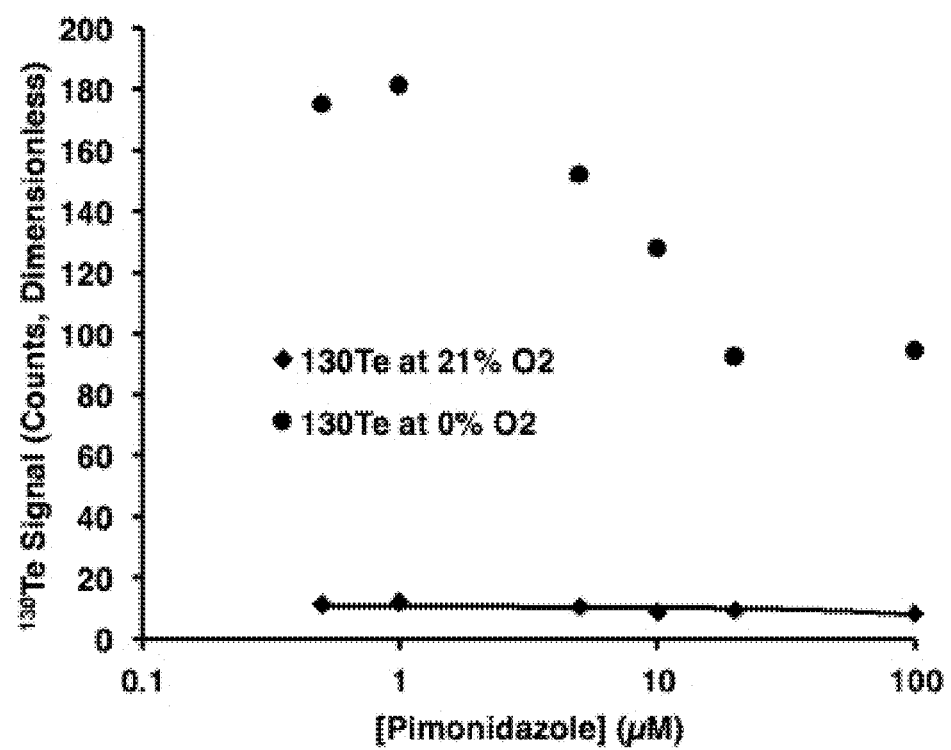
FIG. 11 shows the competitive labelling with the exemplary compound, Telox-2, and pimonidazole in HCT116 cells incubated in either normoxic (21% O$_2$) or near-anoxic (~0% O$_2$) atmosphere. Concentration Telox-2=10 µM. The absolute $^{130}$Te signal was measured using mass cytometry.

Under competitive conditions with pimonidazole, Telox-2 labelling was reduced in a (pimonidazole) dose-dependent manner (FIG. 11). Complete competition was not observed even at excessively high doses of pimonidazole suggesting that a metabolic pathway exists that is capable of reducing Telox-2 but incapable of processing pimonidazole. Competition was only observed under near-anoxic conditions suggesting that the small tellurium signal observed in cells incubated under normoxic conditions is not a result of reductive metabolism.

Example 18

Cathepsin S

Cells are grown under normal conditions and/or one or more test conditions and incubated with a cathepsin S substrate labelled with a tellurophene compound such as

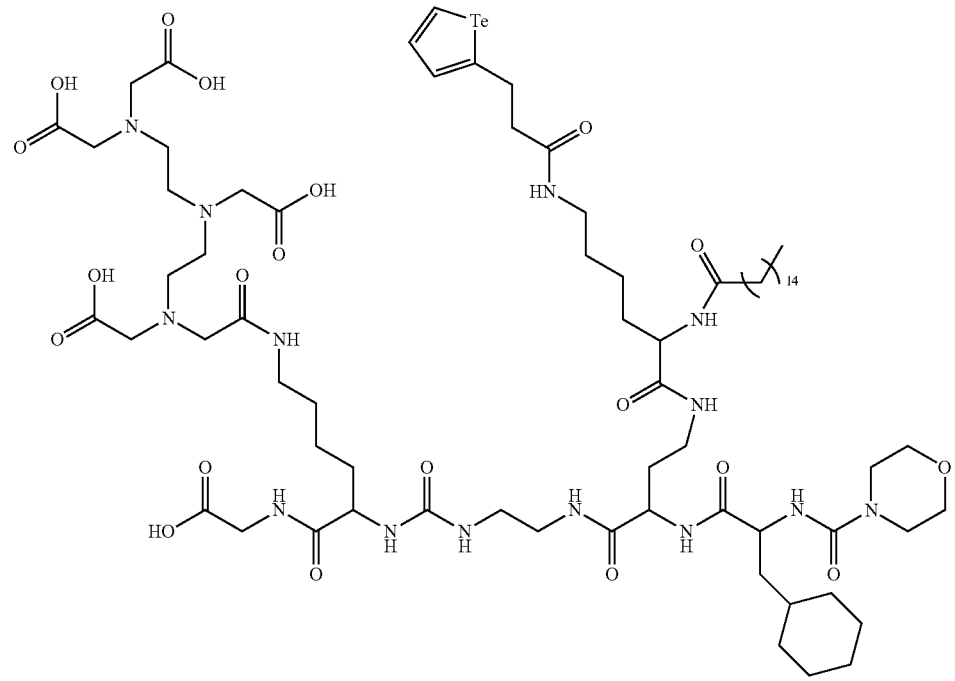

wherein the DTPA portion of the molecule is labelled with a second metal tag (tag2), optionally a tellurophene moiety with a distinct mass. The substrate associates with the membrane due to the compounds fatty acid tail. If Cathepsin S is active, the substrate is cleaved releasing the soluble DTPA portion of the molecule. The ratio of tellurophene/tag2 signal is indicative of cathepsin S activity. For example a 1:1 ratio would be indicative that cathepsin was not active whereas a ratio of less than one would be indicative of activity. These probes can be synthesized by those skilled in the art using schemes similar to literature examples (e.g. Angew. Chem. Int. Ed. Engl. 53(29):7669-7673. doi: 10.1002/anie.201310979 incorporated herein by reference).

Example 19

Enzyme Linked Assay

An alkaline phosphatase (AP) substrate comprising an organotellurophene tag, for example,

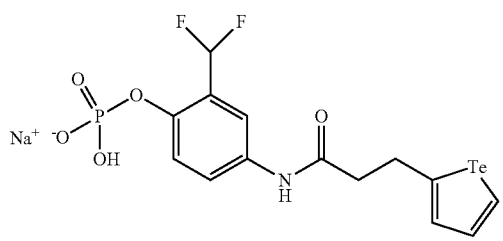

can be prepared using the following scheme

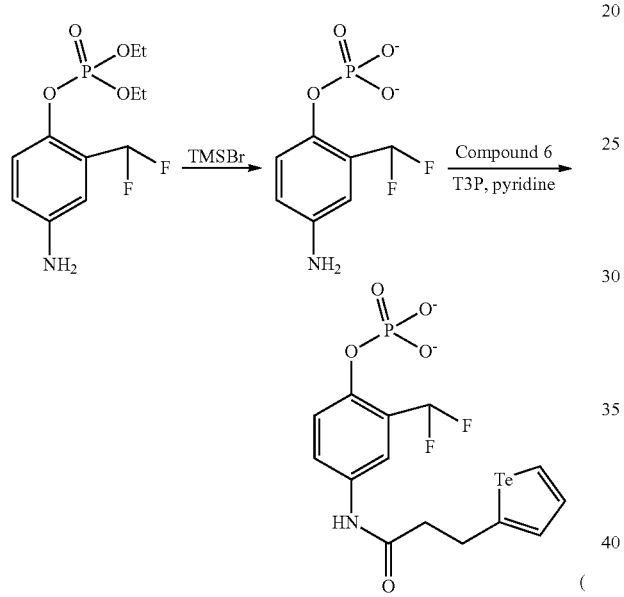

AP can be immobilized to a plate or bead directly or indirectly as part of an antibody conjugate (e.g. where an antibody conjugate has been incubated with an antigen immobilized on a plate or bead). The tellurium tagged substrate, which generates a quinone methide uponphosphate cleavage, is incubated with the bead or well. If AP is present, the phosphate is cleaved and the quinone methide reacts with AP and/or other biomolecules in the vicinity. Tellurium levels are used as a readout of the presence and/or amount of AP present.

AP can be part of an antibody conjugate used for antigen detection on a cell or tissue sample. The tellurium tagged substrate, which generates a quinone methide upon cleavage of the phosphate ester is incubated with the cells or tissue sample. If AP is present the phosphate is cleaved and the quinone methide reacts with AP and/or other biomolecules in the vicinity. Tellurium levels are used as a readout of the presence and/or amount of AP present.

Example 20

Enzyme localization can be performed using tellurophene tagged compounds. Tissue samples are incubated with a tellurophene tagged enzyme substrate that upon cleavage forms a precipitate comprising the tellurophene moiety. For example tellurophene linked 3,3' Diaminobenzidine is a substrate of horse radish peroxidase that produces an insoluble polymer upon reaction. The presence and amount of horse radish peroxidase would be indicated by Tellurium associated with the insoluble polymer. In another example tellurophene bound to a 2-(2'-phosphoryloxyphenyl)-6-[125I]iodo-4-(3H)-quinazolinone would provide a water soluble alkaline phosphatase substrate which releases an insoluble tellurium linked quinazoline which precipitates locally upon phosphate ester cleavage. The amount of alkaline phosphatase activity would correlate with the insoluble tellurium compound formed. Imaging methods are used to detect the tellurium precipitate.

Tables

TABLE 1

Organotellurium compounds investigated

TABLE 1-continued

Organotellurium compounds investigated

11

[Chemical structure: 2-thienyl-Te-CH2CH2-C(=O)-NH-CH2-phenyl]

TABLE 2

LD$_{50}$ values of the organotellurium compounds 8-11.

| Compound | LD$_{50}$ (μM) |
|---|---|
| 8 | 610 ± 290* |
| 9 | 180 ± 60 |
| 10 | 130 ± 20 |
| 11 | 280 ± 30 |

*Compound 8 has a large experimental error due to the lack of solubility. All cells could not be killed at the maximal concentration acceptable for the experiment (2 mM).

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

CITATIONS FOR REFERENCES REFERRED TO IN THE SPECIFICATION

1 O. Ornatsky, D. Bandura, V. Baranov, M. Nitz, M. a Winnik and S. Tanner, J. Immunol. Methods, 2010, 361, 1-20.
2 S. C. De Rosa, L. a Herzenberg and M. Roederer, Nat. Med., 2001, 7, 245-8.
3 S. C. Bendall, G. P. Nolan, M. Roederer and P. K. Chattopadhyay, Trends Immunol., 2012, 33, 323-32.
4 S. C. Bendall, E. F. Simonds, P. Qiu, E. D. Amir, P. O. Krutzik, R. Finck, R. V Bruggner, R. Melamed, A. Trejo, O. I. Ornatsky, R. S. Balderas, S. K. Plevritis, K. Sachs, D. Pe'er, S. D. Tanner and G. P. Nolan, Science, 2011, 332, 687-96.
5 L. J. Edgar, R. N. Vellanki, A. Halupa, D. Hedley, B. G. Wouters and M. Nitz, Angew. Chem. Int. Ed. Engl., 2014, 1-6.
6 F. Wöhler, Justus Liebigs Ann. Chem., 1840, 35, 111-112.
7 L. A. Ba, M. Döring, V. Jamier and C. Jacob, Org. Biomol. Chem., 2010, 8, 4203-16.
8 R. Cunha, I. Gouvea and L. Juliano, An. da Acad. Bras . . . . , 2009, 81, 393-407.
9 S. Shaaban, F. Sasse, T. Burkholz and C. Jacob, Bioorg. Med. Chem., 2014, 22, 3610-9.
10 L. Piovan, P. Milani, M. S. Silva, P. G. Moraes, M. Demasi and L. H. Andrade, Eur. J. Med. Chem., 2014, 73, 280-5.
11 P. Du, N. E. B. Saidu, J. Intennann, C. Jacob and M. Montenarh, Biochim. Biophys. Acta, 2014, 1840, 1808-16.
12 W. Cao, Y. Gu, M. Meineck, T. Li and H. Xu, J. Am. Chem. Soc., 2014, 136, 5132-7.
13 S. G. N. Wollenhaupt, A. Thalita, W. G. Salgueiro, S. Noremberg, G. Reis, C. Viana, P. Gubert, F. A. Soares, R. F. Affeldt, D. S. Lüdtke, F. W. Santos, C. C. Denardin, M. Aschner and D. S. Avila, Food Chem. Toxicol., 2014, 64, 192-199.
14 P. Du, U. M. Viswanathan, K. Khairan, T. Buric, N. E. B. Saidu, Z. Xu, B. Hanf, I. Bazukyan, A. Trchounian, F. Hannemann, I. Bernhardt, T. Burkholz, B. Diesel, A. K. Kiemer, K.-H. Schäfer, M. Montenarh, G. Kirsch and C. Jacob, Medchemcomm, 2014, 5, 25.
15 A. Müller, E. Cadenas, P. Graf and H. Sies, Biochem. Pharmacol., 1984, 33, 3235-3239.
16 V. Jamier, L. a Ba and C. Jacob, Chem.—A Eur. J., 2010, 16, 10920-8.
17 D. F. Meinerz, B. Comparsi, J. Allebrandt, D. Oscar, C. Mariano, D. B. Santos, A. Paula, P. Zemolin, M. Farina, A. L. Dafre, J. B. T. Rocha, T. Posser and J. L. Franco, Springerplus, 2013, 2, 10920-10928.
18 A. Cristina, G. Souza, C. I. Acker, B. M. Gai, J. Sebastião and C. W. Nogueira, Neurochem. Int., 2012, 60, 409-414.
19 A. Ouchi, T. Hyugano and C. Liu, Org. Lett., 2009, 11, 4870-4873.
20 N. Kuhn, P. Faupel and E. Zauder, J. Organomet. Chem., 1986, 302, 6-8.
21 G. Kirsch, M. M. Goodman and F. F. Knapp, Organometallics, 1983, 2, 357-363.
22 K. Kobayashi, K. Tanaka, H. Izawa, Y. Arai and N. Furukawa, Chem.—A Eur. J., 2001, 7, 4272-4279.
23 W. Nakanishi, Y. Ikeda and H. Iwamura, Org. Magn. Reson., 1982, 20, 117-122.
24 W. Bell, D. J. Cole-hamilton, P. N. Culshaw, A. E. D. Mcqueen and J. C. Walton, J. Organomet. Chem., 1992, 430, 43-52.
25 R. U. Kirss and D. W. Brown, Organometallics, 1991, 10, 3597-3599.
26 D. W. Brown, B. K. T. Higa and R. W. Gedridge, Organometallics, 1991, 10, 3589-3596.
27 W. Tyrra, N. V. Kirij, D. Naumann and Y. L. Yagupolskii, J. Fluor. Chem., 2004, 125, 1437-1440.
28 T. M. Mccormick, E. I. Carrera, T. B. Schon and D. S. Seferos, ChemComm, 2013, 49, 11182-11184.
29 A. a Jahnke, B. Djukic, T. M. McCormick, E. Buchaca Domingo, C. Hellmann, Y. Lee and D. S. Seferos, J. Am. Chem. Soc., 2013, 135, 951-4.

30 G. L. Gibson, T. M. Mccormick and D. S. Seferos, J. Phys. Chem., 2013, 117, 16606-16615.
31 M. Kaur, D. S. Yang, J. Shin, T. W. Lee, K. Choi, M. J. Cho and D. H. Choi, Chem. Commun. (Camb)., 2013, 49, 5495-7.
32 M. M. Campos-vallette and R. E. Clavijo C., Spectrosc. Lett., 1985, 18, 759-766.
33 D. P. Sweat and C. E. Stephens, J. Organomet. Chem., 2008, 693, 2463-2464.
34 T. J. Barton and R. W. Roth, J. Organomet. Chem., 1972, 39, 66-68.
35 S. Kotha and P. Khedkar, Chem. Rev., 2012, 112, 1650-80.
36 J. P. Marino and H. N. Nguyen, J. Org. Chem., 2002, 67, 6841-6844.
37 M. X.-W. Jiang, M. Rawat and W. D. Wulff, J. Am. Chem. Soc., 2004, 126, 5970-5971.
38 L. Engman, N. Al-maharik, M. Mcnaughton and G. Powis, Biochim. Biophys. Acta, 2003, 11, 5091-5100.
39 M. McNaughton, L. Engman, A. Birmingham, G. Powis and I. a Cotgreave, J. Med. Chem., 2004, 47, 233-9.
40 C. Pavlik, N. C. Biswal, F. C. Gaenzler, M. D. Morton, L. T. Kuhn, K. P. Claffey, Q. Zhu, M. B. Smith, *Dyes Pigm.* 2011, 89, 9.
41 C. Giesen et al. Nature Methods 11: 417-422 (2014)
42 X Lou, et al. *Angew Chem Int Ed Engl* 2007 46:6111-4
43 D Majonis et al. Anal Chem 2010 82: 8961-9

The invention claimed is:
1. A compound of formula (II):

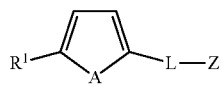

(II)

wherein
A is a naturally occurring isotope of Te;
$R^1$ is selected from H, unsubstituted or substituted $C_1$-$C_{20}$alkyl, unsubstituted or substituted $C_3$-$C_{20}$cycloalkyl, unsubstituted or substituted aryl and an electron withdrawing group;
L is $C_{1-20}$alkylene, unsubstituted or substituted with one or more substituents, and/or optionally interrupted with one or more heteromoieties independently selected from O, S, $NR^7$, and/or optionally interrupted with one or more of C(O) and C(S);
$R^7$ is independently selected from H, protecting group (PG) and $C_{1-6}$ alkyl; and
Z is a biologically active material and/or a salt and/or solvate thereof, wherein the biologically active material is selected from polypeptide, nucleic acid, peptidic nucleic acid, oligosaccharide, polysaccharide lipopolysaccharide, hormone, pharmacologically active substance, steroid, vitamin, amino acid and sugar, preferably wherein the biologically active material is selected from an affinity reagent selected from an antibody or binding fragment thereof, aptamer, avidin reagent, nucleic acid or lectin.
2. The compound of claim 1,
wherein $R^1$ is an electron withdrawing group selected from selected from $C(O)R^2$, $C(R^3)_3$, C≡N, and $NO_2$, wherein $R^2$ is selected from H and $C_{1-6}$alkyl; and
$R^3$ is halo;
wherein the substituents on $R^1$ are independently selected from one or more of halo, C1-6 alkyl and $C_{1-6}$alkoxy;
wherein the substituents on L are independently selected from halo, $C_{1-6}$alkyl, $C_{1-6}$alkoxy, $C(O)R^4$ and $NR^5R^6$, wherein $R^4$ is selected from H and $C_{1-6}$alkyl and $R^5$ and $R^6$ are independently selected from H, PG, C(O) $C_{1-20}$alkyl and $C(O)OC_{1-20}$ alkyl;
wherein $R^1$ is selected from H, unsubstituted or substituted $C_{1-10}$alkyl, unsubstituted or substituted $C_3$-$C_{10}$cycloalkyl, unsubstituted or substituted phenyl and an electron withdrawing group selected from $C(O)R^2$ and $C(R^3)_3$;
the substituents on $R^1$ are independently selected from one or more of halo and $C_{1-3}$alkyl;
$R^2$ is selected from H and $C_{1-6}$ alkyl; and
$R^3$ is F, Cl, Br, and I, preferably wherein $R^1$ is selected from H and $C(R^3)_3$ wherein $R^3$ is F, optionally wherein $R^1$ is H;
wherein L is a $C_{1-25}$alkylene, unsubstituted or substituted with one or more substituents independently selected from $C_{1-3}$alkyl, $C(O)R^4$ and $NR^5R^6$, and/or optionally interrupted with one or more heteromoieties independently selected from O and $NR^7$, and/or optionally interrupted with C(O);
$R^4$ is selected from H and $C_{1-2}$alkyl;
$R^5$ and $R^6$ are independently selected from H, PG, C(O) $C_{1-6}$alkyl and $C(O)OC_{1-6}$alkyl; and
R7 is independently selected from H and PG.
3. The compound of claim 1, wherein
L is a $C_{1-25}$alkylene, unsubstituted or substituted with one or more substituents independently selected from $NR_5R_6$, and/or optionally interrupted with one or more heteromoieties independently selected from 0 and $NR_7$, and/or optionally interrupted with C(O);
$R_5$ and $R_6$ are independently selected from H, PG, and $C(O)OC_{1-4}$alkyl; and
$R_7$ is H.
4. The compound of claim 1, wherein the compound is compatible with biological systems.
5. The compound of claim 4, wherein the compound is non-toxic.
6. The compound of claim 1, wherein the biologically active material is an amino acid.
7. The compound of claim 6, wherein the amino acid is phenylalanine or an analog thereof.
8. The compound of claim 6, wherein the compound is incorporated into a biomolecule target analyte.
9. The compound of claim 6, wherein the compound is for incorporation into a biomolecule target analyte.
10. The compound of claim 9, wherein the biomolecule target analyte is a protein.
11. The compound of claim 1, wherein the biologically active material is a nucleic acid.
12. The compound of claim 1, wherein the biologically active material is an antibody or binding fragment thereof.
13. A kit comprising a compound of formula (II):

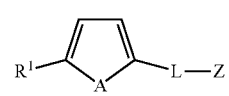

(II)

wherein

A is a naturally occurring isotope of Te;

$R^1$ is selected from H, unsubstituted or substituted $C_1$-$C_{20}$alkyl, unsubstituted or substituted $C_3$-$C_{20}$cycloalkyl, unsubstituted or substituted aryl and an electron withdrawing group;

L is $C_{1-20}$alkylene, unsubstituted or substituted with one or more substituents, and/or optionally interrupted with one or more heteromoieties independently selected from O, S, $NR^7$, and/or optionally interrupted with one or more of C(O) and C(S);

$R^7$ is independently selected from H, protecting group (PG) and $C_{1-6}$ alkyl; and Z is a biologically active material and/or a salt and/or solvate thereof, wherein the biologically active material is selected from polypeptide, nucleic acid, peptidic nucleic acid, oligosaccharide, polysaccharide lipopolysaccharide, hormone, pharmacologically active substance, steroid, vitamin, amino acid and sugar, preferably wherein the biologically active material is selected from an affinity reagent selected from an antibody or binding fragment thereof, aptamer, avidin reagent, nucleic acid or lectin.

* * * * *